United States Patent
Wang et al.

(10) Patent No.: US 12,091,467 B2
(45) Date of Patent: Sep. 17, 2024

(54) CD47 MONOCLONAL ANTIBODIES AND USES THEREOF

(71) Applicant: I-Mab Biopharma US Limited, Rockville, MD (US)

(72) Inventors: Zhengyi Wang, Shanghai (CN); Lei Fang, Shanghai (CN); Bingshi Guo, Shanghai (CN); Jingwu Zang, Shanghai (CN)

(73) Assignee: I-Mab Biopharma US Limited, Rockville, MD (US)

( * ) Notice: Subject to any disclaimer, the term of this patent is extended or adjusted under 35 U.S.C. 154(b) by 506 days.

(21) Appl. No.: 16/989,702

(22) Filed: Aug. 10, 2020

(65) Prior Publication Data
US 2021/0054093 A1 Feb. 25, 2021

Related U.S. Application Data

(62) Division of application No. 15/761,309, filed as application No. PCT/US2017/057535 on Oct. 20, 2017, now abandoned.

(51) Int. Cl.
| | |
|---|---|
| *C07K 16/28* | (2006.01) |
| *A61K 39/395* | (2006.01) |
| *A61K 47/68* | (2017.01) |
| *A61P 35/00* | (2006.01) |
| *C07K 16/30* | (2006.01) |
| *G01N 33/68* | (2006.01) |

(52) U.S. Cl.
CPC ...... *C07K 16/2896* (2013.01); *A61K 47/6803* (2017.08); *A61P 35/00* (2018.01); *C07K 16/30* (2013.01); *G01N 33/6893* (2013.01); *A61K 39/395* (2013.01); *C07K 2317/56* (2013.01); *C07K 2317/569* (2013.01); *G01N 2333/70596* (2013.01)

(58) Field of Classification Search
CPC ........ C07K 16/00; C07K 16/28; C07K 16/30; C07K 2317/56; C07K 2317/569; A61K 39/395
See application file for complete search history.

(56) References Cited

U.S. PATENT DOCUMENTS

| | | | |
|---|---|---|---|
| 4,179,337 A | 12/1979 | Davis | |
| 4,275,149 A | 6/1981 | Litman | |
| 4,301,144 A | 11/1981 | Iwashita | |
| RE30,985 E | 6/1982 | Cartaya | |
| 4,485,045 A | 11/1984 | Regen | |
| 4,496,689 A | 1/1985 | Mitra | |
| 4,544,545 A | 10/1985 | Ryan | |
| 4,560,655 A | 12/1985 | Baker | |
| 4,640,835 A | 2/1987 | Shimizu | |
| 4,657,866 A | 4/1987 | Kumar | |
| 4,670,417 A | 6/1987 | Iwasaki | |
| 4,676,980 A | 6/1987 | Segal | |
| 4,767,704 A | 8/1988 | Cleveland | |
| 4,791,192 A | 12/1988 | Nakagawa | |
| 4,816,567 A | 3/1989 | Cabilly | |
| 4,927,762 A | 5/1990 | Darfler | |
| 5,013,556 A | 5/1991 | Woodle | |
| 5,122,469 A | 6/1992 | Mather | |
| 5,545,806 A | 8/1996 | Lonberg | |
| 5,545,807 A | 8/1996 | Surani | |
| 5,569,825 A | 10/1996 | Lonberg | |
| 5,571,894 A | 11/1996 | Wels | |
| 5,587,458 A | 12/1996 | King | |
| 5,625,126 A | 4/1997 | Lonberg | |
| 5,633,425 A | 5/1997 | Lonberg | |
| 5,641,870 A | 6/1997 | Rinderknecht | |
| 5,661,016 A | 8/1997 | Lonberg | |
| 5,869,046 A | 2/1999 | Presta | |
| 6,075,181 A | 6/2000 | Kucherlapati | |
| 6,150,584 A | 11/2000 | Kucherlapati | |
| 6,322,791 B1 | 11/2001 | Vadas | |
| 6,326,193 B1 | 12/2001 | Liu | |
| 7,332,581 B2 | 2/2008 | Presta | |
| 7,521,541 B2 | 4/2009 | Eigenbrot | |
| 7,829,084 B2 | 11/2010 | Ledbetter | |
| 8,101,719 B2 | 1/2012 | Kikuchi | |
| 8,592,644 B2 | 11/2013 | Harriman | |
| 8,652,788 B2 | 2/2014 | Adamczyk | |
| 8,946,388 B2 | 2/2015 | Sahin | |
| 9,017,675 B2 | 4/2015 | Liu et al. | |
| 9,221,908 B2 | 12/2015 | Frazier et al. | |

(Continued)

FOREIGN PATENT DOCUMENTS

| | | |
|---|---|---|
| AU | 2017332960 B2 | 9/2019 |
| CA | 3097443 A1 | 5/2020 |

(Continued)

OTHER PUBLICATIONS

Paul, Fundamental Immunology, 3rd Edition, 1993, pp. 292-295.*
Murphy et al., Journal of Immunological Methods, vol. 463, p. 127-133, 2018.*
Bendig, Methods: A Companion to Methods in Enzymology, 1995; 8:83-93.
Brown M. et al., "Tolerance of single, but not multiple, amino acid replacements in antibody VHI CDR 2: a means of minimizing B cell wastage from somatic hypermutation?" J Immunol, 1996, 156 (9): 3285-3291.
Colman, Research in Immunology, 1994, 145:33-36.
Extended European Search Report issued on EP Patent Application No. 17849891.1 dated Jul. 18, 2019.

(Continued)

*Primary Examiner* — Hong Sang
(74) *Attorney, Agent, or Firm* — MORRISON & FOERSTER LLP

(57) ABSTRACT

The present invention provides novel CD47 antibodies or immunologically active fragments thereof that have low immunogenicity in humans and cause low or no level of red blood cell depletion or hemagglutination, as well as pharmaceutical compositions containing such antibodies that can be used for treatment diseases mediated by CD47 or inhibition of phagocytosis or platelet aggregation.

4 Claims, 48 Drawing Sheets

Specification includes a Sequence Listing.

(56) References Cited

U.S. PATENT DOCUMENTS

| | | |
|---|---|---|
| 9,266,952 B2 | 2/2016 | Teige |
| 9,380,769 B2 | 7/2016 | Leighton |
| 9,382,320 B2 | 7/2016 | Liu et al. |
| 9,388,239 B2 | 7/2016 | Baldi et al. |
| 10,774,132 B2 | 9/2020 | Smider et al. |
| 2008/0131431 A1 | 6/2008 | Smith et al. |
| 2010/0239579 A1 | 9/2010 | Smith |
| 2014/0140989 A1 | 5/2014 | Eckelman |
| 2015/0238604 A1 | 8/2015 | Eckelman et al. |
| 2015/0353642 A1 | 12/2015 | Tykocinski |
| 2016/0177276 A1 | 6/2016 | Lo |
| 2018/0088140 A1 | 3/2018 | Grabert et al. |
| 2018/0312600 A1 | 11/2018 | Poirier et al. |
| 2020/0377611 A1 | 12/2020 | Wang et al. |
| 2020/0385465 A1 | 12/2020 | Wan et al. |
| 2020/0407441 A1 | 12/2020 | Wang et al. |
| 2021/0054093 A1 | 2/2021 | Wang et al. |
| 2021/0095019 A1 | 4/2021 | Wang et al. |
| 2021/0269522 A1 | 9/2021 | Wang et al. |
| 2023/0174649 A1 | 6/2023 | Cao |
| 2023/0393144 A1 | 12/2023 | Cao |
| 2023/0399400 A1 | 12/2023 | Wang |

FOREIGN PATENT DOCUMENTS

| | | |
|---|---|---|
| CN | 101133083 A | 2/2008 |
| CN | 102643344 A | 8/2012 |
| CN | 102725633 A | 10/2012 |
| CN | 103429618 A | 12/2013 |
| CN | 104271757 A | 1/2015 |
| CN | 104628858 A | 5/2015 |
| CN | 105101997 A | 11/2015 |
| CN | 108738313 A | 11/2018 |
| CN | 110573622 A | 12/2019 |
| CN | 110582515 A | 12/2019 |
| EP | 3336185 A1 | 6/2018 |
| EP | 3411071 A1 | 12/2018 |
| JP | H11507927 A | 7/1999 |
| JP | 2015508072 A | 3/2015 |
| JP | 2016507555 A | 3/2016 |
| KR | 20180056682 A | 5/2018 |
| KR | 102136742 B1 | 7/2020 |
| WO | 1987000195 A1 | 1/1987 |
| WO | 1990003430 A1 | 4/1990 |
| WO | 199110741 A1 | 7/1991 |
| WO | 199316185 A2 | 8/1993 |
| WO | 199633735 A1 | 10/1996 |
| WO | 199634096 A1 | 10/1996 |
| WO | 1998024893 A2 | 6/1998 |
| WO | 9940940 A1 | 8/1999 |
| WO | 200042072 A2 | 7/2000 |
| WO | 2001029058 A1 | 4/2001 |
| WO | 200196584 A2 | 12/2001 |
| WO | 2005044857 A1 | 5/2005 |
| WO | WO 2005/045436 A1 | 5/2005 |
| WO | 2007133811 A2 | 11/2007 |
| WO | 2011019844 A1 | 2/2011 |
| WO | 2012162422 A2 | 11/2012 |
| WO | 2013059159 A1 | 4/2013 |
| WO | WO 2013/119714 A1 | 8/2013 |
| WO | 2014121093 A1 | 8/2014 |
| WO | WO 2014/123580 A1 | 8/2014 |
| WO | WO 2015/191861 A1 | 12/2015 |
| WO | 2016024021 A1 | 2/2016 |
| WO | 2016044021 A1 | 3/2016 |
| WO | WO 2016/081423 A1 | 5/2016 |
| WO | WO 2016/109415 A1 | 7/2016 |
| WO | WO 2016/141328 A3 | 9/2016 |
| WO | 2017053423 A1 | 3/2017 |
| WO | WO 2017/121771 A1 | 7/2017 |
| WO | WO 2018/075857 A8 | 4/2018 |
| WO | 2019091473 A1 | 5/2019 |
| WO | 2020098232 A1 | 5/2020 |
| WO | WO 2020/088580 A1 | 5/2020 |
| WO | 2020247820 A1 | 12/2020 |
| WO | WO 2021/219092 A1 | 11/2021 |
| WO | WO 2022/057939 A1 | 3/2022 |
| WO | WO 2022/078465 A1 | 4/2022 |
| WO | WO 2022/078466 A1 | 4/2022 |

OTHER PUBLICATIONS

Liu J. et al., "Pre-Clinical Development of a Humanized Anti-CD47 Antibody with Anti-Cancer Therapeutic Potential", PLoS One, Sep. 2015, vol. 10, No. 9, e0137345.

Rudikoff S. et al., "Single amino acid substitution altering antigen-binding specificity", PNAS, 1982, vol. 79, pp. 1979-1983.

Mawby et al., "Isolation and characterization of CD47 glycoprotein: a multispanning membrane protein which is the same as integrin-associated protein (IAP) and the ovarian tumour marker OA3." Biochemical Journal 304.2 (1994): 525-530.

Meng et al., "TJC4, a differentiated anti-CD47 antibody with novel epitope and RBC sparing properties." (2019): 4063-4063.

O'Connor et al., "A novel peptide that defines a functional epitope on CD 47 identified using phage display", Gastroenterology, vol. 120, No. 5, (May 16, 2008), p. A-59.

Wang et al., "A novel immunocytokine fusion protein combining tumor-targeting anti-CD47 antibody with GM-CSF cytokine for enhanced antitumor efficacy" [abstract]. In: Proceedings of the American Association for Cancer Research Annual Meeting 2018; Apr. 14-18, 2018; Chicago, IL. Philadelphia (PA): AACR; Cancer Res 2018;78(13 Suppl):Abstract nr 5622.

Weiskopf et al., "CD 47-blocking immunotherapies stimulate macrophage-mediated destruction of small-cell lung cancer", The Journal of Clinical Investigation, vol. 126, No. 7, Jun. 13, 2016, pp. 2610-2620.

Khantasup et al., Monoclonal Antibodies in Immunodiagnosis and Immunotherapy, 2015, 34(6): 404-417.

Carter et al., Endocrine-Related Cancer, 2004, 11 :659-687.

International Search Report for PCT/CN2017/057535, dated Mar. 19, 2018.

International Search Report for PCT/CN2019/114662, dated Jan. 23, 2020.

PCT/CN2019/114662 Written Opinion, dated Jan. 23, 2020.

Abhinandan, K.R. et al. (Aug. 2008, e-pub. Jul. 9, 2008). "Analysis and Improvements To Kabat and Structurally Correct Numbering Of Antibody Variable Domains," Molecular Immunology 45(14):3832-3839.

Al-Lazikani, B. et al. (1997). "Standard Conformations for the Canonical Structures of Immunoglobulins," J. Mol. Biol. 273:927-948.

Almagro, J.C. et al. (Jan. 1, 2008). "Humanization of Antibodies," Frontiers In Bioscience 13:1619-1633.

Baca, M. et al. (Apr. 18, 1997). "Antibody Humanization Using Monovalent Phage Display," J. Biol. Chem. 272 (16):10678-10684.

Barnes, D. et al. (Mar. 1, 1980). "Methods for Growth of Cultured Cells In Serum-Free Medium," Anal. Biochem. 102(2):255-270.

Behrens, L. M. et al. (2022). "Targeting the CD47-SIRPa Innate Immune Checkpoint to Potentiate Antibody Therapy in Cancer by Neutrophils," Cancers 14:3366, 41 pages.

Boerner, P. et al. (Jul. 1, 1991). "Production of Antigen-Specific Human Monoclonal Antibodies from In Vitro-Primed Human Splenocytes," J. Immunol. 147(1):86-95.

Brennan, M. et al. (Jul. 5, 1985). "Preparation of Bispecific Antibodies by Chemical Recombination of Monoclonal Immunoglobulin G1 Fragments," Science 229:81-83.

Brüggemann, M. et al. (1993). "Designer Mice: The Production of Human Antibody Repertoires in Transgenic Animals," Year in Immunol. 7:33-40.

Caron, P.C. et al. (Oct. 1, 1992). "Engineering Humanized Dimeric Forms of IgG Are More Effective Antibodies," J. Exp Med. 176: 1191-1195.

Carter, P. et al. (Feb. 1992). "High Level *Escherichia Coli* Expression and Production of a Bivalent Humanized Antibody Fragment," Bio/Technology 10:163-167.

(56) References Cited

OTHER PUBLICATIONS

Carter, P. et al. (May 1992). "Humanization of an Anti-p185HER2 Antibody for Human Cancer Therapy," Proc. Natl. Acad. Sci. USA 89:4285-4289.
Casset, F. et al. (2003). "A Peptide Mimetic Of An Anti-CD4 Monoclonal Antibody By Rational Design," BBRC 307:198-205, 8 pages.
Chao, M.P. et al. (Feb. 4, 2012). "The CD47-Sirpa Pathway In Cancer Immune Evasion And Potential Therapeutic Implications," Current Opinion in Immunology 24(2): 225-232, 13 pages.
Chen, C. et al. (Jun. 15, 1995). "Enhancement and Destruction of Antibody Function by Somatic Mutation: Unequal Occurrence is Controlled by V Gene Combinatorial Associations," The EMBO Journal 14(12):2784-2794.
Chen, Y. et al. (1999). "Selection and Analysis of an Optimized Anti-VEGF Antibody: Crystal Structure of an Affinity-Matured Fab In Complex With Antigen," J. Mol. Biol 293:865-881.
Cheson, B.D. et al. (Sep. 20, 2014). "Recommendations for Initial Evaluation, Staging, and Response Assessment of Hodgkin and Non-Hodgkin Lymphoma: The Lugano Classification," J Clin Oncol 32(27):3059-3068.
Chothia, C. et al. (1986). "The Relation Between the Divergence of Sequence and Structure in Proteins," The EMBO Journal 5(4):823-826.
Chothia, C. et al. (Aug. 20, 1987). "Canonical Structures for the Hypervariable Regions of Immunoglobulins," J. Mol. Biol. 196(4):901-917.
Chothia, C. et al. (Dec. 5, 1985). "Domain Association In Immunoglobulin Molecules. The Packing Of Variable Domains," J. Mol. Biol. 186(3):651-663.
Clackson, T. et al. (Aug. 15, 1991). "Making Antibody Fragments Using Phage Display Libraries," Nature 352:624-628.
Cole, S.P.C. et al. (1985). "The EBV-Hybridoma Technique and Its Application to Human Lung Cancer," in Monoclonal Antibodies and Cancer Therapy, Alan R. Liss, p. 77-96.
Creighton, T.E. (1983). Proteins: Structure and Molecular Properties, W.H. Freeman & Co., San Francisco, pp. 79-86.
Eisenhauer, E.A. et al. (2009) "New Response Evaluation Criteria in Solid Tumors: Revised RECIST Guideline (version 1.1)," Eur. J. Cancer 45:228-247.
Epstein, D.A. et al. (Jun. 1985). "Biological Activity of Lipsome-Encapsulated Murine Interferon y is Mediated by Cell Membrane Receptor," Proc. Natl. Acad. Sci. USA 82:3688-3692.
Evan, G.I. et al. (Dec. 1985). "Isolation of Monoclonal Antibodies Specific for Human c-myc Proto-Oncogene Product," Mol. Cell. Biol. 5(12):3610-3616.
Extended European Search Report, mailed Dec. 23, 2022, for EP Application No. 22182052.5, filed Jun. 29, 2022, 9 pages.
Extended European Search Report, mailed Feb. 28, 2022, for EP Application No. 19883732.0, filed Oct. 19, 2020, 15 pages.
Fellouse, F.A et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.
Fishwild, D.M. et al. (Jul. 1996). "High-Avidity Human IgGK Monoclonal Antibodies from a Novel Strain of Minilocus Transgenic Mice," Nature Biotechnol. 14:845-851.
Gabizon, A. et al. (Oct. 4, 1989). "Pharmacokinetics and Issue Distribution of Doxorubicin Encapsulated in Stable Liposomes With Long Circulation Times," J. National Cancer Inst. 81(19)1484-1488.
Gao, J. et al. (Mar. 2011). "Affibody-Based Nanoprobes For HER2-Expressing Cell And Tumor Imaging," Biomaterials 32(8): 2141-2148.
Graham, F.L. et al. (1977). "Characteristics of a Human Cell Line Transformed by DNA from Human Adenovirus Type 5," J. Gen Virol. 36:59-72.
Griffiths, A.D. et al. (1993). "Human Anti-Self Antibodies with High Specificity from Phage Display Libraries," Embo J. 12(2):725-734.
Ham, R.G. et al. (1979). "Media and Growth Requirements," Chapter 5 in Cell Culture-Methods in Enzymology, Jakoby, W.B. ed et al. Academic Press, San Diego, 58:44-93.
Hammerling, G.J. et al. Eds. (1981). "Monoclonal Antibodies and T-Cell Hybridomas," Chapter 12 In Research Monographs in Immunology Elsevier: New York, NY, 3:563-681.
Harlow, E. et al. (1988). Antibodies A Laboratory Manual, Table of Contents only, 9 pages.
Holm, P. et al. (Feb. 2007). "Functional Mapping and Single Chain Construction Of The Anti-Cytokeratin 8 Monoclonal Antibody TS1," Mol. Immunol. 44(6):1075-1084.
Hongo, J.A.S. et al. (1995). "Development and Characterization of Murine Monoclonal Antibodies to the Latency-Associated Peptide of Transforming Growth Factor Beta1," Hybridoma 14(3):253-260.
Hoogenboom, H.R. (2002). "Overview of Antibody Phage-Display Technology and its Applications," in Chapter 1 of Methods in Molecular Biology, O'Brien, P.M. (ed.) et al., Humana Press Inc., Totowa, NJ, 178:1-37.
Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.
Hwang, K.J. et al. (Jul. 1980). "Hepatic Uptake and Degradation of Unilamellar Sphingomyelin/Cholesterol Liposomes: A Kinetic Study." Proc. Natl. Acad. Sci. USA 77:4030-4034.
I-Mab Biopharma. (Mar. 6, 2018). "A Novel Immunocytokine Fusion Protein Combining Tumor-Targeting Anti-CD47 Antibody with GM-CSF Cytokine for Enhanced Anti-Tumor Efficacy," last visited Sep. 21, 2022, 2 pages.
International Preliminary Report on Patentability, issued May 12, 2020, for PCT Application No. PCT/CN2018/114975, filed Nov. 12, 2018, 8 pages.
International Search Report and Written Opinion, Feb. 13, 2019, for PCT Application No. PCT/CN2018/114975, filed Nov. 12, 2018, 18 pages.
International Search Report and Written Opinion, mailed Jan. 13, 2022, for PCT Application No. PCT/ CN2021/123893, filed Oct. 14, 2021, 15 pages.
International Search Report and Written Opinion, mailed Jan. 17, 2022, for PCT Application No. PCT/ CN2021/123892, filed Oct. 14, 2021, 10 pages.
International Search Report and Written Opinion, mailed Jul. 10, 2019, for PCT Application No. PCT/CN2019/085096, filed Apr. 30, 2019, 6 pages.
International Search Report and Written Opinion, mailed Mar. 19, 2018, for PCT Application No. PCT/ US2017/057535, filed Oct. 20, 2017, 12 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.
Johnson, G. et al. (2003). "The Kabat Database and a Bioinformatics Example," Chapter 2 in Methods in Molecular Biology, Lo, B.K.C., ed., Human Press, Totowa, N.J., 248:1-25.
Jokerst, J.V. et al. (Mar. 7, 2011). "Affibody-Functionalized Gold-Silica Nanoparticles For Raman Molecular Imaging Of The Epidermal Growth Factor Receptor," Small., 7(5):625-633.
Jones, P.T. et al. (May 29, 1986). "Replacing The Complementarity-Determining Regions In A Human Antibody With Those From A Mouse," Nature 321:522-525.
Kabat, E.A. et al. (1991). Sequences of Proteins of Immunological Interest, 5th Ed. Public Health Service, National Institutes of Health, Bethesda MD., Table of Contents, 21 pages.
Kojima, Y. et al. (Jul. 20, 2016). "CD47-Blocking Antibodies Restore Phagocytosis And Prevent Atherosclerosis," Nature 536: 86-90, 20 pages.
Köhler, G. et al. (Aug. 7, 1975). "Continuous Cultures of Fused Cells Secreting Antibody of Predefined Specificity," Nature 256:495-497.

(56) References Cited

OTHER PUBLICATIONS

Lee, C.V. et al. (2004). "Bivalent Antibody Phage Display Mimics Natural Immunoglobulin," J. Immunol. Methods 284(1-2):119-132.
Lee, C.V. et al. (2004). "High-Affinity Human Antibodies From Phage-Displayed Synthetic Fab Libraries With A Single Framework Scaffold," J. Mol. Biol. 340:1073-1093.
Lefranc, M.-P. (2013). "IMGT Unique Numbering," Encyclopedia of Systems Biology 952-959.
Li, H. et al. (Feb. 2006, e-published on Jan. 22, 2006). "Optimization of Humanized IgGs in Glycoengineered Pichia Pastoris," Nature Biotechnology 24(2):210-215.
Lonberg, N. (2008, e-pub. Jul. 21, 2008). "Fully Human Antibodies From Transgenic Mouse and Phage Display Platforms," Curr. Opin. Immunol. 20:450-459.
Lonberg, N. et al. (1995, e-pub. Jul. 10, 2009). "Human Antibodies From Transgenic Mice," Int. Rev. Immunol. 13(1):65-93.
Lonberg, N. et al. (Apr. 28, 1994). "Antigen-Specific Human Antibodies From Mice Comprising Four Distinct Genetic Modifications," Nature 368(6474):856-859.
Maccallum, R.M. et al. (1996). "Antibody-Antigen Interactions: Contact Analysis and Binding Site Topography," J. Mol. Biol. 262:732-745.
Marks, J.D. et al. (1991). "By-Passing Immunization Human Antibodies from V-gene Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10:779-783.
Martin, F.J. et al. (1982). "Irreversible Coupling of Immunoglobulin Fragments to Preformed Vesicles," J. Biol. Chem. 257(1):286-288.
Mather, J.P. (1980). "Establishment and Characterization of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals N.Y. Acad. Sci. 383:44-68.
Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.
Morrison, S.L. (Apr. 28, 1994). "Success in Specification," Nature 368:812-813.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Neuberger, M. (Jul. 1996). "Generating High-Avidity Human Mabs in Mice," Nature Biotechnology 14:826, 1 page.
Novotný, J. et al. (1985). "Structural Invariants of Antigen Binding: Comparison of Immunoglobulin VL-VH and VL-VL Domain Dimmers," Proc. Natl. Acad. Sci. USA, 82:4592-4596.
Oostendrop, M. et al. (Jun. 2015, e-pub May 18, 2015). "When Blood Transfusion Medicine Becomes Complicated Due to Interference by Monoclonal Antibody Therapy," Transfusion 55(6 Pt 2):1555-1562.
Paborsky, L.R. et al. (1990). "Mammalian Cell Transient Expression of Tissue Factor for the Production of Antigen," Protein Eng. 3(6):547-553.
Penichet, M.L. et al. (Feb. 1, 2001). "Antibody—Cytokine Fusion Proteins For The Therapy Of Cancer," J. Immunol. Methods 248:91-101.
Plückthun, A. (1994). "Antibodies from *Escherichia Coli*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Presta, L.G. et al. (2002). "Engineering Therapeutic Antibodies for Improved Function," Biochemical Society Transactions 30(4):487-490.
Presta, L.G. et al. (Sep. 1, 1993). "Humanization of an Antibody Directed Against IgE," J. Immunol. 151(2):2623-2632.
Remington's Pharmaceutical Sciences. (1980). 16th edition, Osol, A. Ed, pp. 1-2, (Table of Contents Only).
Reyalnd, L. et al. (Apr. 2020). "Two Case Reports Involving Therapeutic Monoclonal Anti-CD47 (Hu5F9-G4), it's Effect on Compatibility Testing and Subsequent Selection of Components for Transfusion," Transfus Med., 4 pages.
Riechmann, L. et al. (Mar. 24, 1988). "Reshaping Human Antibodies for Therapy," Nature 332:323-329.
Seymour, L. et al. (Mar. 2017). "iRECIST: Guidelines for Response Criteria for Use in Trials Testing Immunotherapeutics," Lancet Oncol. 18(3):e143-e152, 22 pages ..
Shields, R.L. et al. (Mar. 2, 2001). "High Resolution Mapping of the Binding Site of Human IgG1 for FcγRI, FcγRII, FcγIII, and Fc Rn and Design of IgG1 Variants With Improved Binding to the FcγR," J. Biol. Chem. 9(2):6591-6604.
Shoji-Hosaka, E. et al. (2006). "Enhanced Fc-Dependent Cellular Cytotoxicity of Fc Fusion Proteins Derived from TNF Receptor II and LFA-3 by Fucose Removal from Asn-Linked Oligosaccharides," J. Biochem. 140(6):777-783.
Shopes, B. et al. (May 1, 1992). "A Genetically Engineered Human IgG Mutant With Enhanced Cytolytic Activity," J. Immunol. 148:2918-2922.
Sidhu, S.S. et al. (2004). "Phage-Displayed Antibody Libraries of Synthetic Heavy Chain Complementarity Determining Regions," J. Mol. Biol. 338(2):299-310.
Sikic, B. I. et al. (Apr. 20, 2019). "First-in-Human, First-in-Class Phase I Trial of the Anti-CD47 Antibody Hu5F9-G4 in Patients With Advanced Cancers," J Clin Oncol 37(12):946-953.
Sims, M.J. et al. (Aug. 15, 1993). "A Humanized CD18 Antibody Can Block Function Without Cell Destruction," J. Immunol. 151(4):2296-2308.
Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.
Thakor A.S. et al. (Apr. 20, 2011). "The Fate And Toxicity Of Raman-Active Silica-Gold Nanoparticles In Mice," Sci. Transl. Med., 3(79):79ra33, 12 pages.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Van Heertum, R.L. et al. (Jun. 13, 2017). "Lugano 2014 Criteria for Assessing FDG-PET/CT in Lymphoma: An Operational Approach for Clinical Trials," Drug Des. Devel. Ther. 11:1719-1728.
Veliquette, R. et al. (Feb. 2019). "Monoclonal Anti-CD47 Interference in Red Cell and Platelet Testing," Transfusion 59:730-737.
Vitetta, E.S. et al. (Nov. 20, 1987). "Redesigning Nature's Poisons to Create Anti-Tumor Reagents," Science 238:1098-1104.
Vollmers, H.P. et al. (2005). "Death By Stress: Natural IgM-Induced Apoptosis," Methods and Findings in Experimental and Clinical Pharmacology 27(3):185-191.
Vollmers, H.P. et al. (2005). "The 'Early Birds': Natural IgM Antibodies and Immune Surveillance," Histology and Histopathology, 20(3):927-937.
Willingham, S.B. et al. (Apr. 24, 2012, e-pub. Mar. 26, 2012). "The CD47-Signal Regulatory Protein Alpha (SIRPa) Interaction is a Therapeutic Target for Human Solid Tumors," Proc. Natl. Acad. Sci. USA 109(17):6662-6667.
Winter, G. et al. (1994). "Making Antibodies by Phage Display Technology," Ann. Rev. Immunol. 12:433-455.
Wolff, E.A. et al. (Jun. 1, 1993). "Monoclonal Antibody Homodimers: Enhanced Antitumor Activity in Nude Mice," Can Res 53:2560-2565.
Wright, A. et al. (Jan. 1997). "Effect of Glycosylation on Antibody Function: Implications for Genetics Engineering," Trends Biotechnol. 15:26-32.
Yazaki, P.J. et al. (2003). "Expression of Recombinant Antibodies in Mammalian Cell Lines," Methods in Molecular Biology 248:255-268.

(56) References Cited

OTHER PUBLICATIONS

Young, P.A. et al. (Oct. 1, 2015). "Antibody-Cytokine Fusion Proteins For Treatment Of Cancer: Engineering Cytokines For Improved Efficacy And Safety," Seminars In Oncology 41(5) : 623-636, 19 pages.

* cited by examiner

| Sample | ka (1/Ms) | kd (1/s) | KD (M) |
|---|---|---|---|
| 1F8 | 3.75E+05 | 1.04E-03 | 2.8E-09 |
| 13H3 | 5.33E+05 | 2.47E-04 | 4.6E-10 |
Fig. 4E
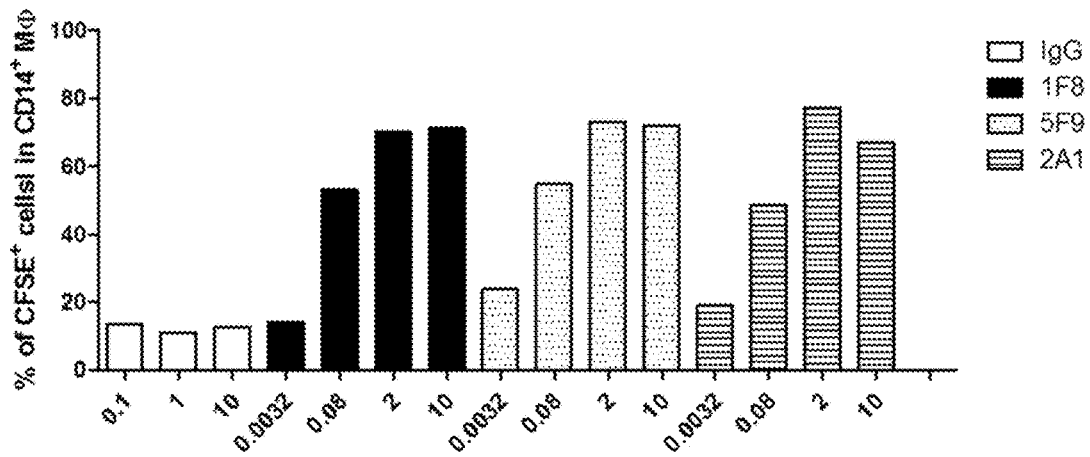
Fig. 5A
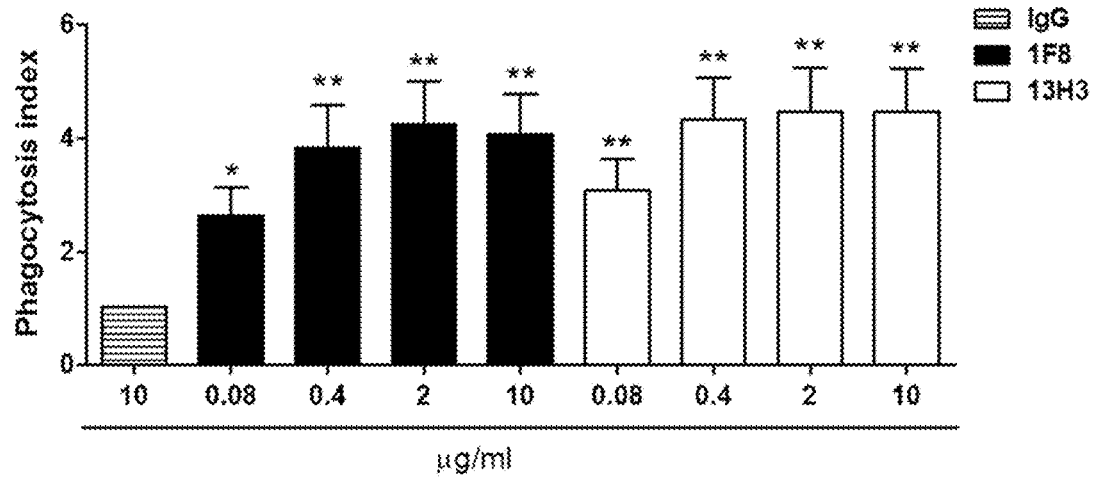
Fig. 5B

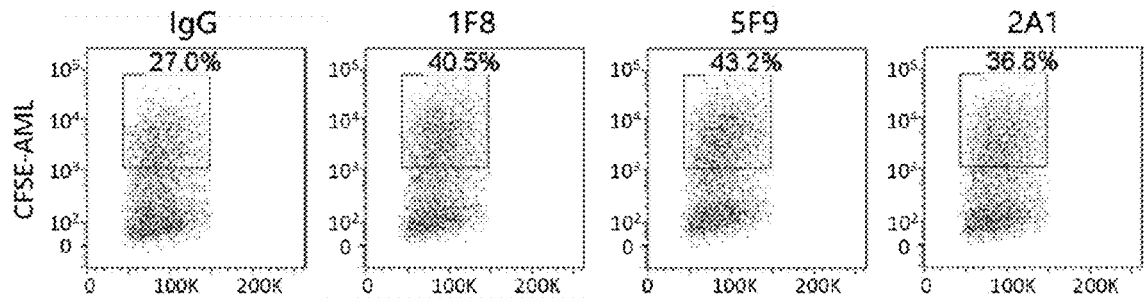
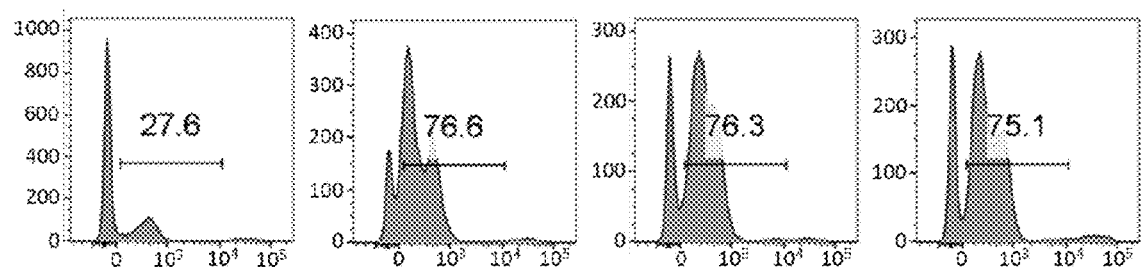
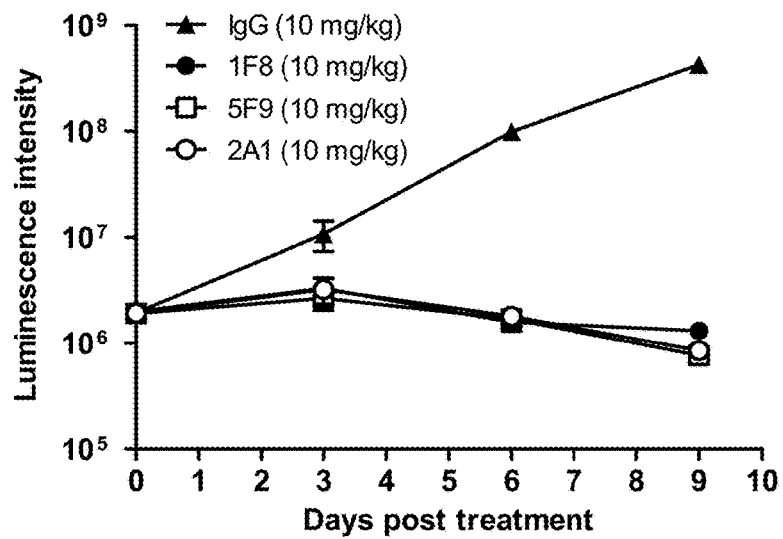
Fig. 14A

| Geometry | Strong stain | Weak stain |
|---|---|---|
| Diffuse (all cells) | 6 | 5 |
| Moderate (most/many cells) | 4 | 3 |
| Focal (few cells) | 2 | 1 |
| Negative | 0 | |

Structure of 5F9/CD47 complex

Structure of 1F8/CD47 complex

Comparison of interaction motif of 5F9 and 1F8 with CD47

Single dose

Amino Acid Sequences:

>CD47-1A1
VH

SEQ ID NO.: 1

QVQLQQSGGGLVQPGGSLRLSCTASGFTFSSYAMSWVRQAPGKGLEWVSAISGSGGSTYYADSVKGRFTISRDNSKN
TLYLQMNSLRVEDTAVYYCARYSIGRHTFDHWGQGTLVTVSA

VL

SEQ ID NO.: 2

NFMLTQPHSVSESPGKTVTISCTRSSGGIASNFVQWYQQRPGSVPTTVIYRDNQRPSGVPDRFSGSVDSSSNSASLT
ISGLKTDDEADYYCQSYDDHNHWVFGGGTKLTVL

>CD47-1F8
VH

SEQ ID NO.: 3

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

VL

SEQ ID NO.: 4

DIVMTQSPDSLAVSLGERATINCKSSQSVLYSSNNRNYLAWYQQKPGQPPKLLINQASTRASGVPDRFSGSGSGTEF
TLIISSLHAEDVAIYYCQQYYTPPLAFGGGTKLEIK

>CD47-2A11
VH

SEQ ID NO.: 5

QVQLQQSGGGLVQPGGSLRLSCAASGFTFSGYAMTWVRQAPGKGLEWVSAITSTGGRTYYADSVKGRFTTSRDNSRN
TLYLQMNSLRAEDTAVYYCARESNFRAFDIWGQGTMVTVSA

VL

SEQ ID NO.: 6

EIVLTQSPLSLPVTPGEPASISCRSSQSLLHSNGYNYLDWYLQKPGQSPQLLIYLNSNRASGVPDRFSGSGSGTDFT
LQISRVEAEDVGVYYCMQALQIPPTFGGGTKVDIK

>CD47-2C2
VH

SEQ ID NO.: 7

EVQLVESGGGLVQPGGSLRLSCAASGFTFIDAWMTWVRQAPGKGLEWVSVIYSGGSTYYADSVKGRFTISRDNSKNT
LYLQMNSLRAEDTAVYYCARGARGHPGQDYWGQGTLVTVSA

SEQ ID NO.: 8

NFMLTQPHSVSESPGKTVTISCTRSSGTIASNFVQWYQQRPGSSPTPVIFENDRRPSGVPDRFSGSIDSSSNSASLT
ISSLNTEDKADYYCQSYDSSTHGWVFGGGTQLTVL

>CD47-2D7
VH

SEQ ID NO.: 9

QVNLRESGGGLVQPGGSLRLSCAASGFTFSDYYMSWIRQAPGGGLEWVSYTSRFGSDTNYADSVKGRFTISRDNVQN
SLYLQMNSLRAEDTAVYYCVRDVHNRDAYWGQGTLVTVSA
VL

SEQ ID NO.: 10

SYVLTQPPSASGTPGQRVTISCSGSSSNIGGNSVSWYQQLPGTAPKLLIYRNHQRPSGVPDRFSGSKSGTSASLAIS
GLRSDDEADYYCATWDFSLSGFVFGTGTKVTVL

>CD47-2G4
VH

SEQ ID NO.: 11

QVQLVQSGGGLVQPGGSLRLSCAASGFTFSSYAMSWVRQAPGKGLEWVSAISGSGGSTYYADSVKGRFTISRDNSKN
TYYCANTDYYDSSSHTPADYWGQGTLVTVSA
VL

SEQ ID NO.: 12

ETTLTQSPSSLSASVGDRVTITCRASQDIRNDLDWFQQKPGEAPKRLISAASNLQSGVPSRFSGGGSGSEFTLTIHS
LESEDFATYYCQQSYITPPWTFGQGTKLEIK

>CD47-2G11
VH

SEQ ID NO.: 13

QVQLQESGGGLVQPGGSLRLSCAASGFTFSSYGMSWVRQAPGKGLEWVSTISGSGSSTNYADSVKGRFTISRDNSKN
TLFLQMNSLRAEDTAVYFCAKGRYYYDSLDAFDIWGQGTMVTVSA

VL

SEQ ID NO.: 14

EIVLTQSPGTLSLSPGERATLSCRASQEIRTAYLAWYQQKPGQAPRLLIYYASSRATGIPDRFSGSRSGTDFTLTIS
RLEPEDFAVYSCQQYDTSPPTFGQGTRLEIK

SEQ ID NO.: 15

QVQLVESGGGLVQPGGSLRLSCAASGFTFSSYAMSWVRQAPGKGLEWVSAISGTGGSTYYADSVKGRFTISRDNSKN
TLYLQMNSLRAEDTAAYYCAKDKWSSWPTYYFDYWGQGTLVTVSA

VL

SEQ ID NO.: 16

NFMLTQPHSVSESPGKTVTISCTRSSGSIASNYVQWYQQRPGSSPTTVIYEDNQRPSGVPDRFSGSIDSSSNSASLT
ISGLKTEDEADYYCQSYDSSNVIFGGGTKVTVL

>CD47-5H1

VH

SEQ ID NO.: 17

QVQLQVSGGGLVQPGGSLRLSCAASGFTFSSYSMAWVRQAPGKGLEWVAAVSNSGVETYYADSVKGRFTISRDNSKN
TLYLQMNSLRAEDTAVYYCAKRTRQLLTPREFDYWGQGTLVTVLA

VL

SEQ ID NO.: 18

ETTLTQSPSSVSASVGDRVTLTCRASQDITRWLAWYQQKPGKAPKLLIYDASSLQSGVPSRFSGSGSGTDFTLTISS
LQPEDFATYYCQQGSSVPFTFGGGTKVEIK

>CD47-5F6

VH

SEQ ID NO.: 19

QVNLRESGGGLIQPGGSLRLSCAASGFTFTNYAMSWVRQAPGKGLEWVSSVSSAGGSTYYADSVKGRFTISRDNAKN
SLYLQMNSLRAEDTAVYYCARRVNRAFDLWGRGTLVTVSA

VL

SEQ ID NO.: 20

DVVMTQSPGTLSLSPGERATLSCRASQSVSSSYLAWYQQKPGQAPRLLIYGASSRATGIPDRFSGSGSGTDFTLTIS
RLEPEDFAVYYCQQYGSSPPMYTFGQGTKLEIK

>CD47-1F3

VH

SEQ ID NO.: 21

QVQLQESGGGLVQPGGSLRLSCAASGFTFSNAWMSWVRQAPGKGLVWVGRIKSKTDGGTTDYAAPVKGRFTISRDDS
KNTLYLQMNSLKTEDTAVYYCTTDKSYGYTFDYWGQGTLVTVSA

VL

SEQ ID NO.: 22

SYVLTQPPSASGTPGQRVTISCSGSGSNIGSNSVHWYQQLPGTAPKLLIYTNNQRPSGVPDRFSGSKSGISASLAIS

Fig. 26C

GLQSEDEAVYYCATWDDRLSGPVFAAGTKLTVL

>CD47-2A4
VH

SEQ ID NO.: 23

QVNLRESGGGLVKPGGSLRLSCAASGFTFSSYWMHWVRQAPGKGLEWVSAISGSGAGTYYPDSVKGRFTISRDNSKN
TLYLQMNSLRAEDTAVYYCARDRSLSFGFDIWGQGTLVSVSG
VL

SEQ ID NO.: 24

NFMLTQPHSVSGSPGKTVTISCTRSSGSIGSTYVQWYQQRPGSPPTTVIYKDDQRPSGVPDRFSGSIDGSSNSASLT
ISGLETEDEADYYCQSSDTSNLVFGGGTKVTVL

>CD47-2B12
VH

SEQ ID NO.: 25

QVQLQQSGGGLVQPGGSLRLSCAAPGFTFSRYWMSWVRQAPGKGLEWVANIKGDGSQTYYADSVKGRFTISRDNAMK
TVYLQMNSLRAEDTAIYYCAKGAAYHINSWLDPWGQGTLVTVSA
VL

SEQ ID NO.: 26

ETTLTQSPGTLSVSPGERVTLSCRASQSISGNYLAWYQQRPGQAPRLLIYGAFRRATGIPDRFSGSGSGTDFTLTIT
RLEPEDFATYYCQHYNNFPHTFGAGTKVDIK

>CD47-13A11
VH

SEQ ID NO.: 27

KVQLVESGGGLVKPGGSLRLSCAASGITFKHAWMNWVRQAPGKGLEWVGRIKRKTDGETTDYAAPVKGRFSISRDDS
KNTLYLQMNSLKTEDTAVYYCAGSNRAFDIWGQGTMVTVSA
VL

SEQ. ID NO.: 28

DIVMTQSPDSLAVSLGERATINCKSSQSVLYVNNRNYLAWYQQKPGQPPKLLINQASTRASGVPDRFSGSGSGTEF
TLIISSLQAEDVAIYYCQQYYTPPLAFGGGTKLEIK

>CD47-15E1
VH

SEQ ID NO.: 29

KVQLVESGGGLVKPGGSLRLSCAASGFTFNNAWMNWVRQAPGKGLEWVGRIKRKTDGETTDYAAPVKGRFSISRDDS
KNTLYLQMNSLKTEDTAVYYCAGSNRAFDIWGQGTMVTVSA

SEQ. ID NO.: 30

DIVMTQSPDSLAVSLGERATINCKSSQTVLYPLNNRNYLAWYQQKPGQPPKLLINQASTRASGVPDRFSGSGSGTEF
TLIISSLQAEDVAIYYCQQYYTPPLAFGGGTKLEIK

>CD47-13H3
VH

SEQ ID NO.: 31

KVQLVESGGGLVKPGGSLRLSCAASGLTFERAWMNWVRQAPGKGLEWVGRIKRKTDGETTDYAAPVKGRFSISRDDS
KNTLYLQMNSLKTEDTAVYYCAGSNRAFDIWGQGTMVTVSA
VL

SEQ. ID NO.: 32

DIVMTQSPDSLAVSLGERATINCKSSQSVLYAGNNRNYLAWYQQKPGQPPKLLINQASTRASGVPDRFSGSGSGTEF
TLIISSLQAEDVAIYYCQQYYTPPLAFGGGTKLEIK

>CD47-14A8
VH

SEQ ID NO.: 33

KVQLVESGGGLVKPGGSLRLSCAASGFTFPNAWMNWVRQAPGKGLEWVGRIKRKTDGETTDYAAPVKGRFSISRDDS
KNTLYLQMNSLKTEDTAVYYCAGSNRAFDIWGQGTMVTVSA
VL

SEQ. ID NO.: 34

DIVMTQSPDSLAVSLGERATINCKSSQSVLYPGNNRNYLAWYQQKPGQPPKLLINQASTRASGVPDRFSGSGSGTEF
TLIISSLQAEDVAIYYCQQYYTPPLAFGGGTKLEIK

>CD47-16H3
VH

SEQ ID NO.: 35

KVQLVESGGGLVKPGGSLRLSCAASGLTFGNAWMNWVRQAPGKGLEWVGRIKRKTDGETTDYAAPVKGRFSISRDDS
KNTLYLQMNSLKTEDTAVYYCAGSNRAFDIWGQGTMVTVSA
VL

SEQ. ID NO.: 36

DIVMTQSPDSLAVSLGERATINCKSSQSVLYPGNNRNYLAWYQQKPGQPPKLLINQASTRASGVPDRFSGSGSGTEF
TLIISSLQAEDVAIYYCQQYYTPPLAFGGGTKLEIK

SEQ ID NO.: 37

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGGNHSSDIWGQGTMVTVSA

VL

SEQ. ID NO.: 38

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-1A1-A
VH

SEQ ID NO.: 39

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGGAHSSDIWGQGTMVTVSA

VL

SEQ. ID NO.: 40

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-1A1-Q
VH

SEQ ID NO.: 41

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGGQHSSDIWGQGTMVTVSA

VL

SEQ. ID NO.: 42

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-1A2
VH

SEQ ID NO.: 43

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSAYAFDAWGQGTMVTVSA

VL

SEQ. ID NO.: 44

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

SEQ ID NO.: 45

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSAYAFDSWGQGTMVTVSA

VL

SEQ. ID NO.: 46

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-1B1
VH

SEQ ID NO.: 47

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSDRASDKWGQGTMVTVSA

SEQ. ID NO.: 48

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-1B2
VH

SEQ ID NO.: 49

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSAYAFDTWGQGTMVTVSA

VL

SEQ. ID NO.: 50

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-1H3
VH

SEQ ID NO.: 51

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGGNHSQDIWGQGTMVTVSA

VL

SEQ. ID NO.: 52

Fig. 26G

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-1H3-Q
VH

SEQ ID NO.: 53

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGGQHSQDIWGQGTMVTVSA
VL

SEQ. ID NO.: 54

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-1H3-A
VH

SEQ ID NO.: 55

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGGAHSQDIWGQGTMVTVSA
VL

SEQ. ID NO.: 56

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYYTPPLAFGGGTKLEIK

>CD47-2A2
VH

SEQ ID NO.: 57

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA
VL

SEQ. ID NO.: 58

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYLTPPLAFGGGTKLEIK

>CD47-2A3
VH

SEQ ID NO.: 59

Fig. 26H

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

VL

SEQ. ID NO.: 60

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYLRPPLNFGGGTKLEIK

>CD47-2A6

VH

SEQ ID NO.: 61

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

VL

SEQ. ID NO.: 62

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYLTPPLNFGGGTKLEIK

>CD47-2A10

VH

SEQ ID NO.: 63

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

VL

SEQ. ID NO.: 64

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQNYLTPPLSFGGGTKLEIK

>CD47-2B1

VH

SEQ ID NO.: 65

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

VL

SEQ. ID NO.: 66

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYLKAPLAFGGGTKLEIK

SEQ ID NO.: 67

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

VL

SEQ. ID NO.: 68

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYLNAPLHFGGGTKLEIK

>CD47-2E7
VH

SEQ ID NO.: 69

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

VL

SEQ. ID NO.: 70

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYLEAPLVFGGGTKLEIK

>CD47-2E9
VH

SEQ ID NO.: 71

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

VL

SEQ. ID NO.: 72

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQQYLKAPLHFGGGTKLEIK

>CD47-2F1
VH

SEQ ID NO.: 73

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA

SEQ. ID NO.: 74

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQRLIAPPFTFGGGTKLEIK

>CD47-2F3
VH

SEQ ID NO.: 75

KVQLVESGGGLVKPGGSLRLSCAASGFTFSNAWMNWVRQAPGKGLEWVGRIKRKTDGETTDYAAPVKGRFSISRDDS
KNTLYLQMNSLKTEDTAVYYCAGSNRAFDIWGQGTMVTVSA
VL

SEQ. ID NO.: 76

DIVMTQSPDSLAVSLGERATINCKSSQSVLYSSNNRNYLAWYQQKPGQPPKLLINQASTRASGVPDRFSGSGSGTEF
TLIISSLQAEDVAIYYCQNYLTPPLAFGGGTKLEIK

>CD47-34C5
VH

SEQ. ID NO.: 77

CAGGTCCAACTGGTGCAGTCTGGGGCTGAAGTGAAGAAGCCTGGGTCTTCAGTGAAGGTGTCCTGCAAGGCTTCTGG
CTACACCTTCAGCAGCTACTATATGCACTGGGTGAGGCAGGCTCCTGGACAAGGCCTTGAGTGGATGGGAGAGATTA
ATCCCAACAATGCCCGTATTAACTTCAATGAAAAGTTCAAGACCAGGGTCACACTCACTGTGGACAAATCCACCAGC
ACAGCATACATGGAGCTCAGCAGCCTGAGATCTGAGGACACCGCGGTCTATTACTGTACCAGAGGATACTATAGGTA
CGGGGCCTGGTTTGGTTACTGGGGCCAAGGGACTCTGGTCACTGTCTCTTCA

>CD47-34C5
VL

SEQ. ID NO.: 78

GATATCCAGATGACACAGTCTCCATCCTCCCTGTCTGCCTCTGTGGGAGACAGAGTCACCATCACTTGCAGGGCAAG
TCAGGACATTAGCGATTATTTGAACTGGTATCAACAGAAACCAGGCAAGGCTCCTAAACTCCTGATCTACTACATAT
CAAGATTACACTCAGGAGTCCCATCACGCTTCAGTGGCAGTGGGTCTGGAACAGATTATACTCTCACCATTAGCTCC
CTGCAGCCAGAAGATTTTGCCACTTACTATTGCCAACAGGGTCATACACTTCCGTGGACCTTCGGTGGAGGCACCAA
GGTGGAAATCAAA

NUCLEOTIDE SEQUENCES OF VH:

>CD47-1A1_VH

SEQ ID NO.: 79

Fig. 26K

CAGGTACAGCTGCAGCAGTCAGGGGGAGGCTTGGTACAGCCTGGGGGGTCCCTAAGACTCTCCTGTACAGCCTCTGG
ATTCACCTTTAGCAGCTATGCCATGAGCTGGGTCCGCCAGGCTCCAGGGAAGGGGCTGGAGTGGGTCTCAGCAATTA
GTGGTAGTGGTGGTAGCACATACTACGCAGACTCCGTGAAGGGCCGGTTCACCATCTCCAGAGACAATTCCAAGAAC
ACGCTGTATCTGCAAATGAACAGCCTGAGAGTCGAGGACACGGCCGTATATTACTGTGCGAGATATAGTATTGGTAG
ACACACCTTTGACCACTGGGGCCAGGGCACCCTGGTCACCGTCTCGGCC

>CD47-1F8_VH

SEQ ID NO.: 80

AAGGTGCAGCTGGTGGAGTCTGGGGGAGGCTTGGTAAAGCCTGGGGGGTCCCTTAGACTCTCCTGTGCAGCCTCTGG
TTTCACTTTCAGTAACGCCTGGATGAACTGGGTCCGCCAGGCTCCAGGGAAGGGGCTGGAGTGGGTCGGCCGTATTA
AAGGAAAACTGATGGTGAGACAACAGACTACGCTGCACCCGTGAAAGGCAGATTCAGCATCTCAAGAGATGATTCA
AAAAACACCCTGTATCTGCAAATGAACAGCTTGAAAACCGAGGACACAGCCGTGTATTACTGCGCTGGCAGTAACCG
AGCTTTTGATATCTGGGGCCAAGGGACAATGGTCACCGTCTCTGCC

>CD47-2A11_VH

SEQ ID NO.: 81

CAGGTACAGCTGCAGCAGTCAGGGGGAGGCTTGGTACAGCCTGGGGGGTCCCTGAGACTCTCCTGTGCAGCCTCTGG
ATTCACCTTTAGCGGCTATGCCATGACTTGGGTCCGCCAGGCTCCAGGGAAGGGGCTGGAGTGGGTCTCAGCTATTA
CTTCTACTGGTGGTCGCACATACTACGCAGACTCCGTGAAGGGCCGGTTCACCACCTCCAGAGACAATTCCAGGAAC
ACGTTGTATCTGCAAATGAACAGCCTGAGAGCCGAAGACACGGCCGTATATTACTGTGCGAGAGAGTCAAACTTCAG
GGCTTTTGATATCTGGGGCCAAGGGACAATGGTCACCGTCTCTGCC

>CD47-2C2_VH

SEQ ID NO.: 82

GAGGTGCAGCTGGTGGAGTCTGGGGGAGGCTTGGTACAGCCTGGGGGGTCCCTTAGACTCTCCTGTGCAGCCTCTGG
ATTCACTTTCATTGACGCCTGGATGACCTGGGTCCGCCAGGCTCCAGGGAAGGGGCTGGAGTGGGTCTCAGTTATTT
ATAGCGGTGGTAGCACATACTACGCAGACTCCGTGAAGGGCAGATTCACCATCTCCAGAGACAATTCCAAGAACACG
CTGTATCTGCAAATGAACAGCCTGAGAGCCGAGGACACGGCCGTATATTACTGTGCGAGAGGGGCTAGGGGCCATCC
CGGGCAGGACTACTGGGGCAGGGCACCCTGGTCACCGTCTCGGCC

>CD47-2D7_VH

SEQ ID NO.: 83

CAGGTCAACTTAAGGGAGTCTGGGGGAGGCTTGGTACAGCCTGGCGGGTCCCTGAGACTCTCCTGTGCAGCCTCTGG
ATTCACCTTCAGTGACTACTACATGAGCTGGATCCGCCAGGCTCCAGGGGGGGGCTGGAGTGGGTTTCATACACTA
GTCGTTTTGGTAGTGACACAAACTACGCAGACTCTGTGAAGGGCCGATTCACCATCTCCAGAGACAACGTCCAGAAC

Fig. 26L

TCACTATATCTGCAAATGAACAGCCTGAGGGCCGAGGACACGGCTGTTTATTACTGTGTGAGAGATGTACATAACAG
GGATGCCTACTGGGGCCAGGGCACCCTGGTCACCGTCTCGGCC

>CD47-2G4_VH

SEQ ID NO.: 84

CAGGTGCAGCTGGTGCAGTCTGGGGGAGGCTTGGTACAGCCTGGGGGGTCCCTGAGACTCTCCTGTGCAGCCTCTGG
ATTCACCTTTAGCAGCTATGCCATGAGCTGGGTCCGCCAGGCTCCAGGGAAGGGGCTGGAGTGGGTCTCAGCTATTA
GTGGTAGTGGTGGTAGCACATACTACGCAGACTCCGTGAAGGGCCGGTTCACCATCTCCAGAGACAATTCCAAGAAC
ACGCTGTATCTGCAAATGAACAGCCTGAGAGCCGAGGACACGGCCGTATATTACTGTGCGAACACAGATTACTATGA
TAGTAGTAGCCATACCCCCGCTGACTACTGGGGCCAGGGCACCCTGGTCACCGTCTCGGCC

>CD47-2G11_VH

SEQ ID NO.: 85

CAGGTGCAGCTGCAGGAGTCGGGGGGAGGCTTGGTACAGCCTGGGGGGTCCCTGAGACTCTCCTGTGCAGCCTCTGG
ATTCACCTTTAGTAGCTATGGCATGAGCTGGGTCCGCCAGGCTCCAGGGAAAGGGCTGGAGTGGGTCTCAACTATCA
GTGGCAGTGGTAGTAGCACAAACTACGCAGACTCCGTGAAGGGCCGGTTCACCATCTCCAGAGACAATTCCAAGAAC
ACGCTATTTCTGCAAATGAACAGCCTGAGAGCCGAGGACACGGCCGTATATTTCTGTGCGAAAGGCCGATATTACTA
TGATAGTCTTGATGCTTTTGATATCTGGGGCCAAGGGACAATGGTCACCGTCTCTGCC

>CD47-6F4_VH

SEQ ID NO.: 86

CAGGTACAGCTGGTGGAGTCTGGGGGAGGCTTGGTACAGCCTGGGGGGTCCCTGAGACTCTCCTGTGCAGCCTCTGG
ATTCACCTTTAGCAGCTATGCCATGAGCTGGGTCCGCCAGGCTCCAGGGAAGGGGCTGGAGTGGGTCTCAGCTATTA
GTGGTACTGGTGGTAGCACATACTACGCAGACTCCGTGAAGGGCCGGTTCACCATCTCCAGAGACAATTCCAAGAAC
ACGCTGTATCTGCAAATGAACAGCCTGAGAGCCGAGGACACGGCCGCATATTACTGTGCGAAAGATAAATGGAGCAG
CTGGCCCACTTACTACTTTGACTACTGGGGCCAGGGAACCCTGGTCACCGTCTCGGCC

>CD47-5H1_VH

SEQ ID NO.: 87

CAGGTGCAGCTGCAGGTGTCGGGGGGAGGCTTGGTACAGCCTGGGGGGTCCCTGAGACTCTCCTGTGCAGCCTCTGG
ATTCACCTTCAGTAGCTATAGCATGGCCTGGGTCCGCCAGGCTCCAGGGAAGGGGCTGGAGTGGGTCGCGGCTGTTA
GTAATAGTGGTGTTGAGACATACTACGCAGACTCCGTGAAGGGCCGGTTCACCATCTCCAGAGACAATTCCAAGAAC
ACGCTGTATTTGCAAATGAACAGCCTGAGAGCCGAGGACACGGCCGTATATTACTGTGCGAAACGAACTAGACAACT
GCTAACTCCGCGGGAGTTTGACTACTGGGGCCAGGGCACCCTGGTCACCGTCTTGGCC

>CD47-5F6_VH

SEQ ID NO.: 88

Fig. 26M

CAGGTCAACTTAAGGGAGTCTGGGGGAGGCTTGATACAGCCTGGGGGGTCCCTGAGACTCTCCTGTGCAGCCTCTGG
ATTCACCTTTACCAATTATGCCATGAGCTGGGTCCGCCAGGCTCCAGGGAAGGGGCTGGAGTGGGTCTCAAGTGTTA
GTAGTGCTGGTGGTAGTACATACTACGCAGACTCCGTGAAGGGCCGGTTCACCATCTCCAGAGACAACGCCAAGAAC
TCACTGTATCTGCAAATGAACAGCCTGAGAGCCGAGGACACGGCTGTTTATTACTGTGCGAGACGAGTCAATCGGGC
CTTCGATCTCTGGGGCCGTGGAACCCTGGTCACCGTCTCGGCC

>CD47-1F3_VH

SEQ ID NO.: 89

CAGGTGCAGCTGCAGGAGTCGGGGGGAGGCTTGGTACAGCCTGGGGGGTCCCTTAGACTCTCCTGTGCAGCCTCTGG
ATTCACTTTCAGTAACGCCTGGATGAGCTGGGTCCGCCAGGCTCCAGGGAAGGGGCTGGTGTGGGTTGGCCGTATTA
AAAGCAAAACTGATGGTGGGACAACAGACTACGCTGCACCCGTGAAAGGCAGATTCACCATCTCAAGAGATGATTCA
AAAAACACGCTGTATCTGCAAATGAACAGCCTGAAAACCGAGGACACAGCCGTGTATTACTGTACCACAGATAAGAG
CTATGGTTACACATTTGACTACTGGGGCCAGGGCACCCTGGTCACCGTCTCGGCC

>CD47-2A4_VH

SEQ ID NO.: 90

CAGGTCAACTTAAGGGAGTCTGGGGGAGGCTTGGTAAAGCCGGGGGGGTCCCTTAGACTCTCCTGTGCAGCCTCTGG
ATTCACCTTCAGTAGCTACTGGATGCACTGGGTCCGCCAAGCCCCAGGGAAGGGGCTGGAGTGGGTCTCAGCTATCA
GTGGTAGTGGTGCCGGCACATACTACCCAGACTCCGTGAAGGGCCGGTTCACCATCTCCAGAGACAATTCCAAGAAC
ACGCTGTATCTGCAAATGAACAGCCTGAGAGCCGAGGACACGGCCGTATATTACTGTGCGAGAGATCGGTCCTTATC
TTTTGGTTTTGATATTTGGGGCCAAGGCACCCTGGTCTCCGTCTCTGGC

>CD47-2B12_VH

SEQ ID NO.: 91

CAGGTACAGCTGCAGCAGTCAGGGGGAGGCTTGGTCCAGCCGGGGGGGTCACTGAGACTCTCCTGTGCAGCCCCTGG
ATTCACCTTTAGTAGATATTGGATGAGTTGGGTCCGCCAGGCTCCAGGGAAGGGACTGGAGTGGGTGGCCAACATAA
AGGGAGATGGAAGTCAGACATACTATGCGGACTCTGTGAAGGGCCGATTCACCATCTCCAGAGACAACGCCATGAAA
ACAGTGTATCTGCAAATGAACAGCCTGAGAGCCGAGGACACGGCCATATATTACTGTGCGAAAGGGGCTGCTTATCA
CATTAACAGCTGGCTCGACCCCTGGGGCCAGGGCACCCTGGTCACCGTCTCGGCC

NUCLEOTIDE SEQUENCES OF VL:

>CD47-1A1_VL

SEQ ID NO.: 92

AATTTTATGCTGACTCAGCCCCACTCTGTGTCGGAGTCTCCGGGGAAGACGGTAACCATCTCCTGCACCCGCAGCAG
TGGCGGCATTGCCAGTAACTTTGTGCAGTGGTACCAGCAGCGCCCGGGCAGTGTCCCCACCACTGTGATCTATAGGG
ATAACCAAAGACCCTCTGGAGTCCCTGATCGGTTCTCTGGCTCCGTCGACAGCTCCTCCAATTCTGCCTCCCTCACC

Fig. 26N

ATCTCTGGGCTGAAGACTGACGATGAGGCTGACTATTATTGTCAGTCCTATGATGACCACAATCATTGGGTGTTCGG
CGGCGGGACCAAGCTGACCGTCCTA

>CD47-1F8_VL

SEQ ID NO.: 93

GACATCGTGATGACCCAGTCTCCAGACTCCCTGGCTGTGTCTCTGGGCGAGAGGGCCACCATCAACTGCAAGTCCAG
CCAGAGTGTTTTATACAGCTCCAACAATAGGAACTACCTAGCTTGGTACCAGCAGAAACCAGGACAGCCTCCTAAGC
TGCTCATTAACCAGGCATCTACCCGGGCATCCGGCGTCCCTGACCGATTCAGTGGCAGCGGGTCTGGGACAGAGTTC
ACTCTCATCATCAGCAGCCTGCAGGCTGAAGATGTGGCGATTTATTACTGTCAGCAATATTATACTCCTCCCCTCGC
TTTCGGCGGAGGGACCAAGCTGGAGATCAAA

>CD47-2A11_VL

SEQ ID NO.: 94

GAAATTGTGTTGACGCAGTCTCCACTCTCCCTGCCCGTCACCCCTGGAGAGCCGGCCTCCATCTCCTGCAGGTCTAG
TCAGAGCCTCCTGCACAGTAATGGATACAACTATTTGGATTGGTACCTGCAGAAACCAGGGCAGTCTCCACAGCTCC
TGATCTATTTGAATTCTAATCGGGCCTCCGGGGTCCCTGACAGGTTCAGTGGCAGTGGATCAGGTACAGATTTTACA
CTGCAAATCAGCAGAGTGGAGGCTGAGGATGTTGGGGTTTACTACTGTATGCAAGCTCTACAAATTCCTCCCACTTT
CGGCGGAGGGACCAAAGTGGATATCAAA

>CD47-2C2_VL

SEQ ID NO.: 95

AATTTTATGCTGACTCAGCCCCACTCTGTGTCGGAGTCTCCGGGAAAGACGGTAACCATCTCCTGCACCCGCAGCAG
TGGCACCATTGCCAGCAACTTTGTGCAGTGGTATCAACAGCGCCCGGGCAGTTCGCCCACCCCAGTGATCTTTGAGA
ATGACCGAAGACCCTCTGGGGTCCCTGATCGGTTCTCTGGCTCCATCGACAGCTCCTCCAATTCTGCCTCCCTCACC
ATTTCGTCACTGAACACTGAGGACAAGGCTGACTACTACTGTCAGTCCTATGATAGCAGCACTCATGGGTGGGTGTT
TGGCGGAGGGACCCAGCTCACCGTTTTA

>CD47-2D7_VL

SEQ ID NO.: 96

TCCTATGTGCTGACTCAGCCACCCTCAGCGTCTGGGACCCCGGGCAGAGGGTCACCATCTCTTGTTCTGGAAGCAG
CTCCAACATCGGCGGTAATTCTGTATCCTGGTACCAGCAACTCCCAGGAACGGCCCCCAAGCTCCTCATCTATAGGA
ATCATCAGCGGCCCTCAGGGGTCCCTGACCGATTCTCTGGCTCCAAGTCTGGCACCTCAGCCTCCCTGGCCATCAGT
GGGCTCCGGTCCGACGACGAGGCTGATTATTATTGTGCAACATGGGATTTCAGCCTGAGTGGTTTTGTCTTCGGAAC
TGGGACCAAGGTCACCGTCCTA

>CD47-2G4_VL

SEQ ID NO.: 97

Fig. 26O

GAAACTACACTCACGCAGTCTCCATCCTCCCTGTCTGCATCTGTAGGAGACAGAGTCACCATCACTTGCCGGGCCAG
TCAGGACATCAGAAATGATTTAGACTGGTTTCAACAAAAACCAGGCGAAGCCCCTAAACGCCTGATCTCTGCTGCAT
CTAATTTGCAGAGTGGGGTCCCCTCACGATTCAGCGGCGGTGGCTCTGGCTCCGAATTCACTCTCACAATCCACAGC
CTGGAGTCTGAAGATTTTGCAACTTACTACTGTCAACAGAGTTACATTACCCCTCCTTGGACGTTCGGCCAAGGGAC
CAAGCTGGAGATCAAA

>CD47-2G11_VL

SEQ ID NO.: 98

GAAATTGTGTTGACGCAGTCTCCAGGCACCCTGTCTTTGTCTCCAGGGGAAAGAGCCACCCTCTCCTGCAGGGCCAG
TCAGGAAATTAGGACCGCCTACTTAGCCTGGTACCAGCAGAAACCTGGCCAGGCTCCCAGGCTCCTCATCTATTATG
CATCCAGCAGGGCCACTGGCATCCCAGACAGGTTCAGCGGCAGTAGGTCTGGGACAGACTTCACTCTCACCATCAGC
AGACTGGAGCCTGAAGATTTTGCAGTGTATTCCTGTCAGCAGTATGATACCTCACCTCCCACCTTCGGCCAAGGGAC
ACGACTGGAGATTAAA

>CD47-6F4_VL

SEQ ID NO.: 99

AATTTTATGCTGACTCAGCCCCACTCTGTGTCGGAGTCTCCGGGGAAGACGGTAACCATCTCCTGCACCCGCAGCAG
TGGCAGCATTGCCAGCAACTATGTGCAGTGGTACCAACAGCGCCCGGGCAGTTCCCCCACCACTGTGATCTATGAGG
ATAACCAAAGACCCTCTGGGGTCCCTGATCGGTTCTCTGGCTCCATCGACAGCTCCTCCAACTCTGCCTCCCTCACC
ATCTCTGGACTGAAGACTGAGGACGAGGCTGACTACTACTGTCAGTCTTATGATAGCAGCAATGTGATATTCGGCGG
AGGGACCAAGGTCACCGTCCTA

>CD47-5H1_VL

SEQ ID NO.: 100

GAAACTACACTCACGCAGTCTCCATCTTCCGTGTCTGCATCTGTAGGAGACAGAGTCACCCTCACTTGTCGGGCGAG
TCAGGATATCACAAGGTGGTTAGCCTGGTATCAGCAGAAACCAGGGAAAGCCCCTAAGCTCCTGATCTATGATGCAT
CCAGTTTGCAAAGTGGGGTCCCATCAAGATTCAGCGGCAGTGGATCTGGGACAGATTTCACTCTCACCATCAGCAGT
CTGCAACCTGAAGATTTTGCAACTTACTACTGTCAACAGGGTTCCAGTGTTCCTTTCACTTTCGGCGGAGGGACCAA
GGTGGAGATCAAA

>CD47-5F6_VL

SEQ ID NO.: 101

GATGTTGTGATGACTCAGTCTCCAGGCACCCTGTCTTTGTCTCCAGGGGAAAGAGCCACCCTCTCCTGCAGGGCCAG
TCAGAGTGTTAGCAGCAGCTACTTAGCCTGGTACCAACAGAAACCTGGCCAGGCTCCCAGGCTCCTCATCTATGGTG
CATCCAGCAGGGCCACTGGCATCCCAGACAGGTTCAGTGGCAGTGGGTCTGGGACAGACTTCACTCTCACCATCAGC
AGACTGGAGCCTGAAGATTTTGCAGTGTATTACTGTCAGCAGTATGGTAGCTCACCTCCTATGTACACTTTTGGCCA

Fig. 26P

GGGGACCAAGCTGGAGATCAAA

>CD47-1F3_VL

SEQ ID NO.: 102

TCCTATGTGCTGACTCAGCCACCCTCAGCGTCTGGGACCCCCGGGCAGAGGGTCACCATCTCTTGTTCTGGAAGTGG
CTCCAACATCGGAAGTAATTCTGTTCACTGGTACCAGCAACTCCCAGGAACGGCCCCCAAACTCCTCATCTATACTA
ATAATCAGCGGCCCTCAGGGGTCCCTGACCGATTCTCTGGCTCCAAGTCTGGCATTTCAGCCTCCCTGGCTATCAGT
GGGCTCCAGTCTGAGGATGAGGCTGTTTATTACTGTGCAACGTGGGATGACAGACTGAGTGGTCCGGTGTTCGCCGC
AGGGACCAAGCTGACCGTCCTA

>CD47-2A4_VL

SEQ ID NO.: 103

AATTTTATGCTGACTCAGCCCCACTCTGTGTCGGGGTCTCCGGGGAAGACGGTAACCATCTCCTGCACCCGCAGCAG
TGGCAGCATTGGCAGCACCTATGTGCAGTGGTACCAACAGCGCCCGGGCAGTCCCCCCACCACTGTGATCTATAAGG
ATGACCAAAGACCCTCTGGGGTCCCTGATCGGTTCTCTGGCTCCATCGACGGCTCCTCCAACTCTGCCTCCCTCACC
ATCTCTGGACTGGAGACTGAGGACGAGGCTGACTACTACTGTCAGTCTTCTGATACCAGCAATCTGGTCTTCGGCGG
AGGGACCAAGGTCACCGTCCTA

>CD47-2B12_VL

SEQ ID NO.: 104

GAAACTACACTCACGCAGTCTCCAGGCACCCTGTCTGTTTCTCCGGGGGAAAGAGTTACCCTCTCCTGCAGGGCCAG
TCAGAGTATTAGCGGTAATTACTTAGCCTGGTACCAGCAGAGACCTGGCCAGGCTCCCAGGCTCCTCATCTATGGGG
CATTCAGGAGGGCCACTGGCATCCCAGACAGGTTCAGTGGCAGTGGGTCTGGGACAGACTTCACTCTCACCATCACC
AGACTGGAGCCTGAAGATTTTGCAACTTATTACTGCCAACACTATAATAATTTCCCCCACACTTTCGGCGCAGGGAC
CAAAGTGGATATCAAA

>CD47-34C5_VH

SEQ ID NO.: 105

QVQLVQSGAEVKKPGSSVKVSCKASGYTFSSYYMHWVRQAPGQGLEWMGEINPNNARINFNEKFKTRVTLTVDKSTS
TAYMELSSLRSEDTAVYYCTRGYYRYGAWFGYWGQGTLVTVSS

>CD47-34C5_VL

SEQ ID NO.: 106

DIQMTQSPSSLSASVGDRVTITCRASQDISDYLNWYQQKPGKAPKLLIYYISRLHSGVPSRFSGSGSGTDYTLTISS
LQPEDFATYYCQQGHTLPWTFGGGTKVEIK

SEQ ID NO.: 107

QLLFNKTKSVEF TFCNDTVVIP CFVTNMEAQN TTEVYVKWKF KGRDIYTFDG
ALNKSTVPTD FSSAKIEVSQ LLKGDASLKM DKSDAVSHTG NYTCEVTELT
REGETIIELK YRVVSWFSPNE

Fig. 27

SEQUENCE LISTING

```
<160> NUMBER OF SEQ ID NOS: 113

<210> SEQ ID NO 1
<211> LENGTH: 119
<212> TYPE: PRT
<213> ORGANISM: Homo sapiens

<400> SEQUENCE: 1

Gln Val Gln Leu Gln Gln Ser Gly Gly Leu Val Gln Pro Gly Gly
1               5                   10                  15

Ser Leu Arg Leu Ser Cys Thr Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Tyr Ser Ile Gly Arg His Thr Phe Asp His Trp Gly Gln Gly
                100                 105                 110

Thr Leu Val Thr Val Ser Ala
            115

<210> SEQ ID NO 2
<211> LENGTH: 111
<212> TYPE: PRT
<213> ORGANISM: Homo sapiens

<400> SEQUENCE: 2

Asn Phe Met Leu Thr Gln Pro His Ser Val Ser Glu Ser Pro Gly Lys
1               5                   10                  15

Thr Val Thr Ile Ser Cys Thr Arg Ser Ser Gly Gly Ile Ala Ser Asn
                20                  25                  30

Phe Val Gln Trp Tyr Gln Gln Arg Pro Gly Ser Val Pro Thr Thr Val
            35                  40                  45

Ile Tyr Arg Asp Asn Gln Arg Pro Ser Gly Val Pro Asp Arg Phe Ser
        50                  55                  60

Gly Ser Val Asp Ser Ser Ser Asn Ser Ala Ser Leu Thr Ile Ser Gly
65                  70                  75                  80

Leu Lys Thr Asp Asp Glu Ala Asp Tyr Tyr Cys Gln Ser Tyr Asp Asp
                85                  90                  95

His Asn His Trp Val Phe Gly Gly Gly Thr Lys Leu Thr Val Leu
                100                 105                 110

<210> SEQ ID NO 3
<211> LENGTH: 118
```

```
<212> TYPE: PRT
<213> ORGANISM: Homo sapiens

<400> SEQUENCE: 3

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 4
<211> LENGTH: 113
<212> TYPE: PRT
<213> ORGANISM: Homo sapiens

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu His Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 5
<211> LENGTH: 118
<212> TYPE: PRT
<213> ORGANISM: Homo sapiens

<400> SEQUENCE: 5

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Thr Trp Val Arg Gln Ala Pro Gly Lys Gly Leu Glu Trp Val
        35                  40                  45

Ser Ala Ile Thr Ser Thr Gly Gly Arg Thr Tyr Tyr Ala Asp Ser Val
    50                  55                  60
```

```
Lys Gly Arg Phe Thr Thr Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ser Asn Phe Arg Ala Phe Asp Ile Trp Gly Gln Gly Thr
            100                 105                 110

Met Val Thr Val Ser Ala
        115

<210> SEQ ID NO 6
<211> LENGTH: 112
<212> TYPE: PRT
<213> ORGANISM: Homo sapiens

<400> SEQUENCE: 6

Glu Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Asn Ser Asn Arg Ala Ser Gly Val Pro
     50                  55                  60

Asp Arg Phe Ser Gly Ser Gly Ser Gly Thr Asp Phe Thr Leu Gln Ile
 65                  70                  75                  80

Ser Arg Val Glu Ala Glu Asp Val Gly Val Tyr Tyr Cys Met Gln Ala
                 85                  90                  95

Leu Gln Ile Pro Pro Thr Phe Gly Gly Gly Thr Lys Val Asp Ile Lys
            100                 105                 110

<210> SEQ ID NO 7
<211> LENGTH: 118
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ile Asp Ala
             20                  25                  30

Trp Met Thr Trp Val Arg Gln Ala Pro Gly Lys Gly Leu Glu Trp Val
         35                  40                  45

Ser Val Ile Tyr Ser Gly Gly Ser Thr Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Ala Arg Gly His Pro Gly Gln Asp Tyr Trp Gly Gln Gly Thr
            100                 105                 110

Leu Val Thr Val Ser Ala
        115

<210> SEQ ID NO 8
<211> LENGTH: 112
<212> TYPE: PRT
<213> ORGANISM: Homo sapiens
```

<400> SEQUENCE: 8

Asn Phe Met Leu Thr Gln Pro His Ser Val Ser Glu Ser Pro Gly Lys
1               5                   10                  15

Thr Val Thr Ile Ser Cys Thr Arg Ser Ser Gly Thr Ile Ala Ser Asn
            20                  25                  30

Phe Val Gln Trp Tyr Gln Gln Arg Pro Gly Ser Ser Pro Thr Pro Val
        35                  40                  45

Ile Phe Glu Asn Asp Arg Arg Pro Ser Gly Val Pro Asp Arg Phe Ser
50                  55                  60

Gly Ser Ile Asp Ser Ser Asn Ser Ala Ser Leu Thr Ile Ser Ser
65                  70                  75                  80

Leu Asn Thr Glu Asp Lys Ala Asp Tyr Tyr Cys Gln Ser Tyr Asp Ser
                85                  90                  95

Ser Thr His Gly Trp Val Phe Gly Gly Gly Thr Gln Leu Thr Val Leu
            100                 105                 110

<210> SEQ ID NO 9
<211> LENGTH: 117
<212> TYPE: PRT
<213> ORGANISM: Homo sapiens

<400> SEQUENCE: 9

Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Gly Gly Leu Glu Trp Val
        35                  40                  45

Ser Tyr Thr Ser Arg Phe Gly Ser Asp Thr Asn Tyr Ala Asp Ser Val
50                  55                  60

Lys Gly Arg Phe Thr Ile Ser Arg Asp Asn Val Gln Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Val His Asn Arg Asp Ala Tyr Trp Gly Gln Gly Thr Leu
            100                 105                 110

Val Thr Val Ser Ala
        115

<210> SEQ ID NO 10
<211> LENGTH: 110
<212> TYPE: PRT
<213> ORGANISM: Homo sapiens

<400> SEQUENCE: 10

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Ser Val Ser Trp Tyr Gln Gln Leu Pro Gly Thr Ala Pro Lys Leu Leu
        35                  40                  45

Ile Tyr Arg Asn His Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Asp Asp Glu Ala Asp Tyr Tyr Cys Ala Thr Trp Asp Phe Ser Leu
                85                  90                  95

Ser Gly Phe Val Phe Gly Thr Gly Thr Lys Val Thr Val Leu
            100                 105                 110

<210> SEQ ID NO 11
<211> LENGTH: 108
<212> TYPE: PRT
<213> ORGANISM: Homo sapiens

<400> SEQUENCE: 11

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Tyr Tyr
65                  70                  75                  80

Cys Ala Asn Thr Asp Tyr Tyr Asp Ser Ser His Thr Pro Ala Asp
                85                  90                  95

Tyr Trp Gly Gln Gly Thr Leu Val Thr Val Ser Ala
            100                 105

<210> SEQ ID NO 12
<211> LENGTH: 108
<212> TYPE: PRT
<213> ORGANISM: Homo sapiens

<400> SEQUENCE: 12

Glu Thr Thr Leu Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Asp Trp Phe Gln Gln Lys Pro Gly Glu Ala Pro Lys Arg Leu Ile
        35                  40                  45

Ser Ala Ala Ser Asn Leu Gln Ser Gly Val Pro Ser Arg Phe Ser Gly
    50                  55                  60

Gly Gly Ser Gly Ser Glu Phe Thr Leu Thr Ile His Ser Leu Glu Ser
65                  70                  75                  80

Glu Asp Phe Ala Thr Tyr Tyr Cys Gln Gln Ser Tyr Ile Thr Pro Pro
                85                  90                  95

Trp Thr Phe Gly Gln Gly Thr Lys Leu Glu Ile Lys
            100                 105

<210> SEQ ID NO 13
<211> LENGTH: 122
<212> TYPE: PRT
<213> ORGANISM: Homo sapiens

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

-continued

Gly Met Ser Trp Val Arg Gln Ala Pro Gly Lys Gly Leu Glu Trp Val
            35                  40                  45

Ser Thr Ile Ser Gly Ser Gly Ser Thr Asn Tyr Ala Asp Ser Val
 50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Phe Cys
                85                  90                  95

Ala Lys Gly Arg Tyr Tyr Tyr Asp Ser Leu Asp Ala Phe Asp Ile Trp
                100                 105                 110

Gly Gln Gly Thr Met Val Thr Val Ser Ala
                115                 120

<210> SEQ ID NO 14
<211> LENGTH: 108
<212> TYPE: PRT
<213> ORGANISM: Homo sapiens

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Glu Ile Arg Thr Ala
                20                  25                  30

Tyr Leu Ala Trp Tyr Gln Gln Lys Pro Gly Gln Ala Pro Arg Leu Leu
            35                  40                  45

Ile Tyr Tyr Ala Ser Ser Arg Ala Thr Gly Ile Pro Asp Arg Phe Ser
 50                  55                  60

Gly Ser Arg Ser Gly Thr Asp Phe Thr Leu Thr Ile Ser Arg Leu Glu
65                  70                  75                  80

Pro Glu Asp Phe Ala Val Tyr Ser Cys Gln Gln Tyr Asp Thr Ser Pro
                85                  90                  95

Pro Thr Phe Gly Gln Gly Thr Arg Leu Glu Ile Lys
                100                 105

<210> SEQ ID NO 15
<211> LENGTH: 122
<212> TYPE: PRT
<213> ORGANISM: Homo sapiens

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Thr Gly Gly Ser Thr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Asp Lys Trp Ser Ser Trp Pro Thr Tyr Tyr Phe Asp Tyr Trp
                100                 105                 110

Gly Gln Gly Thr Leu Val Thr Val Ser Ala
                115                 120

```
<210> SEQ ID NO 16
<211> LENGTH: 110
<212> TYPE: PRT
<213> ORGANISM: Homo sapiens

<400> SEQUENCE: 16

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Ile Phe Gly Gly Gly Thr Lys Val Thr Val Leu
            100                 105                 110

<210> SEQ ID NO 17
<211> LENGTH: 122
<212> TYPE: PRT
<213> ORGANISM: Homo sapiens

<400> SEQUENCE: 17

Gln Val Gln Leu Gln Val Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ala Trp Val Arg Gln Ala Pro Gly Lys Gly Leu Glu Trp Val
        35                  40                  45

Ala Ala Val Ser Asn Ser Gly Val Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Thr Arg Gln Leu Leu Thr Pro Arg Glu Phe Asp Tyr Trp
            100                 105                 110

Gly Gln Gly Thr Leu Val Thr Val Leu Ala
        115                 120

<210> SEQ ID NO 18
<211> LENGTH: 107
<212> TYPE: PRT
<213> ORGANISM: Homo sapiens

<400> SEQUENCE: 18

Glu Thr Thr Leu Thr Gln Ser Pro Ser Ser Val Ser Ala Ser Val Gly
1               5                   10                  15

Asp Arg Val Thr Leu Thr Cys Arg Ala Ser Gln Asp Ile Thr Arg Trp
            20                  25                  30

Leu Ala Trp Tyr Gln Gln Lys Pro Gly Lys Ala Pro Lys Leu Leu Ile
        35                  40                  45
```

```
Tyr Asp Ala Ser Ser Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly Ser Ser Val Pro Phe
                 85                  90                  95
Thr Phe Gly Gly Gly Thr Lys Val Glu Ile Lys
            100                 105
```

<210> SEQ ID NO 19
<211> LENGTH: 117
<212> TYPE: PRT
<213> ORGANISM: Homo sapiens

<400> SEQUENCE: 19

```
Gln Val Asn Leu Arg Glu Ser Gly Gly Leu Ile Gln Pro Gly Gly
 1               5                  10                  15
Ser Leu Arg Leu Ser Cys Ala Ala Ser Gly Phe Thr Phe Thr Asn Tyr
                 20                  25                  30
Ala Met Ser Trp Val Arg Gln Ala Pro Gly Lys Gly Leu Glu Trp Val
             35                  40                  45
Ser Ser Val Ser Ser Ala Gly Gly Ser Thr Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Arg Val Asn Arg Ala Phe Asp Leu Trp Gly Arg Gly Thr Leu
                100                 105                 110
Val Thr Val Ser Ala
            115
```

<210> SEQ ID NO 20
<211> LENGTH: 110
<212> TYPE: PRT
<213> ORGANISM: Homo sapiens

<400> SEQUENCE: 20

```
Asp Val Val Met Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
                 20                  25                  30
Tyr Leu Ala Trp Tyr Gln Gln Lys Pro Gly Gln Ala Pro Arg Leu Leu
             35                  40                  45
Ile Tyr Gly Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Pro Met Tyr Thr Phe Gly Gln Gly Thr Lys Leu Glu Ile Lys
                100                 105                 110
```

<210> SEQ ID NO 21
<211> LENGTH: 121
<212> TYPE: PRT
<213> ORGANISM: Homo sapiens

```
<400> SEQUENCE: 21

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Val Trp Val
        35                  40                  45

Gly Arg Ile Lys Ser Lys Thr Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Lys Ser Tyr Gly Tyr Thr Phe Asp Tyr Trp Gly
            100                 105                 110

Gln Gly Thr Leu Val Thr Val Ser Ala
        115                 120

<210> SEQ ID NO 22
<211> LENGTH: 110
<212> TYPE: PRT
<213> ORGANISM: Homo sapiens

<400> SEQUENCE: 22

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val His Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Ile Ser Ala Ser Leu Ala Ile Ser Gly Leu Gln
65                  70                  75                  80

Ser Glu Asp Glu Ala Val Tyr Tyr Cys Ala Thr Trp Asp Asp Arg Leu
                85                  90                  95

Ser Gly Pro Val Phe Ala Ala Gly Thr Lys Leu Thr Val Leu
            100                 105                 110

<210> SEQ ID NO 23
<211> LENGTH: 119
<212> TYPE: PRT
<213> ORGANISM: Homo sapiens

<400> SEQUENCE: 23

Gln Val Asn Leu Arg Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Ala Ile Ser Gly Ser Gly Ala Gly Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Arg Asp Arg Ser Leu Ser Phe Gly Phe Asp Ile Trp Gly Gln Gly
            100                 105                 110

Thr Leu Val Ser Val Ser Gly
        115

<210> SEQ ID NO 24
<211> LENGTH: 110
<212> TYPE: PRT
<213> ORGANISM: Homo sapiens

<400> SEQUENCE: 24

Asn Phe Met Leu Thr Gln Pro His Ser Val Ser Gly Ser Pro Gly Lys
1               5                   10                  15

Thr Val Thr Ile Ser Cys Thr Arg Ser Ser Gly Ser Ile Gly Ser Thr
            20                  25                  30

Tyr Val Gln Trp Tyr Gln Gln Arg Pro Gly Ser Pro Pro Thr Thr Val
        35                  40                  45

Ile Tyr Lys Asp Asp Gln Arg Pro Ser Gly Val Pro Asp Arg Phe Ser
    50                  55                  60

Gly Ser Ile Asp Gly Ser Ser Asn Ser Ala Ser Leu Thr Ile Ser Gly
65                  70                  75                  80

Leu Glu Thr Glu Asp Glu Ala Asp Tyr Tyr Cys Gln Ser Ser Asp Thr
                85                  90                  95

Ser Asn Leu Val Phe Gly Gly Gly Thr Lys Val Thr Val Leu
            100                 105                 110

<210> SEQ ID NO 25
<211> LENGTH: 121
<212> TYPE: PRT
<213> ORGANISM: Homo sapiens

<400> SEQUENCE: 25

Gln Val Gln Leu Gln Gln Ser Gly Gly Gly Leu Val Gln Pro Gly Gly
1               5                   10                  15

Ser Leu Arg Leu Ser Cys Ala Ala Pro Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gly Asp Gly Ser Gln Thr Tyr Tyr Ala Asp Ser Val
    50                  55                  60

Lys Gly Arg Phe Thr Ile Ser Arg Asp Asn Ala Met Lys Thr Val Tyr
65                  70                  75                  80

Leu Gln Met Asn Ser Leu Arg Ala Glu Asp Thr Ala Ile Tyr Tyr Cys
                85                  90                  95

Ala Lys Gly Ala Ala Tyr His Ile Asn Ser Trp Leu Asp Pro Trp Gly
            100                 105                 110

Gln Gly Thr Leu Val Thr Val Ser Ala
        115                 120

<210> SEQ ID NO 26
<211> LENGTH: 108
<212> TYPE: PRT
<213> ORGANISM: Homo sapiens

```
<400> SEQUENCE: 26

Glu Thr Thr Leu Thr Gln Ser Pro Gly Thr Leu Ser Val Ser Pro Gly
1               5                   10                  15

Glu Arg Val Thr Leu Ser Cys Arg Ala Ser Gln Ser Ile Ser Gly Asn
            20                  25                  30

Tyr Leu Ala Trp Tyr Gln Gln Arg Pro Gly Gln Ala Pro Arg Leu Leu
        35                  40                  45

Ile Tyr Gly Ala Phe Arg Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Thr Tyr Tyr Cys Gln His Tyr Asn Asn Phe Pro
                85                  90                  95

His Thr Phe Gly Ala Gly Thr Lys Val Asp Ile Lys
            100                 105

<210> SEQ ID NO 27
<211> LENGTH: 118
<212> TYPE: PRT
<213> ORGANISM: Homo sapiens

<400> SEQUENCE: 27

Lys Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Lys His Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 28
<211> LENGTH: 113
<212> TYPE: PRT
<213> ORGANISM: Homo sapiens

<400> SEQUENCE: 28

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Gln
            20                  25                  30

Val Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80
```

```
Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys
```

<210> SEQ ID NO 29
<211> LENGTH: 118
<212> TYPE: PRT
<213> ORGANISM: Homo sapiens

<400> SEQUENCE: 29

```
Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asn Ala
                20                  25                  30

Trp Met Asn Trp Val Arg Gln Ala Pro Gly Lys Gly Leu Glu Trp Val
            35                  40                  45

Gly Arg Ile Lys Arg Lys Thr Asp Gly Glu Thr Thr Asp Tyr Ala Ala
        50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115
```

<210> SEQ ID NO 30
<211> LENGTH: 113
<212> TYPE: PRT
<213> ORGANISM: Homo sapiens

<400> SEQUENCE: 30

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Pro
                20                  25                  30

Leu Asn Asn Arg Asn Tyr Leu Ala Trp Tyr Gln Gln Lys Pro Gly Gln
            35                  40                  45

Pro Pro Lys Leu Leu Ile Asn Gln Ala Ser Thr Arg Ala Ser Gly Val
        50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys
```

<210> SEQ ID NO 31
<211> LENGTH: 118
<212> TYPE: PRT
<213> ORGANISM: Homo sapiens

<400> SEQUENCE: 31

Lys Val Gln Leu Val Glu Ser Gly Gly Gly Leu Val Lys Pro Gly Gly
1               5                   10                  15

Ser Leu Arg Leu Ser Cys Ala Ala Ser Gly Leu Thr Phe Glu Arg Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 32
<211> LENGTH: 113
<212> TYPE: PRT
<213> ORGANISM: Homo sapiens

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ala
            20                  25                  30

Gly Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 33
<211> LENGTH: 118
<212> TYPE: PRT
<213> ORGANISM: Homo sapiens

<400> SEQUENCE: 33

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Pro Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Ala Gly Ser Asn Arg Ala Phe Asp Ile Trp Gly Gln Gly Thr
        100                 105                 110

Met Val Thr Val Ser Ala
        115

<210> SEQ ID NO 34
<211> LENGTH: 113
<212> TYPE: PRT
<213> ORGANISM: Homo sapiens

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Pro
            20                  25                  30

Gly Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
            85                  90                  95

Tyr Tyr Thr Pro Pro Leu Ala Phe Gly Gly Gly Thr Lys Leu Glu Ile
        100                 105                 110

Lys

<210> SEQ ID NO 35
<211> LENGTH: 118
<212> TYPE: PRT
<213> ORGANISM: Homo sapiens

<400> SEQUENCE: 35

Lys Val Gln Leu Val Glu Ser Gly Gly Gly Leu Val Lys Pro Gly Gly
1               5                   10                  15

Ser Leu Arg Leu Ser Cys Ala Ala Ser Gly Leu Thr Phe Gly Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Ala Gly Ser Asn Arg Ala Phe Asp Ile Trp Gly Gln Gly Thr
        100                 105                 110

Met Val Thr Val Ser Ala
        115

<210> SEQ ID NO 36
<211> LENGTH: 113

```
<212> TYPE: PRT
<213> ORGANISM: Homo sapiens

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Pro
            20                  25                  30

Gly Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65              70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 37
<211> LENGTH: 118
<212> TYPE: PRT
<213> ORGANISM: Homo sapiens

<400> SEQUENCE: 37

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65              70                  75                  80

Leu Tyr Leu Gln Met Asn Ser Leu Lys Thr Glu Asp Thr Ala Val Tyr
                85                  90                  95

Tyr Cys Ala Gly Gly Asn His Ser Ser Asp Ile Trp Gly Gln Gly Thr
            100                 105                 110

Met Val Thr Val Ser Ala
        115

<210> SEQ ID NO 38
<211> LENGTH: 113
<212> TYPE: PRT
<213> ORGANISM: Homo sapiens

<400> SEQUENCE: 38

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60
```

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 39
<211> LENGTH: 118
<212> TYPE: PRT
<213> ORGANISM: Homo sapiens

<400> SEQUENCE: 39

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Asn Trp Val Arg Gln Ala Pro Gly Lys Gly Leu Glu Trp Val
            35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Gly Ala His Ser Ser Asp Ile Trp Gly Gln Gly Thr
            100                 105                 110

Met Val Thr Val Ser Ala
            115

<210> SEQ ID NO 40
<211> LENGTH: 113
<212> TYPE: PRT
<213> ORGANISM: Homo sapiens

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Arg Asn Tyr Leu Ala Trp Tyr Gln Gln Lys Pro Gly Gln
            35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 41
<211> LENGTH: 118
<212> TYPE: PRT

<213> ORGANISM: Homo sapiens

<400> SEQUENCE: 41

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Gly Gln His Ser Ser Asp Ile Trp Gly Gln Gly Thr
            100                 105                 110

Met Val Thr Val Ser Ala
            115

<210> SEQ ID NO 42
<211> LENGTH: 113
<212> TYPE: PRT
<213> ORGANISM: Homo sapiens

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 43
<211> LENGTH: 118
<212> TYPE: PRT
<213> ORGANISM: Homo sapiens

<400> SEQUENCE: 43

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Ala Tyr Ala Phe Asp Ala Trp Gly Gln Gly Thr
            100                 105                 110

Met Val Thr Val Ser Ala
            115

<210> SEQ ID NO 44
<211> LENGTH: 113
<212> TYPE: PRT
<213> ORGANISM: Homo sapiens

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Thr Lys Leu Glu Ile
            100                 105                 110

Lys

<210> SEQ ID NO 45
<211> LENGTH: 118
<212> TYPE: PRT
<213> ORGANISM: Homo sapiens

<400> SEQUENCE: 45

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Ala Tyr Ala Phe Asp Ser Trp Gly Gln Gly Thr
            100                 105                 110

Met Val Thr Val Ser Ala
            115

<210> SEQ ID NO 46
<211> LENGTH: 113
<212> TYPE: PRT

<213> ORGANISM: Homo sapiens

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 47
<211> LENGTH: 118
<212> TYPE: PRT
<213> ORGANISM: Homo sapiens

<400> SEQUENCE: 47

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asp Arg Ala Ser Asp Lys Trp Gly Gln Gly Thr
            100                 105                 110

Met Val Thr Val Ser Ala
        115

<210> SEQ ID NO 48
<211> LENGTH: 113
<212> TYPE: PRT
<213> ORGANISM: Homo sapiens

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
50                  55                  60

```
Pro Asp Arg Phe Ser Gly Ser Gly Ser Gly Thr Glu Phe Thr Leu Ile
 65                  70                  75                  80

Ile Ser Ser Leu Gln Ala Glu Asp Val Ala Ile Tyr Tyr Cys Gln Gln
                 85                  90                  95

Tyr Tyr Thr Pro Pro Leu Ala Phe Gly Gly Gly Thr Lys Leu Glu Ile
            100                 105                 110

Lys
```

<210> SEQ ID NO 49
<211> LENGTH: 118
<212> TYPE: PRT
<213> ORGANISM: Homo sapiens

<400> SEQUENCE: 49

```
Lys Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Trp Met Asn Trp Val Arg Gln Ala Pro Gly Lys Gly Leu Glu Trp Val
             35                  40                  45

Gly Arg Ile Lys Arg Lys Thr Asp Gly Glu Thr Thr Asp Tyr Ala Ala
 50                  55                  60

Pro Val Lys Gly Arg Phe Ser Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Gly Ser Ala Tyr Ala Phe Asp Thr Trp Gly Gln Gly Thr
            100                 105                 110

Met Val Thr Val Ser Ala
        115
```

<210> SEQ ID NO 50
<211> LENGTH: 113
<212> TYPE: PRT
<213> ORGANISM: Homo sapiens

<400> SEQUENCE: 50

```
Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
                 20                  25                  30

Ser Asn Asn Arg Asn Tyr Leu Ala Trp Tyr Gln Gln Lys Pro Gly Gln
             35                  40                  45

Pro Pro Lys Leu Leu Ile Asn Gln Ala Ser Thr Arg Ala Ser Gly Val
 50                  55                  60

Pro Asp Arg Phe Ser Gly Ser Gly Ser Gly Thr Glu Phe Thr Leu Ile
 65                  70                  75                  80

Ile Ser Ser Leu Gln Ala Glu Asp Val Ala Ile Tyr Tyr Cys Gln Gln
                 85                  90                  95

Tyr Tyr Thr Pro Pro Leu Ala Phe Gly Gly Gly Thr Lys Leu Glu Ile
            100                 105                 110

Lys
```

<210> SEQ ID NO 51
<211> LENGTH: 118
<212> TYPE: PRT
<213> ORGANISM: Homo sapiens

<400> SEQUENCE: 51

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Gly Asn His Ser Gln Asp Ile Trp Gly Gln Gly Thr
            100                 105                 110

Met Val Thr Val Ser Ala
        115

<210> SEQ ID NO 52
<211> LENGTH: 113
<212> TYPE: PRT
<213> ORGANISM: Homo sapiens

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 53
<211> LENGTH: 118
<212> TYPE: PRT
<213> ORGANISM: Homo sapiens

<400> SEQUENCE: 53

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Ala Gly Gly Gln His Ser Gln Asp Ile Trp Gly Gln Gly Thr
            100                 105                 110

Met Val Thr Val Ser Ala
        115

<210> SEQ ID NO 54
<211> LENGTH: 113
<212> TYPE: PRT
<213> ORGANISM: Homo sapiens

<400> SEQUENCE: 54

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
            85                  90                  95

Tyr Tyr Thr Pro Pro Leu Ala Phe Gly Gly Gly Thr Lys Leu Glu Ile
            100                 105                 110

Lys

<210> SEQ ID NO 55
<211> LENGTH: 118
<212> TYPE: PRT
<213> ORGANISM: Homo sapiens

<400> SEQUENCE: 55

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Ala Gly Gly Ala His Ser Gln Asp Ile Trp Gly Gln Gly Thr
            100                 105                 110

Met Val Thr Val Ser Ala
        115

<210> SEQ ID NO 56
<211> LENGTH: 113

```
<212> TYPE: PRT
<213> ORGANISM: Homo sapiens

<400> SEQUENCE: 56

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Tyr Thr Pro Pro Leu Ala Phe Gly Gly Gly Thr Lys Leu Glu Ile
            100                 105                 110

Lys

<210> SEQ ID NO 57
<211> LENGTH: 118
<212> TYPE: PRT
<213> ORGANISM: Homo sapiens

<400> SEQUENCE: 57

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 58
<211> LENGTH: 113
<212> TYPE: PRT
<213> ORGANISM: Homo sapiens

<400> SEQUENCE: 58

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60
```

```
Pro Asp Arg Phe Ser Gly Ser Gly Ser Gly Thr Glu Phe Thr Leu Ile
 65                  70                  75                  80

Ile Ser Ser Leu Gln Ala Glu Asp Val Ala Ile Tyr Tyr Cys Gln Gln
                 85                  90                  95

Tyr Leu Thr Pro Pro Leu Ala Phe Gly Gly Gly Thr Lys Leu Glu Ile
            100                 105                 110

Lys
```

<210> SEQ ID NO 59
<211> LENGTH: 118
<212> TYPE: PRT
<213> ORGANISM: Homo sapiens

<400> SEQUENCE: 59

```
Lys Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Asn Trp Val Arg Gln Ala Pro Gly Lys Gly Leu Glu Trp Val
         35                  40                  45

Gly Arg Ile Lys Arg Lys Thr Asp Gly Glu Thr Thr Asp Tyr Ala Ala
 50                  55                  60

Pro Val Lys Gly Arg Phe Ser Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Gly Ser Asn Arg Ala Phe Asp Ile Trp Gly Gln Gly Thr
            100                 105                 110

Met Val Thr Val Ser Ala
            115
```

<210> SEQ ID NO 60
<211> LENGTH: 113
<212> TYPE: PRT
<213> ORGANISM: Homo sapiens

<400> SEQUENCE: 60

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Arg Asn Tyr Leu Ala Trp Tyr Gln Gln Lys Pro Gly Gln
         35                  40                  45

Pro Pro Lys Leu Leu Ile Asn Gln Ala Ser Thr Arg Ala Ser Gly Val
 50                  55                  60

Pro Asp Arg Phe Ser Gly Ser Gly Ser Gly Thr Glu Phe Thr Leu Ile
 65                  70                  75                  80

Ile Ser Ser Leu Gln Ala Glu Asp Val Ala Ile Tyr Tyr Cys Gln Gln
                 85                  90                  95

Tyr Leu Arg Pro Pro Leu Asn Phe Gly Gly Gly Thr Lys Leu Glu Ile
            100                 105                 110

Lys
```

<210> SEQ ID NO 61
<211> LENGTH: 118
<212> TYPE: PRT

<213> ORGANISM: Homo sapiens

<400> SEQUENCE: 61

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 62
<211> LENGTH: 113
<212> TYPE: PRT
<213> ORGANISM: Homo sapiens

<400> SEQUENCE: 62

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Leu Thr Pro Pro Leu Asn Phe Gly Gly Gly Thr Lys Leu Glu Ile
            100                 105                 110

Lys

<210> SEQ ID NO 63
<211> LENGTH: 118
<212> TYPE: PRT
<213> ORGANISM: Homo sapiens

<400> SEQUENCE: 63

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

```
Pro Val Lys Gly Arg Phe Ser Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Gly Ser Asn Arg Ala Phe Asp Ile Trp Gly Gln Gly Thr
            100                 105                 110

Met Val Thr Val Ser Ala
            115
```

```
<210> SEQ ID NO 64
<211> LENGTH: 113
<212> TYPE: PRT
<213> ORGANISM: Homo sapiens

<400> SEQUENCE: 64

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
             20                  25                  30

Ser Asn Asn Arg Asn Tyr Leu Ala Trp Tyr Gln Gln Lys Pro Gly Gln
         35                  40                  45

Pro Pro Lys Leu Leu Ile Asn Gln Ala Ser Thr Arg Ala Ser Gly Val
 50                  55                  60

Pro Asp Arg Phe Ser Gly Ser Gly Ser Gly Thr Glu Phe Thr Leu Ile
 65                  70                  75                  80

Ile Ser Ser Leu Gln Ala Glu Asp Val Ala Ile Tyr Tyr Cys Gln Asn
                 85                  90                  95

Tyr Leu Thr Pro Pro Leu Ser Phe Gly Gly Thr Lys Leu Glu Ile
            100                 105                 110

Lys
```

```
<210> SEQ ID NO 65
<211> LENGTH: 118
<212> TYPE: PRT
<213> ORGANISM: Homo sapiens

<400> SEQUENCE: 65

Lys Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Asn Trp Val Arg Gln Ala Pro Gly Lys Gly Leu Glu Trp Val
         35                  40                  45

Gly Arg Ile Lys Arg Lys Thr Asp Gly Glu Thr Thr Asp Tyr Ala Ala
 50                  55                  60

Pro Val Lys Gly Arg Phe Ser Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Gly Ser Asn Arg Ala Phe Asp Ile Trp Gly Gln Gly Thr
            100                 105                 110

Met Val Thr Val Ser Ala
            115
```

```
<210> SEQ ID NO 66
<211> LENGTH: 113
<212> TYPE: PRT
```

<213> ORGANISM: Homo sapiens

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Leu Lys Ala Pro Leu Ala Phe Gly Gly Gly Thr Lys Leu Glu Ile
            100                 105                 110

Lys

<210> SEQ ID NO 67
<211> LENGTH: 118
<212> TYPE: PRT
<213> ORGANISM: Homo sapiens

<400> SEQUENCE: 67

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 68
<211> LENGTH: 113
<212> TYPE: PRT
<213> ORGANISM: Homo sapiens

<400> SEQUENCE: 68

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Leu Asn Ala Pro Leu His Phe Gly Gly Gly Thr Lys Leu Glu Ile
            100                 105                 110

Lys

<210> SEQ ID NO 69
<211> LENGTH: 118
<212> TYPE: PRT
<213> ORGANISM: Homo sapiens

<400> SEQUENCE: 69

Lys Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Asn Trp Val Arg Gln Ala Pro Gly Lys Gly Leu Glu Trp Val
            35                  40                  45

Gly Arg Ile Lys Arg Lys Thr Asp Gly Glu Thr Thr Asp Tyr Ala Ala
        50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 70
<211> LENGTH: 113
<212> TYPE: PRT
<213> ORGANISM: Homo sapiens

<400> SEQUENCE: 70

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Arg Asn Tyr Leu Ala Trp Tyr Gln Gln Lys Pro Gly Gln
            35                  40                  45

Pro Pro Lys Leu Leu Ile Asn Gln Ala Ser Thr Arg Ala Ser Gly Val
        50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Leu Glu Ala Pro Leu Val Phe Gly Gly Gly Thr Lys Leu Glu Ile
            100                 105                 110

Lys

<210> SEQ ID NO 71
<211> LENGTH: 118
<212> TYPE: PRT
<213> ORGANISM: Homo sapiens

<400> SEQUENCE: 71

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 72
<211> LENGTH: 113
<212> TYPE: PRT
<213> ORGANISM: Homo sapiens

<400> SEQUENCE: 72

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Gln
                85                  90                  95

Tyr Leu Lys Ala Pro Leu His Phe Gly Gly Gly Thr Lys Leu Glu Ile
            100                 105                 110

Lys

<210> SEQ ID NO 73
<211> LENGTH: 118
<212> TYPE: PRT
<213> ORGANISM: Homo sapiens

<400> SEQUENCE: 73

Lys Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
    50                  55                  60

-continued

```
Pro Val Lys Gly Arg Phe Ser Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 74
<211> LENGTH: 113
<212> TYPE: PRT
<213> ORGANISM: Homo sapiens

<400> SEQUENCE: 74

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
 50                  55                  60

Pro Asp Arg Phe Ser Gly Ser Gly Ser Gly Thr Glu Phe Thr Leu Ile
 65                  70                  75                  80

Ile Ser Ser Leu Gln Ala Glu Asp Val Ala Ile Tyr Tyr Cys Gln Arg
                 85                  90                  95

Leu Ile Ala Pro Pro Phe Thr Phe Gly Gly Gly Thr Lys Leu Glu Ile
            100                 105                 110

Lys

<210> SEQ ID NO 75
<211> LENGTH: 118
<212> TYPE: PRT
<213> ORGANISM: Homo sapiens

<400> SEQUENCE: 75

Lys Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Glu Thr Thr Asp Tyr Ala Ala
 50                  55                  60

Pro Val Lys Gly Arg Phe Ser Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Gly Ser Asn Arg Ala Phe Asp Ile Trp Gly Gln Gly Thr
            100                 105                 110

Met Val Thr Val Ser Ala
        115

<210> SEQ ID NO 76
<211> LENGTH: 113
```

-continued

```
<212> TYPE: PRT
<213> ORGANISM: Homo sapiens

<400> SEQUENCE: 76

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Leu Ile Asn Gln Ala Ser Thr Arg Ala Ser Gly Val
    50                  55                  60

Pro Asp Arg Phe Ser Gly Ser Gly Ser Gly Thr Glu Phe Thr Leu Ile
65                  70                  75                  80

Ile Ser Ser Leu Gln Ala Glu Asp Val Ala Ile Tyr Tyr Cys Gln Asn
                85                  90                  95

Tyr Leu Thr Pro Pro Leu Ala Phe Gly Gly Gly Thr Lys Leu Glu Ile
            100                 105                 110

Lys

<210> SEQ ID NO 77
<211> LENGTH: 360
<212> TYPE: DNA
<213> ORGANISM: Homo sapiens

<400> SEQUENCE: 77
caggtccaac tggtgcagtc tggggctgaa gtgaagaagc tggggtcttc agtgaaggtg      60
tcctgcaagg cttctggcta caccttcagc agctactata tgcactgggt gaggcaggct     120
cctggacaag gccttgagtg gatgggagag attaatccca caatgcccg  tattaacttc     180 aatgaaaagt tcaagaccag ggtcacactc actgtggaca atccaccag cacagcatac     240 atggagctca gcagcctgag atctgaggac accgcggtct attactgtac cagaggatac     300
tataggtacg gggcctggtt tggttactgg ggccaaggga ctctggtcac tgtctcttca     360

<210> SEQ ID NO 78
<211> LENGTH: 321
<212> TYPE: DNA
<213> ORGANISM: Homo sapiens

<400> SEQUENCE: 78
gatatccaga tgacacagtc tccatcctcc ctgtctgcct ctgtgggaga cagagtcacc      60
atcacttgca gggcaagtca ggacattagc gattatttga actggtatca acagaaacca     120
ggcaaggctc ctaaactcct gatctactac atatcaagat acactcagg  agtcccatca     180 cgcttcagtg gcagtgggtc tggaacagat tatactctca ccattagctc cctgcagcca     240
gaagattttg ccacttacta ttgccaacag ggtcatacac ttccgtggac cttcggtgga     300
ggcaccaagg tggaaatcaa a                                                321

<210> SEQ ID NO 79
<211> LENGTH: 357
<212> TYPE: DNA
<213> ORGANISM: Homo sapiens

<400> SEQUENCE: 79
caggtacagc tgcagcagtc aggggg aggc ttggtacagc ctgggggg tc cctaagactc      60 tcctgtacag cctctggatt cacctttagc agctatgcca tgagctgggt ccgccaggct     120
```

```
ccagggaagg ggctggagtg ggtctcagca attagtggta gtggtggtag cacatactac      180
gcagactccg tgaagggccg gttcaccatc tccagagaca attccaagaa cacgctgtat      240
ctgcaaatga acagcctgag agtcgaggac acggccgtat attactgtgc gagatatagt      300
attggtagac acacctttga ccactggggc cagggcaccc tggtcaccgt ctcggcc         357

<210> SEQ ID NO 80
<211> LENGTH: 354
<212> TYPE: DNA
<213> ORGANISM: Homo sapiens

<400> SEQUENCE: 80
aaggtgcagc tggtggagtc tgggggaggc ttggtaaagc ctgggggtc ccttagactc        60 tcctgtgcag cctctggttt cactttcagt aacgcctgga tgaactgggt ccgccaggct      120
ccagggaagg ggctggagtg ggtcggccgt attaaaagga aaactgatgg tgagacaaca      180
gactacgctg cacccgtgaa aggcagattc agcatctcaa gagatgattc aaaaaacacc      240
ctgtatctgc aaatgaacag cttgaaaacc gaggacacag ccgtgtatta ctgcgctggc      300
agtaaccgag cttttgatat ctggggccaa gggacaatgg tcaccgtctc tgcc            354

<210> SEQ ID NO 81
<211> LENGTH: 354
<212> TYPE: DNA
<213> ORGANISM: Homo sapiens

<400> SEQUENCE: 81
caggtacagc tgcagcagtc aggggaggc ttggtacagc ctgggggtc cctgagactc         60 tcctgtgcag cctctggatt caccttagc ggctatgcca tgacttgggt ccgccaggct       120
ccagggaagg ggctggagtg ggtctcagct attacttcta ctggtggtcg cacatactac      180
gcagactccg tgaagggccg gttcaccacc tccagagaca attccaggaa cacgttgtat      240
ctgcaaatga acagcctgag agccgaagac acggccgtat attactgtgc gagagagtca      300
aacttcaggg cttttgatat ctggggccaa gggacaatgg tcaccgtctc tgcc            354

<210> SEQ ID NO 82
<211> LENGTH: 354
<212> TYPE: DNA
<213> ORGANISM: Homo sapiens

<400> SEQUENCE: 82
gaggtgcagc tggtggagtc tgggggaggc ttggtacagc ctgggggtc ccttagactc        60 tcctgtgcag cctctggatt cactttcatt gacgcctgga tgacctgggt ccgccaggct      120
ccagggaagg ggctggagtg ggtctcagtt atttatagcg gtggtagcac atactacgca      180
gactccgtga aggcagatt caccatctcc agagacaatt ccaagaacac gctgtatctg      240
caaatgaaca gcctgagagc cgaggacacg gccgtatatt actgtgcgag aggggctagg      300
ggccatcccg ggcaggacta ctgggggcag ggcaccctgg tcaccgtctc ggcc            354

<210> SEQ ID NO 83
<211> LENGTH: 351
<212> TYPE: DNA
<213> ORGANISM: Homo sapiens
```

<400> SEQUENCE: 83

```
caggtcaact taagggagtc tgggggaggc ttggtacagc ctggcgggtc cctgagactc    60
tcctgtgcag cctctggatt caccttcagt gactactaca tgagctggat ccgccaggct   120
ccagggggg ggctggagtg ggtttcatac actagtcgtt ttggtagtga cacaaactac   180
gcagactctg tgaagggccg attcaccatc tccagagaca cgtccagaa ctcactatat   240
ctgcaaatga acagcctgag ggccgaggac acggctgttt attactgtgt gagagatgta   300
cataacaggg atgcctactg gggccagggc accctggtca ccgtctcggc c            351
```

<210> SEQ ID NO 84
<211> LENGTH: 369
<212> TYPE: DNA
<213> ORGANISM: Homo sapiens

<400> SEQUENCE: 84

```
caggtgcagc tggtgcagtc tgggggaggc ttggtacagc ctgggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaacacagat   300
tactatgata gtagtagcca taccccgct gactactggg gccagggcac cctggtcacc   360
gtctcggcc                                                           369
```

<210> SEQ ID NO 85
<211> LENGTH: 366
<212> TYPE: DNA
<213> ORGANISM: Homo sapiens

<400> SEQUENCE: 85

```
caggtgcagc tgcaggagtc gggggaggc ttggtacagc ctgggggtc cctgagactc     60
tcctgtgcag cctctggatt cacctttagt agctatggca tgagctgggt ccgccaggct   120
ccagggaaag ggctggagtg ggtctcaact atcagtggca gtggtagtag cacaaactac   180
gcagactccg tgaagggccg gttcaccatc tccagagaca attccaagaa cacgctatt   240
ctgcaaatga acagcctgag agccgaggac acggccgtat atttctgtgc gaaaggccga   300
tattactatg atagtcttga tgcttttgat atctggggcc aagggacaat ggtcaccgtc   360
tctgcc                                                              366
```

<210> SEQ ID NO 86
<211> LENGTH: 366
<212> TYPE: DNA
<213> ORGANISM: Homo sapiens

<400> SEQUENCE: 86

```
caggtacagc tggtggagtc tgggggaggc ttggtacagc ctgggggtc cctgagactc     60
tcctgtgcag cctctggatt cacctttagc agctatgcca tgagctgggt ccgccaggct   120
ccagggaagg ggctggagtg ggtctcagct attagtggta ctggtggtag cacatactac   180
gcagactccg tgaagggccg gttcaccatc tccagagaca attccaagaa cacgctgtat   240
ctgcaaatga acagcctgag agccgaggac acggccgcat attactgtgc gaaagataaa   300
tggagcagct ggcccactta ctactttgac tactggggcc agggaaccct ggtcaccgtc   360
```

```
tcggcc                                                          366

<210> SEQ ID NO 87
<211> LENGTH: 366
<212> TYPE: DNA
<213> ORGANISM: Homo sapiens

<400> SEQUENCE: 87
caggtgcagc tgcaggtgtc gggggaggc ttggtacagc ctgggggtc cctgagactc    60 tcctgtgcag cctctggatt caccttcagt agctatagca tggcctgggt ccgccaggct  120
ccagggaagg ggctggagtg ggtcgcggct gttagtaata gtggtgttga gacatactac  180
gcagactccg tgaagggccg gttcaccatc tccagagaca attccaagaa cacgctgtat  240
ttgcaaatga acagcctgag agccgaggac acggccgtat attactgtgc gaaacgaact  300
agacaactgc taactccgcg ggagtttgac tactggggcc agggcaccct ggtcaccgtc  360
ttggcc                                                          366

<210> SEQ ID NO 88
<211> LENGTH: 351
<212> TYPE: DNA
<213> ORGANISM: Homo sapiens

<400> SEQUENCE: 88
caggtcaact taagggagtc tgggggaggc ttgatacagc ctgggggtc cctgagactc    60 tcctgtgcag cctctggatt cacctttacc aattatgcca tgagctgggt ccgccaggct  120
ccagggaagg ggctggagtg ggtctcaagt gttagtagtg ctggtggtag tacatactac  180
gcagactccg tgaagggccg gttcaccatc tccagagaca acgccaagaa ctcactgtat  240
ctgcaaatga acagcctgag agccgaggac acggctgttt attactgtgc gagacgagtc  300
aatcgggcct tcgatctctg gggccgtgga accctggtca ccgtctcggc c           351

<210> SEQ ID NO 89
<211> LENGTH: 363
<212> TYPE: DNA
<213> ORGANISM: Homo sapiens

<400> SEQUENCE: 89
caggtgcagc tgcaggagtc gggggaggc ttggtacagc ctgggggtc ccttagactc    60 tcctgtgcag cctctggatt cactttcagt aacgcctgga tgagctgggt ccgccaggct  120
ccagggaagg ggctggtgtg ggttggccgt attaaaagca aaactgatgg tgggacaaca  180
gactacgctg cacccgtgaa aggcagattc accatctcaa gagatgattc aaaaaacacg  240
ctgtatctgc aaatgaacag cctgaaaacc gaggacacag ccgtgtatta ctgtaccaca  300
gataagagct atggttacac atttgactac tggggccagg gcaccctggt caccgtctcg  360
gcc                                                             363

<210> SEQ ID NO 90
<211> LENGTH: 357
<212> TYPE: DNA
<213> ORGANISM: Homo sapiens

<400> SEQUENCE: 90
caggtcaact taagggagtc tgggggaggc ttggtaaagc cggggggtc ccttagactc    60 tcctgtgcag cctctggatt caccttcagt agctactgga tgcactgggt ccgccaagcc  120
ccagggaagg ggctggagtg ggtctcagct atcagtggta gtggtgccgg cacatactac  180
```

```
ccagactccg tgaagggccg gttcaccatc tccagagaca attccaagaa cacgctgtat    240
ctgcaaatga acagcctgag agccgaggac acggccgtat attactgtgc gagagatcgg    300
tccttatctt ttggttttga tatttggggc caaggcaccc tggtctccgt ctctggc       357

<210> SEQ ID NO 91
<211> LENGTH: 363
<212> TYPE: DNA
<213> ORGANISM: Homo sapiens

<400> SEQUENCE: 91
caggtacagc tgcagcagtc aggggggaggc ttggtccagc cggggggggtc actgagactc    60 tcctgtgcag cccctggatt cacctttagt agatattgga tgagttgggt ccgccaggct    120
ccagggaagg gactggagtg ggtggccaac ataaagggag atggaagtca gacatactat    180
gcggactctg tgaagggccg attcaccatc tccagagaca cgccatgaa acagtgtat     240 ctgcaaatga acagcctgag agccgaggac acggccatat attactgtgc gaaaggggct    300
gcttatcaca ttaacagctg gctcgacccc tggggccagg caccctggt caccgtctcg    360 gcc                                                                 363

<210> SEQ ID NO 92
<211> LENGTH: 333
<212> TYPE: DNA
<213> ORGANISM: Homo sapiens

<400> SEQUENCE: 92
aattttatgc tgactcagcc ccactctgtg tcggagtctc cggggaagac ggtaaccatc    60
tcctgcaccc gcagcagtgg cggcattgcc agtaactttg tgcagtggta ccagcagcgc    120
ccgggcagtg tccccaccac tgtgatctat agggataacc aaagaccctc tggagtccct    180
gatcggttct ctggctccgt cgacagctcc tccaattctg cctccctcac catctctggg    240
ctgaagactg acgatgaggc tgactattat tgtcagtcct atgatgacca caatcattgg    300
gtgttcggcg gcgggaccaa gctgaccgtc cta                                333

<210> SEQ ID NO 93
<211> LENGTH: 339
<212> TYPE: DNA
<213> ORGANISM: Homo sapiens

<400> SEQUENCE: 93
gacatcgtga tgacccagtc tccagactcc ctggctgtgt ctctgggcga gagggccacc    60
atcaactgca agtccagcca gagtgtttta tacagctcca acaataggaa ctacctagct    120
tggtaccagc agaaaccagg acagcctcct aagctgctca ttaaccaggc atctacccgg    180
gcatccggcg tccctgaccg attcagtggc agcgggtctg ggacagagtt cactctcatc    240
atcagcagcc tgcaggctga agatgtggcg atttattact gtcagcaata ttatactcct    300
cccctcgctt tcggcggagg gaccaagctg gagatcaaa                          339

<210> SEQ ID NO 94
<211> LENGTH: 336
<212> TYPE: DNA
<213> ORGANISM: Homo sapiens
```

<400> SEQUENCE: 94

```
gaaattgtgt tgacgcagtc tccactctcc ctgcccgtca cccctggaga gccggcctcc      60
atctcctgca ggtctagtca gagcctcctg cacagtaatg gatacaacta tttggattgg     120
tacctgcaga aaccagggca gtctccacag ctcctgatct atttgaattc taatcgggcc     180
tccggggtcc ctgacaggtt cagtggcagt ggatcaggta cagattttac actgcaaatc     240
agcagagtgg aggctgagga tgttggggtt tactactgta tgcaagctct acaaattcct     300
cccacttcg gcggagggac caaagtggat atcaaa                                336
```

<210> SEQ ID NO 95
<211> LENGTH: 336
<212> TYPE: DNA
<213> ORGANISM: Homo sapiens

<400> SEQUENCE: 95

```
aattttatgc tgactcagcc ccactctgtg tcggagtctc cgggaaagac ggtaaccatc      60
tcctgcaccc gcagcagtgg caccattgcc agcaactttg tgcagtggta tcaacagcgc     120
ccgggcagtt cgcccacccc agtgatcttt gagaatgacc gaagaccctc tggggtccct     180
gatcggttct ctggctccat cgacagctcc tccaattctg cctccctcac catttcgtca     240
ctgaacactg aggacaaggc tgactactac tgtcagtcct atgatagcag cactcatggg     300
tgggtgtttg gcggagggac ccagctcacc gtttta                               336
```

<210> SEQ ID NO 96
<211> LENGTH: 330
<212> TYPE: DNA
<213> ORGANISM: Homo sapiens

<400> SEQUENCE: 96

```
tcctatgtgc tgactcagcc accctcagcg tctgggaccc ccgggcagag ggtcaccatc      60
tcttgttctg gaagcagctc caacatcggc ggtaattctg tatcctggta ccagcaactc     120
ccaggaacgg cccccaagct cctcatctat aggaatcatc agcggccctc aggggtccct     180
gaccgattct ctggctccaa gtctggcacc tcagcctccc tggccatcag tgggctccgg     240
tccgacgacg aggctgatta ttattgtgca acatgggatt tcagcctgag tggttttgtc     300
ttcggaactg ggaccaaggt caccgtccta                                      330
```

<210> SEQ ID NO 97
<211> LENGTH: 324
<212> TYPE: DNA
<213> ORGANISM: Homo sapiens

<400> SEQUENCE: 97

```
gaaactacac tcacgcagtc tccatcctcc ctgtctgcat ctgtaggaga cagagtcacc      60
atcacttgcc gggccagtca ggacatcaga aatgatttag actggtttca acaaaaacca     120
ggcgaagccc ctaaacgcct gatctctgct gcatctaatt tgcagagtgg ggtcccctca     180
cgattcagcg gcggtggctc tggctccgaa ttcactctca caatccacag cctggagtct     240
gaagattttg caacttacta ctgtcaacag agttacatta cccctccttg gacgttcggc     300
caagggacca gctggagat caaa                                              324
```

<210> SEQ ID NO 98
<211> LENGTH: 324
<212> TYPE: DNA

<213> ORGANISM: Homo sapiens

<400> SEQUENCE: 98

| gaaattgtgt tgacgcagtc tccaggcacc ctgtctttgt ctccagggga aagagccacc | 60 |
| ctctcctgca gggccagtca ggaaattagg accgcctact tagcctggta ccagcagaaa | 120 |
| cctggccagg ctcccaggct cctcatctat tatgcatcca gcagggccac tggcatccca | 180 |
| gacaggttca gcggcagtag gtctgggaca gacttcactc tcaccatcag cagactggag | 240 |
| cctgaagatt ttgcagtgta ttcctgtcag cagtatgata cctcacctcc caccttcggc | 300 |
| caagggacac gactggagat taaa | 324 |

<210> SEQ ID NO 99
<211> LENGTH: 330
<212> TYPE: DNA
<213> ORGANISM: Homo sapiens

<400> SEQUENCE: 99

| aattttatgc tgactcagcc ccactctgtg tcggagtctc cggggaagac ggtaaccatc | 60 |
| tcctgcaccc gcagcagtgg cagcattgcc agcaactatg tgcagtggta ccaacagcgc | 120 |
| ccgggcagtt cccccaccac tgtgatctat gaggataacc aaagaccctc tggggtccct | 180 |
| gatcggttct ctggctccat cgacagctcc tccaactctg cctccctcac catctctgga | 240 |
| ctgaagactg aggacgaggc tgactactac tgtcagtctt atgatagcag caatgtgata | 300 |
| ttcggcggag ggaccaaggt caccgtccta | 330 |

<210> SEQ ID NO 100
<211> LENGTH: 321
<212> TYPE: DNA
<213> ORGANISM: Homo sapiens

<400> SEQUENCE: 100

| gaaactacac tcacgcagtc tccatcttcc gtgtctgcat ctgtaggaga cagagtcacc | 60 |
| ctcacttgtc gggcgagtca ggatatcaca aggtggttag cctggtatca gcagaaacca | 120 |
| gggaaagccc ctaagctcct gatctatgat gcatccagtt tgcaaagtgg ggtcccatca | 180 |
| agattcagcg gcagtggatc tgggacagat ttcactctca ccatcagcag tctgcaacct | 240 |
| gaagattttg caacttacta ctgtcaacag ggttccagtg ttcctttcac tttcggcgga | 300 |
| gggaccaagg tggagatcaa a | 321 |

<210> SEQ ID NO 101
<211> LENGTH: 330
<212> TYPE: DNA
<213> ORGANISM: Homo sapiens

<400> SEQUENCE: 101

| gatgttgtga tgactcagtc tccaggcacc ctgtctttgt ctccagggga aagagccacc | 60 |
| ctctcctgca gggccagtca gagtgttagc agcagctact tagcctggta ccaacagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcacctcc tatgtacact | 300 |
| tttggccagg ggaccaagct ggagatcaaa | 330 |

<210> SEQ ID NO 102
<211> LENGTH: 330

<212> TYPE: DNA
<213> ORGANISM: Homo sapiens

<400> SEQUENCE: 102

```
tcctatgtgc tgactcagcc accctcagcg tctgggaccc ccgggcagag ggtcaccatc    60
tcttgttctg gaagtggctc aacatcgga agtaattctg ttcactgtgta ccagcaactc   120
ccaggaacgg cccccaaact cctcatctat actaataatc agcggccctc aggggtccct   180
gaccgattct ctggctccaa gtctggcatt tcagcctccc tggctatcag tgggctccag   240
tctgaggatg aggctgttta ttactgtgca acgtgggatg acagactgag tggtccggtg   300
ttcgccgcag ggaccaagct gaccgtccta                                    330
```

<210> SEQ ID NO 103
<211> LENGTH: 330
<212> TYPE: DNA
<213> ORGANISM: Homo sapiens

<400> SEQUENCE: 103

```
aattttatgc tgactcagcc ccactctgtg tcggggtctc cggggaagac ggtaaccatc    60
tcctgcaccc gcagcagtgg cagcattggc agcacctatg tgcagtggta ccaacagcgc   120
ccgggcagtc ccccaccac tgtgatctat aaggatgacc aaagaccctc tggggtccct    180
gatcggttct ctggctccat cgacggctcc tccaactctg cctccctcac catctctgga   240
ctggagactg aggacgaggc tgactactac tgtcagtctt ctgataccag caatctggtc   300
ttcggcggag ggaccaaggt caccgtccta                                    330
```

<210> SEQ ID NO 104
<211> LENGTH: 324
<212> TYPE: DNA
<213> ORGANISM: Homo sapiens

<400> SEQUENCE: 104

```
gaaactacac tcacgcagtc tccaggcacc ctgtctgttt ctccggggga aagagttacc    60
ctctcctgca gggccagtca gagtattagc ggtaattact tagcctggta ccagcagaga   120
cctggccagg ctcccaggct cctcatctat ggggcattca ggagggccac tggcatccca   180
gacaggttca gtggcagtgg gtctgggaca gacttcactc tcaccatcac cagactggag   240
cctgaagatt ttgcaactta ttactgccaa cactataata atttcccccca cactttcggc   300
gcagggacca agtggatat caaa                                           324
```

<210> SEQ ID NO 105
<211> LENGTH: 120
<212> TYPE: PRT
<213> ORGANISM: Homo sapiens

<400> SEQUENCE: 105

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Leu Glu Trp Met
        35                  40                  45

Gly Glu Ile Asn Pro Asn Asn Ala Arg Ile Asn Phe Asn Glu Lys Phe
    50                  55                  60

Lys Thr Arg Val Thr Leu Thr Val Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Thr Arg Gly Tyr Tyr Arg Tyr Gly Ala Trp Phe Gly Tyr Trp Gly Gln
            100                 105                 110

Gly Thr Leu Val Thr Val Ser Ser
        115                 120

<210> SEQ ID NO 106
<211> LENGTH: 107
<212> TYPE: PRT
<213> ORGANISM: Homo sapiens

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Tyr Ile Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly His Thr Leu Pro Trp
                85                  90                  95

Thr Phe Gly Gly Gly Thr Lys Val Glu Ile Lys
            100                 105

<210> SEQ ID NO 107
<211> LENGTH: 123
<212> TYPE: PRT
<213> ORGANISM: Homo sapiens

<400> SEQUENCE: 107

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu
        115                 120

<210> SEQ ID NO 108
<211> LENGTH: 5
<212> TYPE: PRT
<213> ORGANISM: Artificial Sequence
<220> FEATURE:
<223> OTHER INFORMATION: VH CDR1
```

```
<400> SEQUENCE: 108

Arg Ala Trp Met Asn
1               5

<210> SEQ ID NO 109
<211> LENGTH: 19
<212> TYPE: PRT
<213> ORGANISM: Artificial Sequence
<220> FEATURE:
<223> OTHER INFORMATION: VH CDR2

<400> SEQUENCE: 109

Arg Ile Lys Arg Lys Thr Asp Gly Glu Thr Thr Asp Tyr Ala Ala Pro
1               5                  10                  15

Val Lys Gly

<210> SEQ ID NO 110
<211> LENGTH: 7
<212> TYPE: PRT
<213> ORGANISM: Artificial Sequence
<220> FEATURE:
<223> OTHER INFORMATION: VH CDR3

<400> SEQUENCE: 110

Ser Asn Arg Ala Phe Asp Ile
1               5

<210> SEQ ID NO 111
<211> LENGTH: 17
<212> TYPE: PRT
<213> ORGANISM: Artificial Sequence
<220> FEATURE:
<223> OTHER INFORMATION: VL CDR1

<400> SEQUENCE: 111

Lys Ser Ser Gln Ser Val Leu Tyr Ala Gly Asn Asn Arg Asn Tyr Leu
1               5                  10                  15

Ala

<210> SEQ ID NO 112
<211> LENGTH: 7
<212> TYPE: PRT
<213> ORGANISM: Artificial Sequence
<220> FEATURE:
<223> OTHER INFORMATION: VL CDR2

<400> SEQUENCE: 112

Gln Ala Ser Thr Arg Ala Ser
1               5

<210> SEQ ID NO 113
<211> LENGTH: 9
<212> TYPE: PRT
<213> ORGANISM: Artificial Sequence
<220> FEATURE:
<223> OTHER INFORMATION: VL CDR3

<400> SEQUENCE: 113

Gln Gln Tyr Tyr Thr Pro Pro Leu Ala
1               5
```

CD47 MONOCLONAL ANTIBODIES AND USES THEREOF

CROSS REFERENCE TO RELATED APPLICATIONS

This application is a divisional application of U.S. application Ser. No. 15/761,309, filed on Mar. 19, 2018, now abandoned, which is the US national phase of International Application No. PCT/US2017/057535, filed on Oct. 20, 2017, which claims priority to International Application No. PCT/CN2016/102720, filed on Oct. 20, 2016, International Application No. PCT/CN2017/076462, filed on Mar. 13, 2017, and International Application No. PCT/CN2017/000329, filed on Apr. 27, 2017, the contents of all of which are incorporated herein in their entirety.

SEQUENCE LISTING

The present specification is being filed with an ASCII formatted copy of the Sequence Listing. The ASCII file is entitled "13371-224-999 Substitute_Sequence_Listing.TXT", which was created on Aug. 4, 2021 and is 100,486 bytes in size, is incorporated herein by reference in its entirety.

BACKGROUND OF THE INVENTION

CD47 (Cluster of Differentiation 47) was first identified as a tumor antigen on human ovarian cancer in the 1980s. Since then, CD47 has been found to be expressed on multiple human tumor types including acute myeloid leukemia (AML), chronic myeloid leukemia, acute lymphoblastic leukemia (ALL), non-Hodgkin's lymphoma (NHL), multiple myeloma (MM), bladder cancer, and other solid tumors. High levels of CD47 allow cancer cells to avoid phagocytosis despite having a higher level of calreticulin—the dominant pro-phagocytic signal.

Also known as integrin-associated protein (IAP), ovarian cancer antigen OA3, Rh-related antigen and MERG, CD47 is a multi-spanning transmembrane receptor belonging to the immunoglobulin superfamily. Its expression and activity have been implicated in a number of diseases and disorders. It is a broadly expressed transmembrane glycoprotein with a single Ig-like domain and five membrane spanning regions, which functions as a cellular ligand for SIRPα with binding mediated through the $NH_2$-terminal V-like domain of signal-regulatory-protein a (SIRPα). SIRPα is expressed primarily on myeloid cells, including macrophages, granulocytes, myeloid dendritic cells (DCs), mast cells, and their precursors, including hematopoietic stem cells.

Macrophages clear pathogens and damaged or aged cells from the blood stream via phagocytosis. Cell-surface CD47 interacts with its receptor on macrophages, SIRPα, to inhibit phagocytosis of normal, healthy cells. SIRPα inhibits the phagocytosis of host cells by macrophages, where the ligation of SIRPα on macrophages by CD47 expressed on the host target cell generates an inhibitory signal mediated by SHP-1 that negatively regulates phagocytosis.

In keeping with the role of CD47 to inhibit phagocytosis of normal cells, there is evidence that it is transiently up-regulated on hematopoietic stem cells (HSCs) and progenitors just prior to and during their migratory phase, and that the level of CD47 on these cells determines the probability that they are engulfed in vivo.

CD47 is also constitutively up-regulated on a number of cancers, including myeloid leukemias. Overexpression of CD47 on a myeloid leukemia line increases its pathogenicity by allowing it to evade phagocytosis. It has been concluded that CD47 up-regulation is an important mechanism for providing protection to normal HSCs during inflammation-mediated mobilization, and that leukemic progenitors co-opt this ability in order to evade macrophage killing.

Certain CD47 antibodies have been shown to restore phagocytosis and prevent atherosclerosis. See, e.g., Kojima et al., Nature, Vol. 36, 86-90 (Aug. 4, 2016). The present invention provides novel CD47 antibodies or immunologically active fragments thereof that have low immunogenicity in humans and cause low or no level of red blood cell depletion. As well known to a person skilled in the art, such antibodies may be interchangeably called "anti-CD47 antibodies."

SUMMARY OF THE PRESENT INVENTION

In one aspect, the present invention provides isolated monoclonal antibodies and their immunologically active fragments that bind to human CD47. For brevity, these CD47-binding isolated monoclonal antibodies and their immunologically active fragments are referred to hereinafter as "CD47 antibodies". The CD47 antibodies of this invention are capable of modulating, e.g., blocking, inhibiting, reducing, antagonizing, neutralizing or otherwise interfering with, CD47 expression, activity and/or signaling, or the interaction between CD47 and SIRPα. Very significantly, the CD47 antibodies of this invention do not generally cause a significant level of depletion or hemagglutination of human red blood cells, and surprisingly in many cases do not cause any depletion or hemagglutination of human red blood cells at all. Additionally, the CD47 antibodies of this invention have exhibited potent anti-tumor activities.

In some embodiments, the CD47 antibodies of this invention each include (a) a variable heavy (VH) chain sequence that is at least 90% (e.g., at least 95%) identical to an amino acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, and SEQ ID NO: 77; and (b) a variable light (VL) chain sequence that is at least 90% (e.g., at least 95%) identical to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, and SEQ ID NO: 78.

In some other embodiments, the CD47 antibodies of this invention each include paired VH/VL chain sequences that are at least 90% (e.g., at least 95%, 95%, 96, 97%, 98%, 99%, or 99.5%) identical to a pair of VH and VL amino acid sequences selected from the group consisting of SEQ ID NO: 1 and SEQ ID NO: 2 (i.e., 1A1), SEQ ID NO: 3 and SEQ ID NO: 4 (i.e., 1F8), SEQ ID NO: 5 and SEQ ID NO: 6 (i.e., 2A11), SEQ ID NO: 7 and SEQ ID NO: 8 (i.e., 2C2), SEQ ID NO: 9 and SEQ ID NO: 10 (i.e., 2D7), SEQ ID NO: 11 and SEQ ID NO: 12 (i.e., 2G4), SEQ ID NO: 13 and SEQ ID NO: 14 (i.e., 2G11), SEQ ID NO: 15 and SEQ ID NO: 16 (i.e., 6F4), SEQ ID NO: 17 and SEQ ID NO: 18 (i.e., 5H1), SEQ ID NO: 19 and SEQ ID NO: 20 (i.e., 5F6), SEQ ID NO: 21 and SEQ ID NO: 22 (i.e., 1F3), SEQ ID NO: 23 and SEQ ID NO: 24 (i.e., 2A4), SEQ ID NO: 25 and SEQ ID NO: 26 (i.e., 2B12), SEQ ID NO: 27 and SEQ ID NO: 28 (i.e., 13A11), SEQ ID NO: 29 and SEQ ID NO: 30 (i.e., 15E1), SEQ ID NO: 31 and SEQ ID NO: 32 (i.e., 13H3), SEQ ID NO: 33 and SEQ ID NO: 34 (i.e., 14A8), SEQ ID NO: 35 and SEQ ID NO: 36 (i.e., 16H3), SEQ ID NO: 37 and SEQ ID NO: 38 (i.e., 1A1), SEQ ID NO: 39 and SEQ ID NO: 40 (i.e., 1A1-A), SEQ ID NO: 41 and SEQ ID NO: 42 (i.e., 1A1-Q), SEQ ID NO: 43 and SEQ ID NO: 44 (i.e., 1A2), SEQ ID NO: 45 and SEQ ID NO: 46 (i.e., 1A8), SEQ ID NO: 47 and SEQ ID NO: 48 (i.e., 1B1), SEQ ID NO: 49 and SEQ ID NO: 50 (i.e., 1B2), SEQ ID NO: 51 and SEQ ID NO: 52 (i.e., 1H3), SEQ ID NO: 53 and SEQ ID NO: 54 (i.e., 1H3-Q), SEQ ID NO: 55 and SEQ ID NO: 56 (i.e., 1H3-A), SEQ ID NO: 57 and SEQ ID NO: 58 (i.e., 2A2), SEQ ID NO: 59 and SEQ ID NO: 60 (i.e., 2A3), SEQ ID NO: 61 and SEQ ID NO: 62 {i.e., 2A6), SEQ ID NO: 63 and SEQ ID NO: 64 (i.e., 2A10), SEQ ID NO: 65 and SEQ ID NO: 66 (i.e., 2B1), SEQ ID NO: 67 and SEQ ID NO: 68 (i.e., 2C6), SEQ ID NO: 69 and SEQ ID NO: 70 (i.e., 2E7), SEQ ID NO: 71 and SEQ ID NO: 72 (i.e., 2E9), SEQ ID NO: 73 and SEQ ID NO: 74 (i.e., 2F1), SEQ ID NO: 75 and SEQ ID NO: 76 (i.e., 2F3), and SEQ ID NO: 77 and SEQ ID NO: 78 (i.e., 34C5). In some instances, the CD47 antibodies of this invention each include a pair of VH and VL chain sequences selected from the group consisting of SEQ ID NO: 1 and SEQ ID NO: 2 (i.e., 1A1), SEQ ID NO: 3 and SEQ ID NO: 4 (i.e., 1F8), SEQ ID NO: 5 and SEQ ID NO: 6 (i.e., 2A11), SEQ ID NO: 7 and SEQ ID NO: 8 (i.e., 2C2), SEQ ID NO: 9 and SEQ ID NO: 10 (i.e., 2D7), SEQ ID NO: 11 and SEQ ID NO: 12 (i.e., 2G4), SEQ ID NO: 13 and SEQ ID NO: 14 (i.e., 2G11), SEQ ID NO: 15 and SEQ ID NO: 16 (i.e., 6F4), SEQ ID NO: 17 and SEQ ID NO: 18 (i.e., 5H1), SEQ ID NO: 19 and SEQ ID NO: 20 (i.e., 5F6), SEQ ID NO: 21 and SEQ ID NO: 22 (i.e., 1F3), SEQ ID NO: 23 and SEQ ID NO: 24 (i.e., 2A4), SEQ ID NO: 25 and SEQ ID NO: 26 (i.e., 2B12), SEQ ID NO: 27 and SEQ ID NO: 28 (i.e., 13A11), SEQ ID NO: 29 and SEQ ID NO: 30 (i.e., 15E1), SEQ ID NO: 31 and SEQ ID NO: 32 (i.e., 13H3), SEQ ID NO: 33 and SEQ ID NO: 34 (i.e., 14A8), SEQ ID NO: 35 and SEQ ID NO: 36 (i.e., 16H3), SEQ ID NO: 37 and SEQ ID NO: 38 (i.e., 1A1), SEQ ID NO: 39 and SEQ ID NO: 40 (i.e., 1A1-A), SEQ ID NO: 41 and SEQ ID NO: 42 (i.e., 1A1-Q), SEQ ID NO: 43 and SEQ ID NO: 44 (i.e., 1A2), SEQ ID NO: 45 and SEQ ID NO: 46 (i.e., 1A8), SEQ ID NO: 47 and SEQ ID NO: 48 (i.e., 1B1), SEQ ID NO: 49 and SEQ ID NO: 50 (i.e., 1B2), SEQ ID NO: 51 and SEQ ID NO: 52 (i.e., 1H3), SEQ ID NO: 53 and SEQ ID NO: 54 (i.e., 1H3-Q), SEQ ID NO: 55 and SEQ ID NO: 56 (i.e., 1H3-A), SEQ ID NO: 57 and SEQ ID NO: 58 (i.e., 2A2), SEQ ID NO: 59 and SEQ ID NO: 60 (i.e., 2A3), SEQ ID NO: 61 and SEQ ID NO: 62 (i.e., 2A6), SEQ ID NO: 63 and SEQ ID NO: 64 (i.e., 2A10), SEQ ID NO: 65 and SEQ ID NO: 66 (i.e., 2B1), SEQ ID NO: 67 and SEQ ID NO: 68 (i.e., 2C6), SEQ ID NO: 69 and SEQ ID NO: 70 (i.e., 2E7), SEQ ID NO: 71 and SEQ ID NO: 72 (i.e., 2E9), SEQ ID NO: 73 and SEQ ID NO: 74 (i.e., 2F1), SEQ ID NO: 75 and SEQ ID NO: 76 (i.e., 2F3), and SEQ ID NO: 77 and SEQ ID NO: 78 (i.e., 34C5).

The CD47 antibodies of this invention can be chimeric or humanized. They can prevent or significantly reduce human CD47 from interacting with SIRPα, or promotes macrophage-mediated phagocytosis of a CD47-expressing cell.

The CD47 antibodies of this invention do not cause a significant or noticeable level of hemagglutination or depletion of red blood cells, and in many cases they do not cause hemagglutination or depletion of red blood cells at all.

In another aspect, the present invention provides isolated bispecific monoclonal antibodies. Each of such isolated bispecific monoclonal antibodies comprises a first arm and a second arm, wherein the first arm comprises a first monoclonal antibody or immunologically active fragment thereof as described above which binds human CD47, and the second arm comprise a second monoclonal antibody that does not bind human CD47.

In some embodiments, the second arm in the isolated bispecific monoclonal antibodies binds to a cancer cell.

In some other embodiments, the bispecific monoclonal antibodies inhibit interaction between human CD47 and human SIRPα.

In still another aspect, the present invention provides pharmaceutical compositions each containing one of the CD47 antibodies of this invention or an isolated bispecific monoclonal antibody of this invention, and a pharmaceutically acceptable carrier or excipient.

As used herein, the term "pharmaceutically acceptable carrier or excipient" refers to a carrier or an excipient that is useful for preparing a pharmaceutical composition or formulation that is generally safe, non-toxic, and neither biologically nor otherwise undesirable. A carrier or excipient employed is typically one suitable for administration to human subjects or other mammals. In making the compositions, the active ingredient is usually mixed with, diluted by, or enclosed with a carrier or excipient. When the carrier or excipient serves as a diluent, it can be a solid, semi-solid, or liquid material, which acts as a vehicle, carrier, or medium for the active ingredient of the antibody.

Also within the scope of the present invention is a method for treating a disease in a human subject in need thereof, and the method includes administering to the subject a therapeutically effective amount of a CD47 antibody of this invention, a bispecific monoclonal antibody of this invention, or a pharmaceutical composition of this invention, and the disease is a cancer, a fibrotic disease, or any disease related to inhibition of phagocytosis. In some instance, the cancer can be selected from the group consisting of ovarian cancer, colon cancer, breast cancer, lung cancer, head and neck cancer, bladder cancer, colorectal cancer, pancreatic cancer, non-Hodgkin's lymphoma, acute lymphocytic leukemia, chronic lymphocytic leukemia, acute myeloid leukemia, chronic myelogenous leukemia, hairy cell leukemia (HCL), T-cell prolymphocyte leukemia (T-PLL), large granular lymphocytic leukemia, adult T-cell leukemia, multiple myeloma, melanoma, leiomyoma, leiomyosarcoma, glioma, glioblastoma, myelomas, monocytic leukemias, B-cell derived leukemias, T-cell derived leukemias, B-cell derived lymphomas, T-cell derived lymphomas, endometrial cancer, kidney cancer, melanoma, prostate cancer, thyroid cancer, cervical cancer, gastric cancer, liver cancer, and solid tumors; whereas the fibrotic disease can be selected from the group consisting of myocardial infarction, angina, osteoarthritis, pulmonary fibrosis, asthma, cystic fibrosis, bronchitis, and asthma. Examples of solid tumors include, e.g., endometrial cancer, thyroid cancer, cervical cancer, gastric cancer, breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors, and neuroblastic-derived CNS tumors. The disease related to inhibition of phagocytosis can be a cardiovascular disease (e.g., atherosclerosis, stroke, hypertensive heart disease, rheumatic heart disease, cardiomyopathy, heart arrhythmia, congenital heart disease, valvular heart disease, carditis, aortic aneurysms, peripheral artery disease, or venous thrombosis).

As used herein, the term "effective amount" refers to that amount of a CD47 antibody sufficient or required to effect treatment, prognosis or diagnosis of a disease associated with CD47 dependent signaling, as described herein, when administered to a subject. Therapeutically effective amounts of antibodies provided herein, when used alone or in combination, will vary depending upon the relative activity of the antibodies (e.g., promoting macrophage mediated phagocytosis of cancer cells expressing CD47) and depending upon the subject and disease condition being treated, the weight and age of the subject, the severity of the disease condition, the manner of administration and the like, which can readily be determined by one of ordinary skill in the art.

As used herein, the term "isolated" preceding a CD47 antibody of this invention means that the antibody is substantially free of other cellular material. In one embodiment, an isolated antibody is substantially free of other proteins from the same species. In another embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

Still within the scope of this invention are fusion proteins each comprising a first amino acid sequence and a second amino acid sequence, wherein the first amino acid sequence is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, or SEQ ID NO: 77, or an amino acid sequence that is at least 90% (e.g., at least 95%) identical thereto; and the second amino acid sequence is SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, or SEQ ID NO: 78, or an amino acid sequence that is at least 90% (e.g., at least 95%) identical thereto.

In some embodiments, a fusion protein of this invention includes a combination of the first amino acid sequence and the second amino acid sequence, and the combination of these two amino acid sequences is SEQ ID NO: 1 and SEQ ID NO: 2 (i.e., 1A1), SEQ ID NO: 3 and SEQ ID NO: 4 (i.e., 1F8), SEQ ID NO: 5 and SEQ ID NO: 6 (i.e., 2A11), SEQ ID NO: 7 and SEQ ID NO: 8 (i.e., 2C2), SEQ ID NO: 9 and SEQ ID NO: 10 (i.e., 2D7), SEQ ID NO: 11 and SEQ ID NO: 12 (i.e., 2G4), SEQ ID NO: 13 and SEQ ID NO: 14 (i.e., 2G11), SEQ ID NO: 15 and SEQ ID NO: 16 (i.e., 6F4), SEQ ID NO: 17 and SEQ ID NO: 18 (i.e., 5H1), SEQ ID NO: 19 and SEQ ID NO: 20 (i.e., 5F6), SEQ ID NO: 21 and SEQ ID NO: 22 (i.e., 1F3), SEQ ID NO: 23 and SEQ ID NO: 24 (i.e., 2A4), SEQ ID NO: 25 and SEQ ID NO: 26 (i.e., 2B12), SEQ ID NO: 27 and SEQ ID NO: 28 (i.e., 13A11), SEQ ID NO: 29 and SEQ ID NO: 30 (i.e., 15E1), SEQ ID NO: 31 and SEQ ID NO: 32 (i.e., 13H3), SEQ ID NO: 33 and SEQ ID NO: 34 (i.e., 14A8), SEQ ID NO: 35 and SEQ ID NO: 36 (i.e., 16H3), SEQ ID NO: 37 and SEQ ID NO: 38 (i.e., 1A1), SEQ ID NO: 39 and SEQ ID NO: 40 (i.e., 1A1-A), SEQ ID NO: 41 and SEQ ID NO: 42 (i.e., 1A1-Q), SEQ ID NO: 43 and SEQ ID NO: 44 (i.e., 1A2), SEQ ID NO: 45 and SEQ ID NO: 46 (i.e., 1A8), SEQ ID NO: 47 and SEQ ID NO: 48 (i.e., 1B1), SEQ ID NO: 49 and SEQ ID NO: 50 (i.e., 1B2), SEQ ID NO: 51 and SEQ ID NO: 52 (i.e., 1H3), SEQ ID NO: 53 and SEQ ID NO: 54 (i.e., 1H3-Q), SEQ ID NO: 55 and SEQ ID NO: 56 (i.e., 1H3-A), SEQ ID NO: 57 and SEQ ID NO: 58 (i.e., 2A2), SEQ ID NO: 59 and SEQ ID NO: 60 (i.e., 2A3), SEQ ID NO: 61 and SEQ ID NO: 62 (i.e., 2A6), SEQ ID NO: 63 and SEQ ID NO: 64 (i.e., 2A10), SEQ ID NO: 65 and SEQ ID NO: 66 (i.e., 2B1), SEQ ID NO: 67 and SEQ ID NO: 68 (i.e., 2C6), SEQ ID NO: 69 and SEQ ID NO: 70 (i.e., 2E7), SEQ ID NO: 71 and SEQ ID NO: 72 (i.e., 2E9), SEQ ID NO: 73 and SEQ ID NO: 74 (i.e., 2F1), SEQ ID NO: 75 and SEQ ID NO: 76 (i.e., 2F3), SEQ ID NO: 77 and SEQ ID NO: 78 (i.e., 34C5), or a combination that is at least 90% (e.g., at least 95%) identical thereto for each of the first and second amino acid sequences.

In some other embodiments, a fusion protein of this invention includes a combination of the first amino acid sequence and the second amino acid sequence, and the combination of these two amino acid sequences is SEQ ID NO: 1 and SEQ ID NO: 2 (i.e., 1A1), SEQ ID NO: 3 and SEQ ID NO: 4 (i.e., 1F8), SEQ ID NO: 5 and SEQ ID NO: 6 (i.e., 2A11), SEQ ID NO: 7 and SEQ ID NO: 8 (i.e., 2C2), SEQ ID NO: 9 and SEQ ID NO: 10 (i.e., 2D7), SEQ ID NO: 11 and SEQ ID NO: 12 (i.e., 2G4), SEQ ID NO: 13 and SEQ ID NO: 14 (i.e., 2G11), SEQ ID NO: 15 and SEQ ID NO: 16 (i.e., 6F4), SEQ ID NO: 17 and SEQ ID NO: 18 (i.e., 5H1), SEQ ID NO: 19 and SEQ ID NO: 20 (i.e., 5F6), SEQ ID NO: 21 and SEQ ID NO: 22 (i.e., 1F3), SEQ ID NO: 23 and SEQ ID NO: 24 (i.e., 2A4), SEQ ID NO: 25 and SEQ ID NO: 26 (i.e., 2B12), SEQ ID NO: 27 and SEQ ID NO: 28 (i.e., 13A11), SEQ ID NO: 29 and SEQ ID NO: 30 (i.e., 15E1), SEQ ID NO: 31 and SEQ ID NO: 32 (i.e., 13H3), SEQ ID NO: 33 and SEQ ID NO: 34 (i.e., 14A8), SEQ ID NO: 35 and SEQ ID NO: 36 (i.e., 16H3), SEQ ID NO: 37 and SEQ ID NO: 38 (i.e., 1A1), SEQ ID NO: 39 and SEQ ID NO: 40 (i.e., 1A1-A), SEQ ID NO: 41 and SEQ ID NO: 42 (i.e., 1A1-Q), SEQ ID NO: 43 and SEQ ID NO: 44 (i.e., 1A2), SEQ ID NO: 45 and SEQ ID NO: 46 (i.e., 1A8), SEQ ID NO: 47 and SEQ ID NO: 48 (i.e., 1B1), SEQ ID NO: 49 and SEQ ID NO: 50 (i.e., 1B2), SEQ ID NO: 51 and SEQ ID NO: 52 (i.e., 1H3), SEQ ID NO: 53 and SEQ ID NO: 54 (i.e., 1H3-Q), SEQ ID NO: 55 and SEQ ID NO: 56 (i.e., 1H3-A), SEQ ID NO: 57 and SEQ ID NO: 58 (i.e., 2A2), SEQ ID NO: 59 and SEQ ID NO: 60 (i.e., 2A3), SEQ ID NO: 61 and SEQ ID NO: 62 (i.e., 2A6), SEQ ID NO: 63 and SEQ ID NO: 64 (i.e., 2A10), SEQ ID NO: 65 and SEQ ID NO: 66 (i.e., 2B1), SEQ ID NO: 67 and SEQ ID NO: 68 (i.e., 2C6), SEQ ID NO: 69 and SEQ ID NO: 70 (i.e., 2E7), SEQ ID NO: 71 and SEQ ID NO: 72 (i.e., 2E9), SEQ ID NO: 73 and SEQ ID NO: 74 (i.e., 2F1), SEQ ID NO: 75 and SEQ ID NO: 76 (i.e., 2F3), or SEQ ID NO: 77 and SEQ ID NO: 78 (i.e., 34C5).

In still some other embodiments, a fusion protein of this invention can further include an additional protein—in addition to the first and second amino acid sequences. The additional protein is an antibody or a cytokine.

In yet still some other embodiments, a fusion protein of this invention can be conjugated with a small-molecule therapeutic agent (e.g., anti-cancer or anti-inflammation agent) or a marker (e.g., a biomarker or fluorescent marker).

In yet another aspect, the present invention provides immunodominant epitopes encoded by the CD47 gene comprising a recombinant protein containing conformationally a TNMEAQ loop (residues 26-31), T34, E35, L74, and an LTR hinge (residues 101-103) of CD47.

In yet still another aspect, the present invention provides biological molecules that specifically bind to a conformational epitope having an amino acid sequence comprising a TNMEAQ loop (residues 26-31), T34, E35, L74, and an LTR hinge (residues 101-103) of CD47, wherein the antibody can specifically bind to CD47.

As used herein, the term "biological molecules" is meant to include synthetic antibodies (monoclonal or bispecific), peptides, and biomimetic molecules. The term "biomimetic molecules" refers to molecules which are designed or developed to have structures or properties similar to or resembling those of naturally occurring large compounds such as proteins or nucleotides and which have a molecular weight of, e.g., at least 3,000, at least 5,000, or at least 10,000.

All references cited herein are incorporated by reference in their entirety.

BRIEF DESCRIPTIONS OF THE DRAWINGS

Figure 3A:
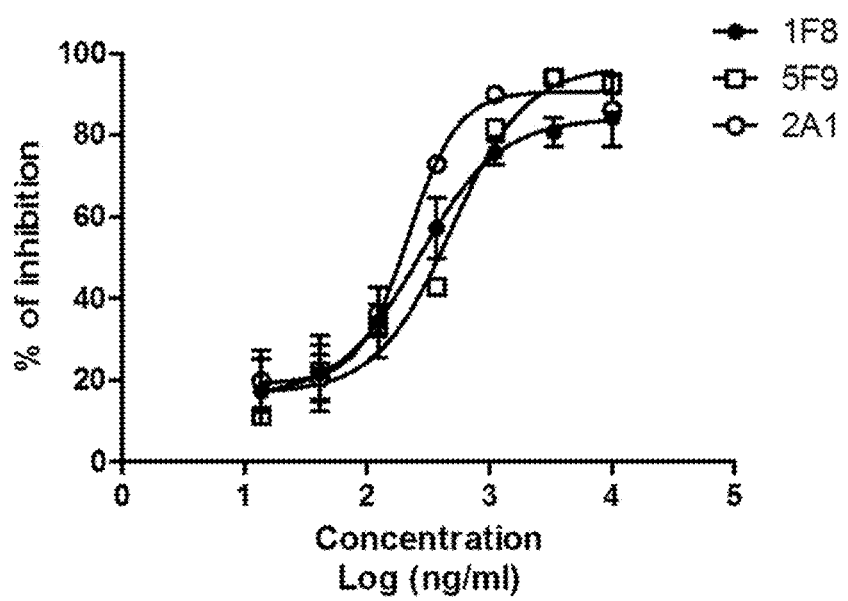
Figure 3B:
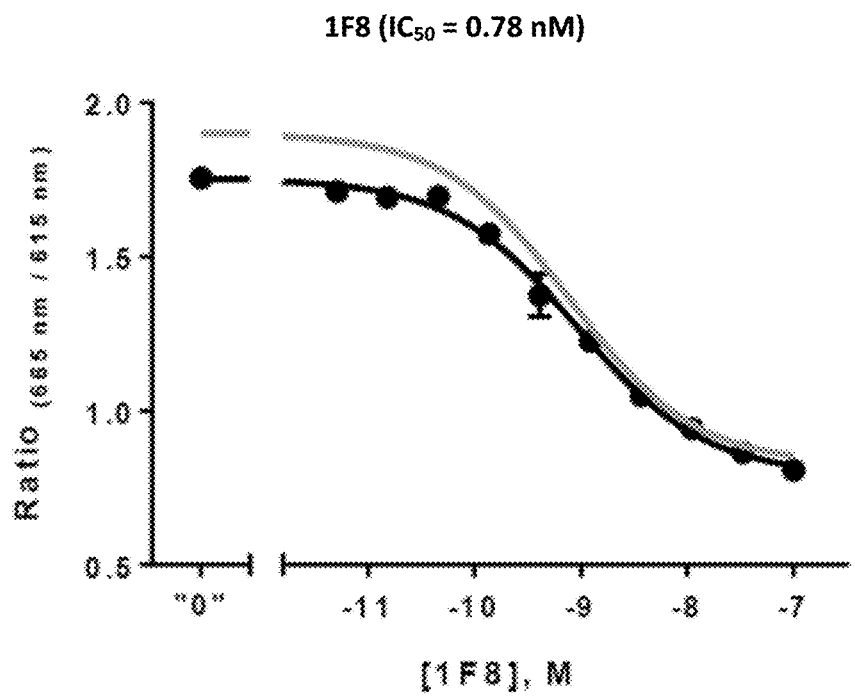
Figure 3C:
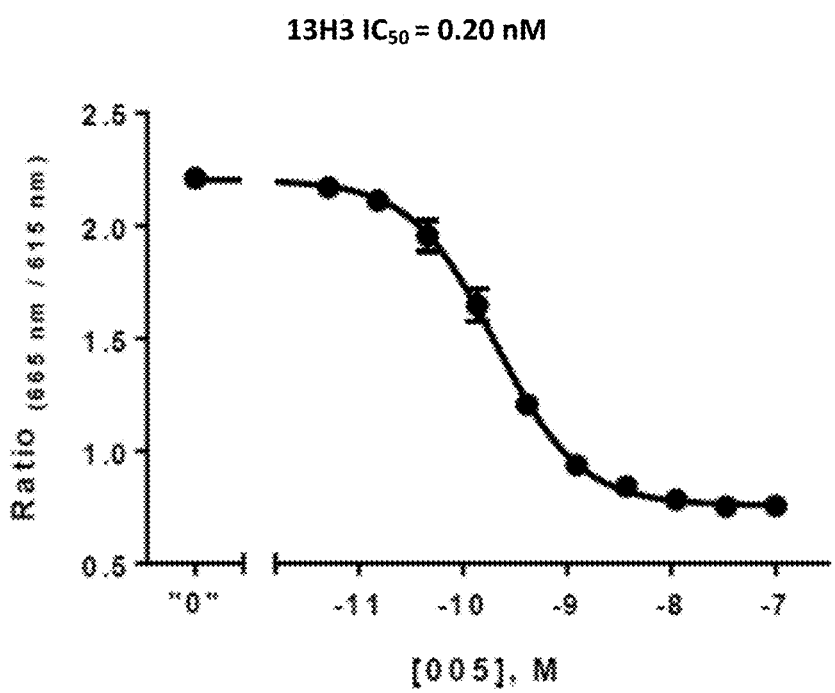

FIG. 3a, FIG. 3b, and FIG. 3c dose-dependent response of CD47 antibodies blocking the binding of CD47 to SIRPα.

Figure 4A:
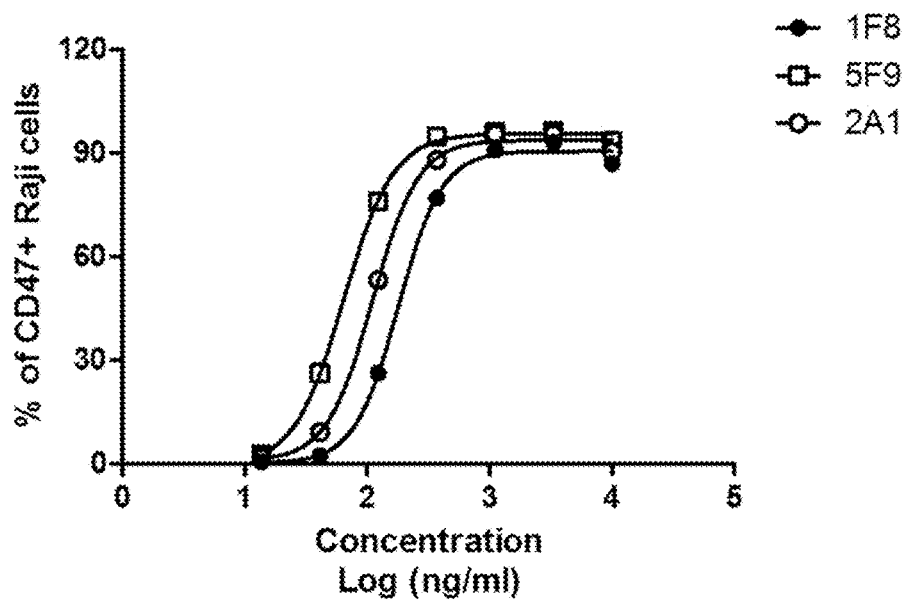
Figure 4B:
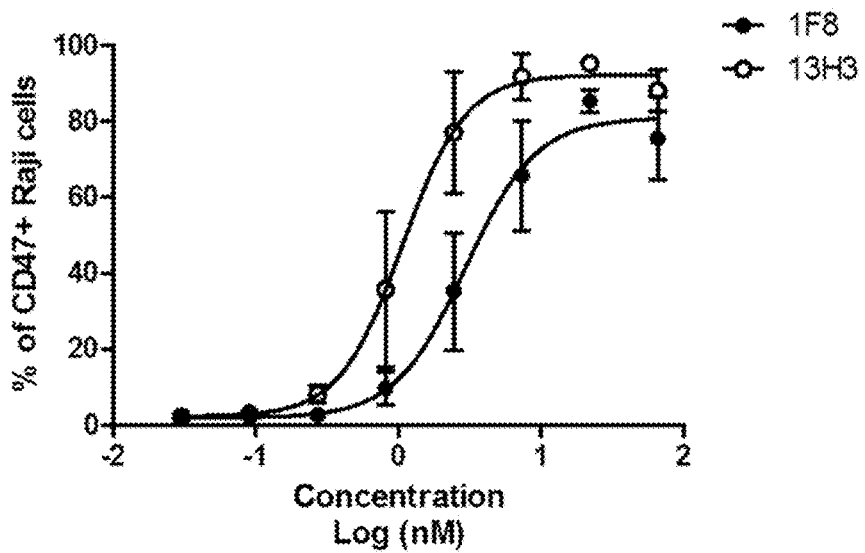
Figure 4C:
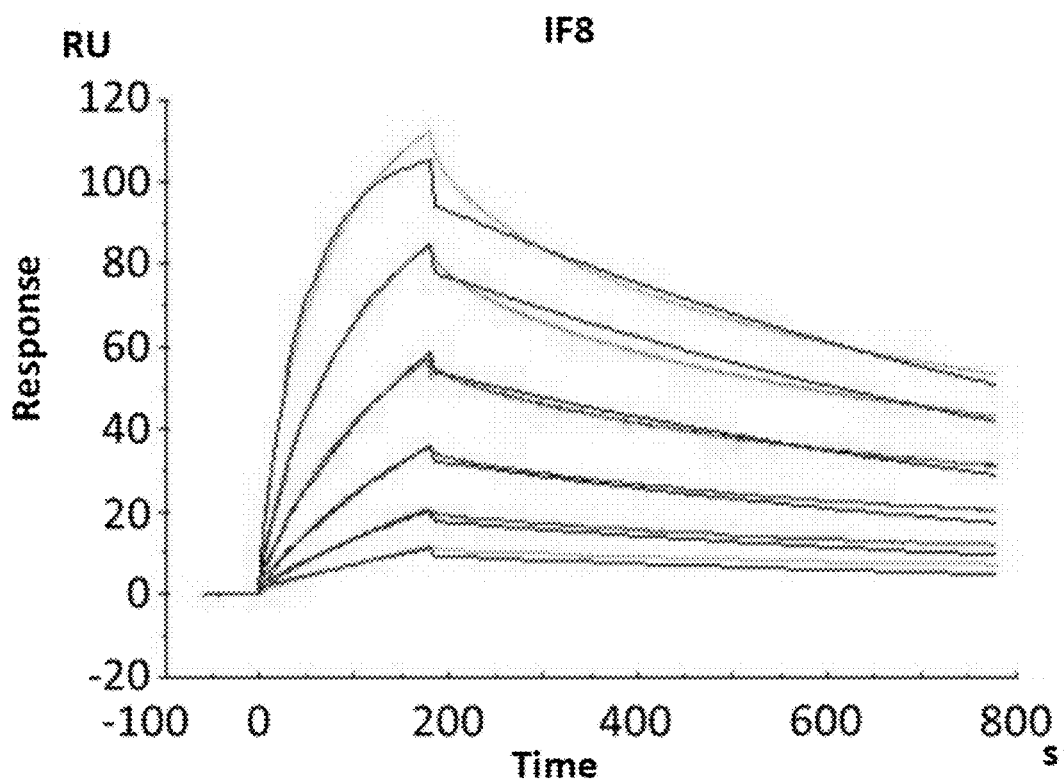
Figure 4D:
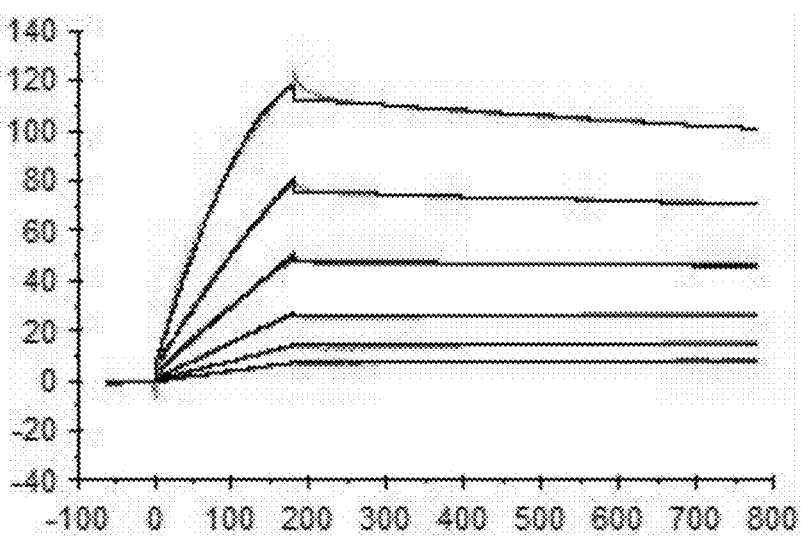

FIG. 4a and FIG. 4b show dose-dependent response of CD47 antibodies binding to CD47+ Raji cells; and FIG. 4c, FIG. 4d and FIG. 4e show binding kinetics and data of CD47 antibodies as measured by Biocore analysis.

FIG. 5a and FIG. 5b show phagocytosis of tumor cells by human MΦ with CD47 antibodies.

Figure 6A:
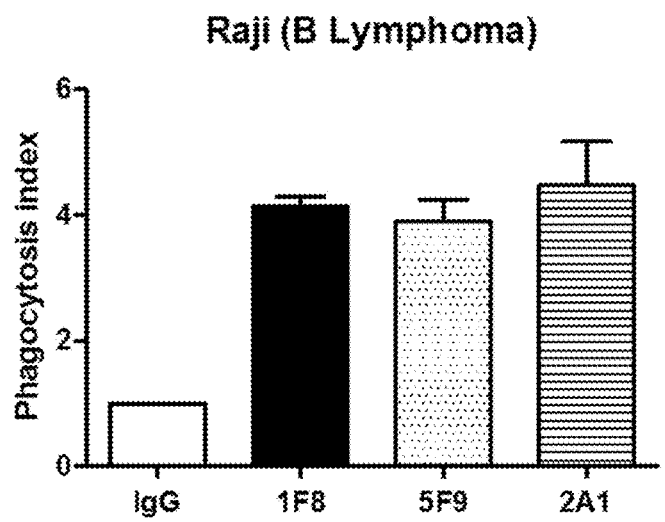
Figure 6B:
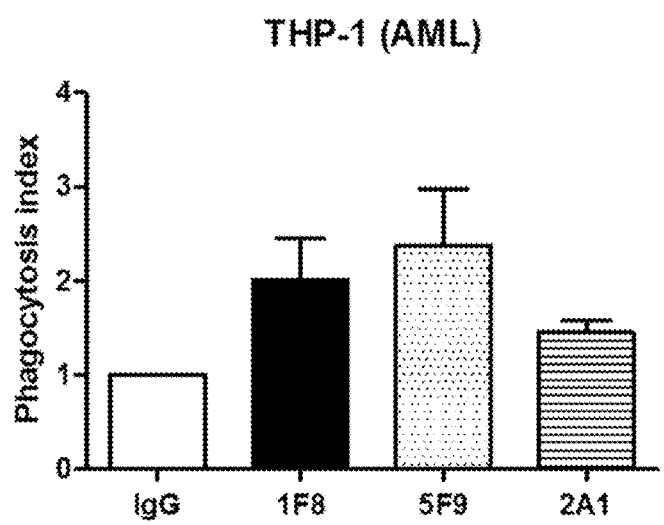
Figure 6C:
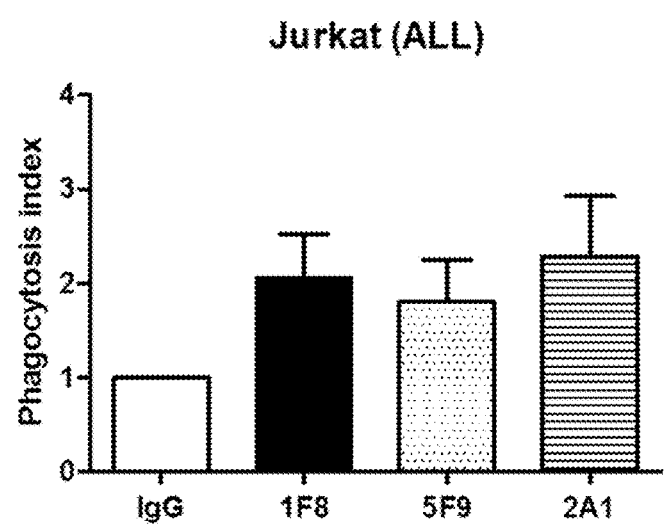

FIGS. 6a-6c show macrophage-mediated phagocytosis of various human blood cancer cell lines triggered by CD47 antibodies.

Figure 7A:
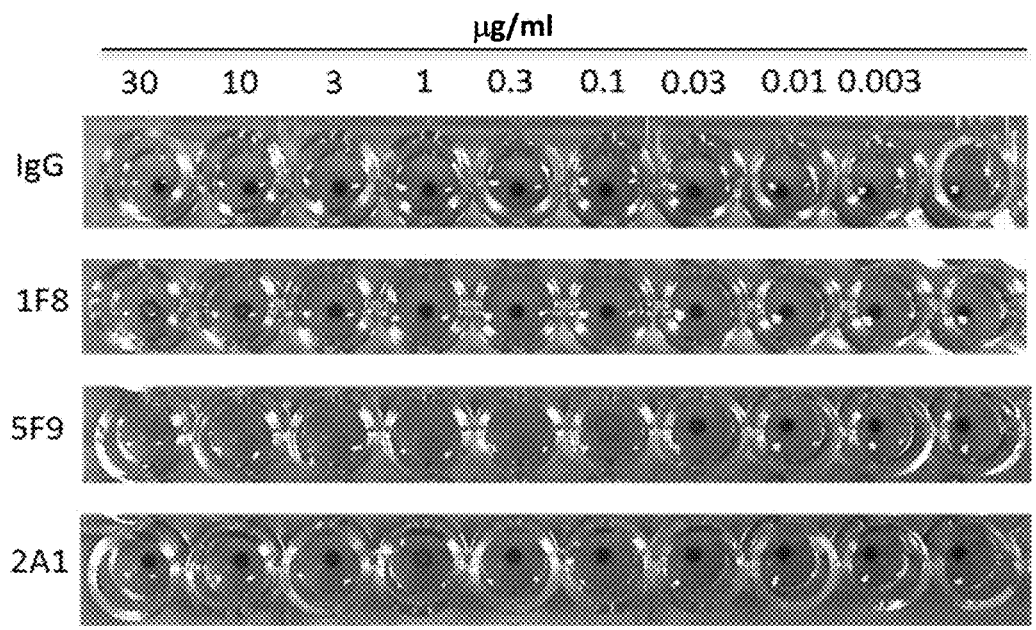
Figure 7B:
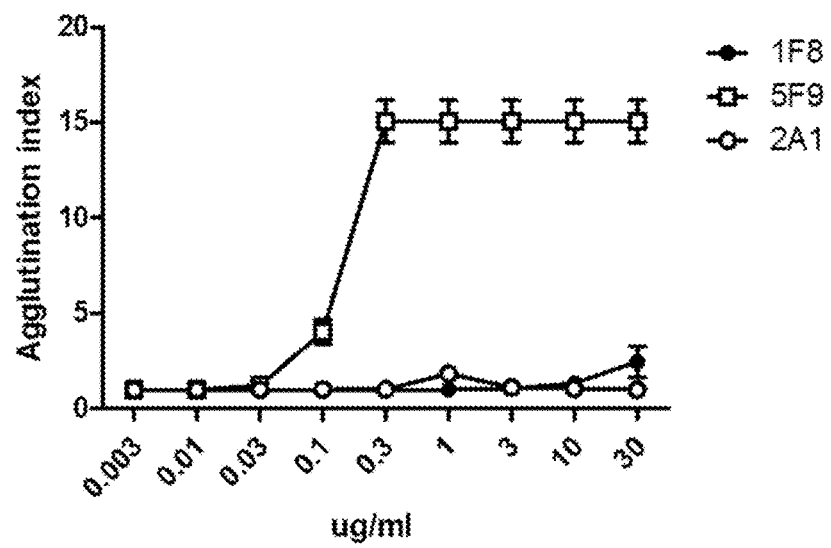

FIGS. 7a and 7b show red blood cells (RBC)-sparing properties in RBC agglutination assay with CD47 antibodies.

FIGS. 8a, 8b, 8c, and 8d show activities to bind RBC and induce RBC agglutination by CD antibodies at different and higher doses.

FIGS. 9a, 9b, 9c, and 9d show RBC-binding activities of CD47 antibodies.

FIG. 10 shows results of red blood cell agglutination across multiple human blood samples induced by CD47 antibodies.

Figure 11:
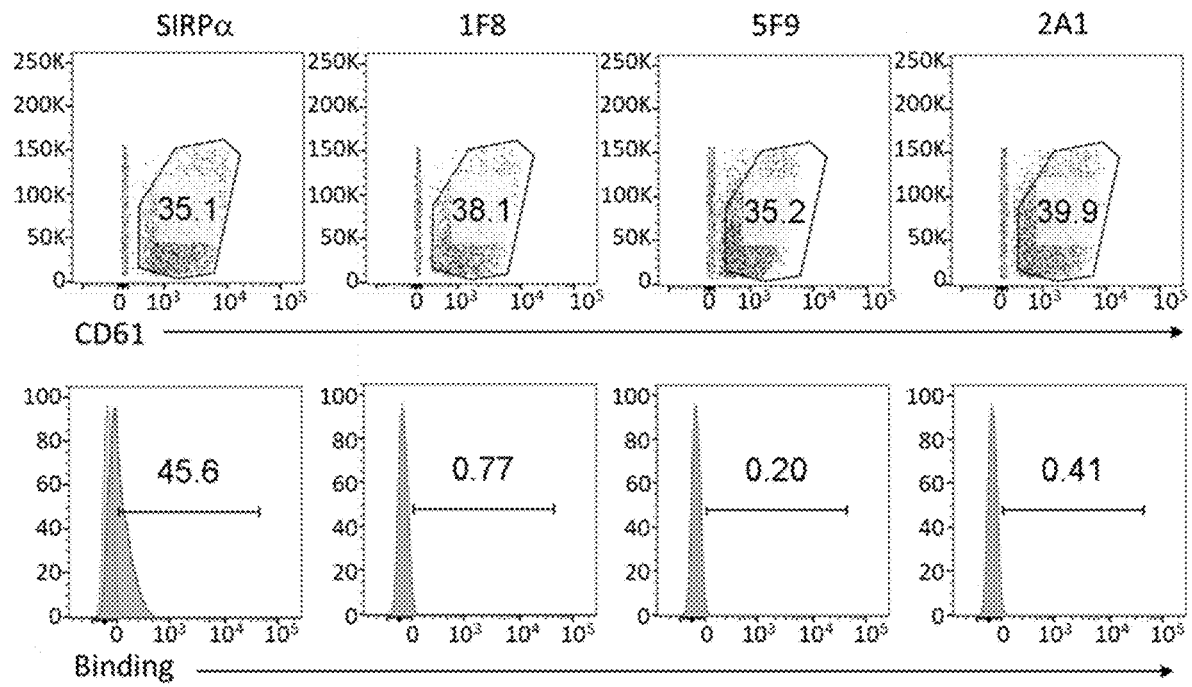

FIG. 11 shows the human platelet binding activities of CD47 antibodies and SIRPα-lg fusion, with CD61 stained as a surface marker for platelets.

FIG. 12 shows the test results of cyno red blood cell agglutination induced by CD47 antibodies and SIRPα-lg fusion in vitro.

FIG. 13 shows the test results of phagocytosis and AML cells binding by CD47 antibodies and control.

Figure 14B:
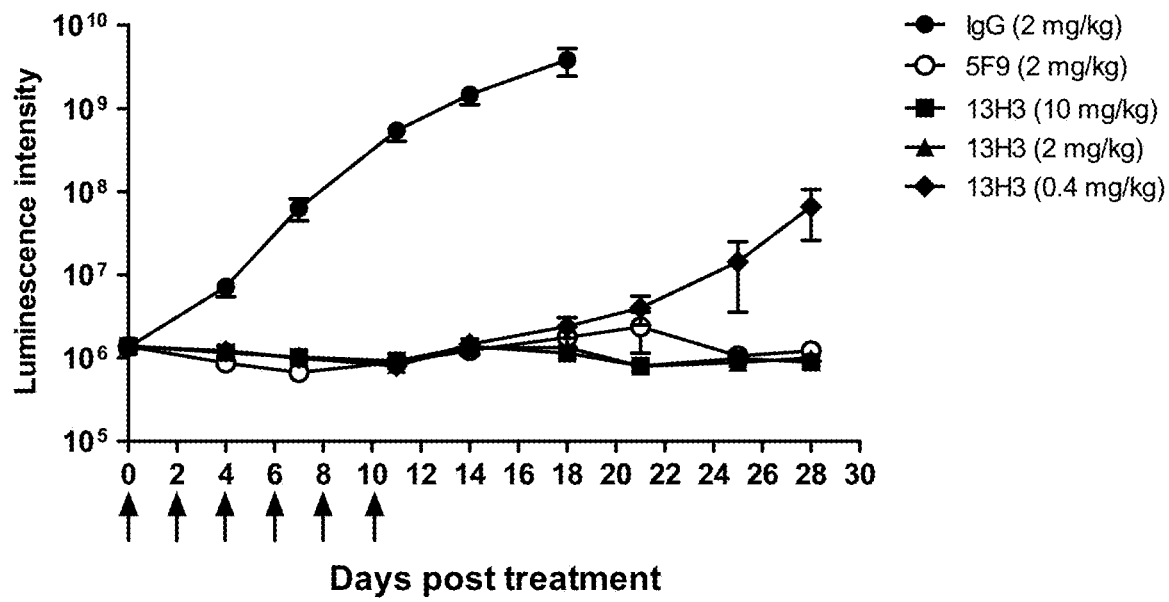

FIG. 14a and FIG. 14b show the efficacy of treatments with CD47 antibodies and control on luciferase-Raji xenograft mice.

FIG. 15 shows the polarization of macrophage in tumor-bearing mice induced by CD47 antibodies and control.

FIG. 16 shows the CD47 expression profiles using PDX samples of various human cancer types.

FIG. 17 shows results of safety pharm study (hematology) in cynomolgus monkeys.

FIG. 18 shows completion in binding of CD47 between antibodies 1F8 and 5F9, and between antibodies 1F8 and 2A1, due to their different epitopes, and structures of the 5F9/CD47 complex and the 1F8/CD47 complex.

FIGS. 19a, 19b, 19c, 19d, 19e, 19f, 19g, and 19h show the effects of the CD47 antibody 13H3 on RBC congregation, hemoglobin, platelets, and lymphocytes, respectively.

Figure 20:
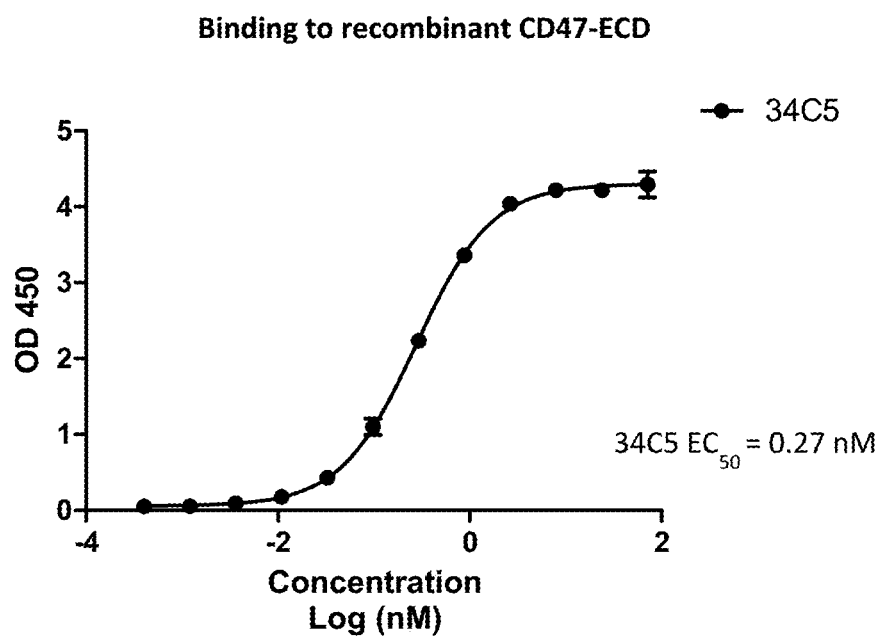

FIG. 20 shows strong binding affinity of 34C5 to recombinant CD47-ECD.

Figure 21:
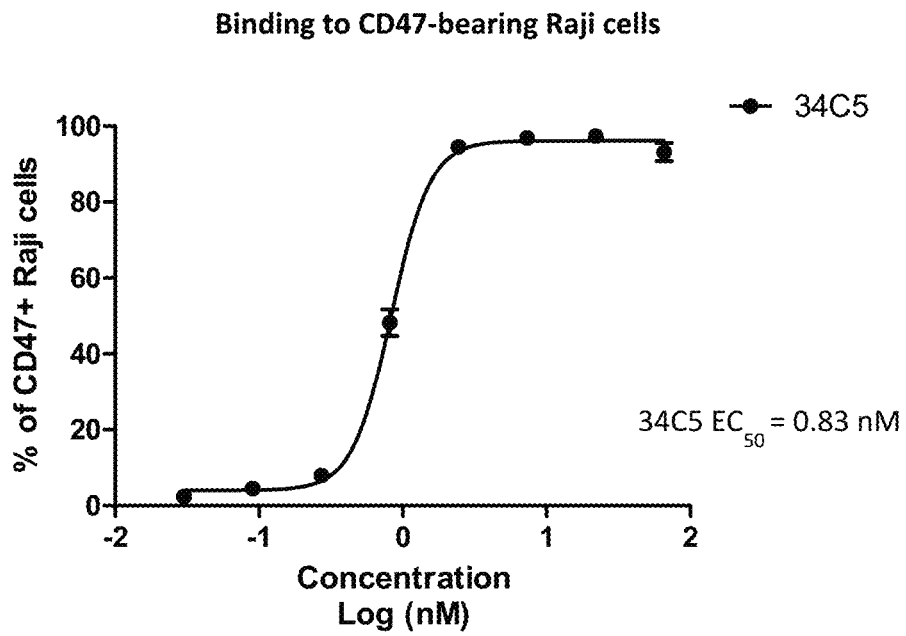

FIG. 21 shows strong binding affinity of 34C5 to CD47-bearing Raji cells.

Figure 22:
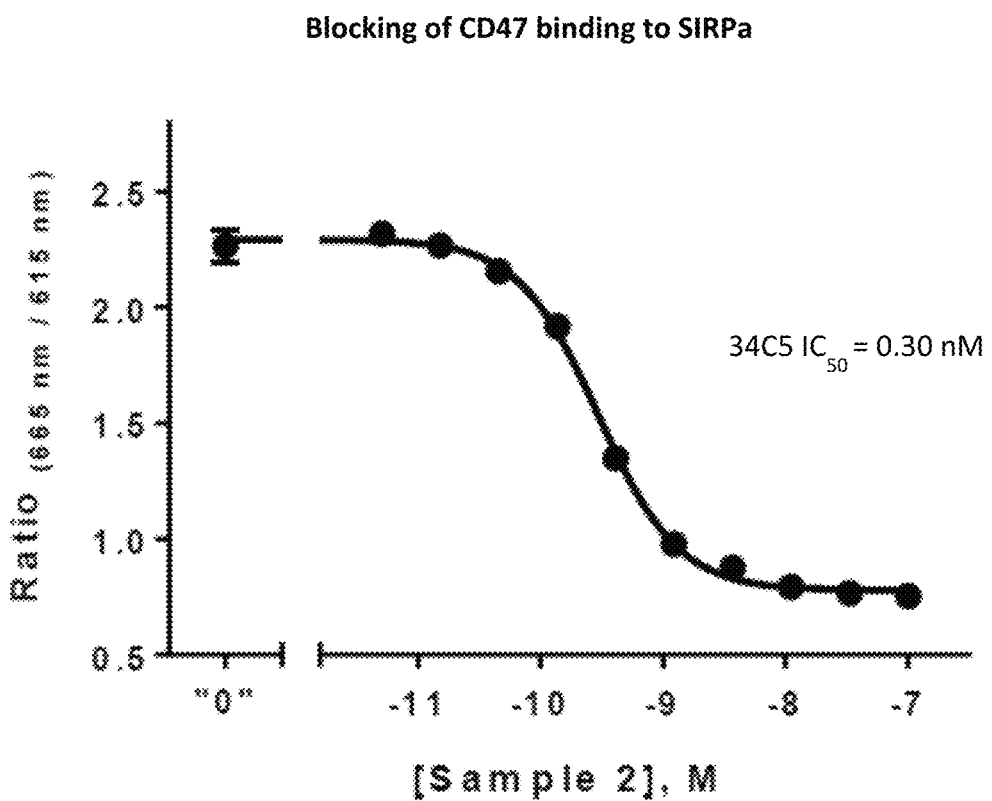

FIG. 22 shows that 34C5 was able to effectively block CD47 binding to SIRPα, with an $EC_{50}$ of 0.30 nM.

Figure 23:
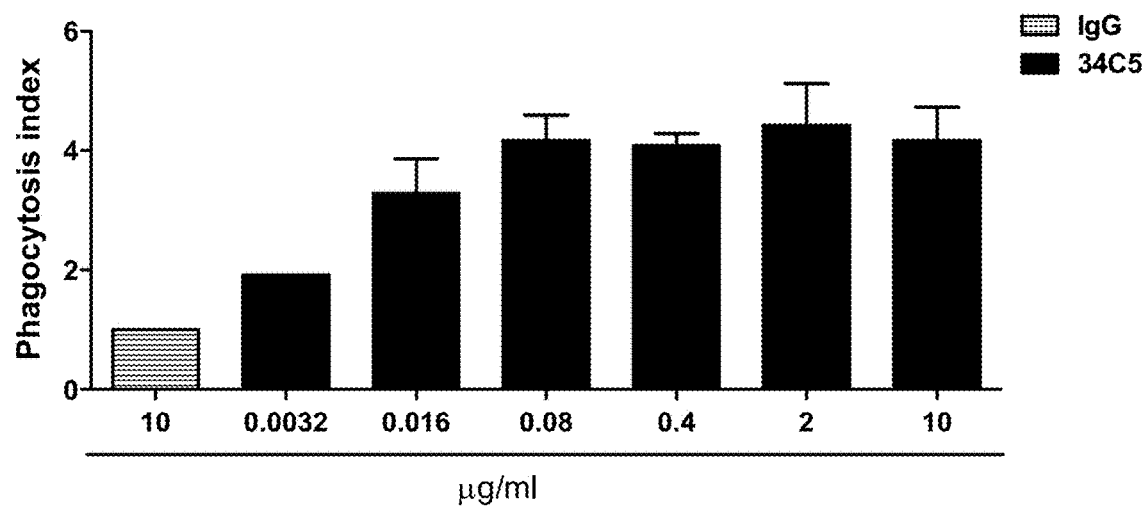

FIG. 23 shows that the antibody 34C5 promoted phagocystosis of tumor cells by human MED.

Figure 24:
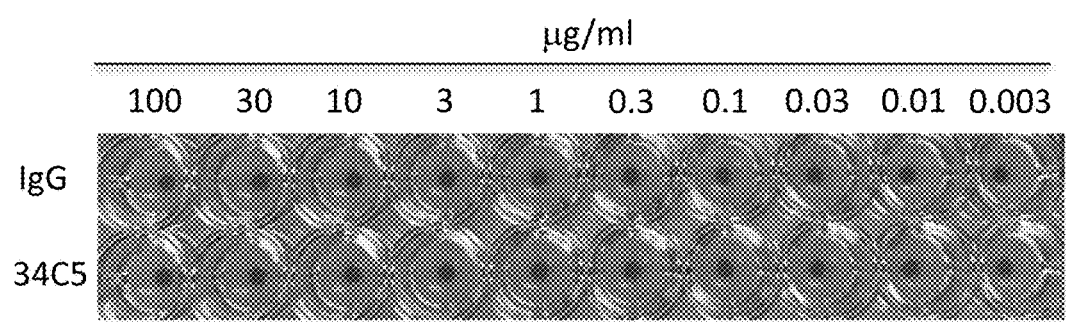

FIG. 24 shows the antibody 34C5 did not cause in vitro RBC agglutination.

Figure 25:
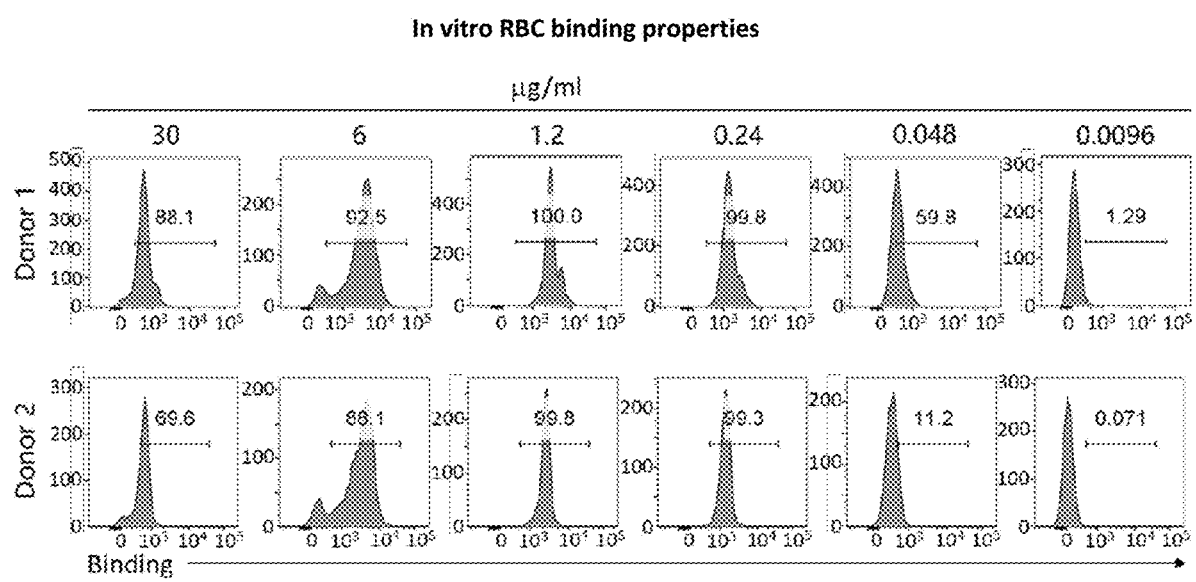

FIG. 25 shows the antibody 34C5 decrease its binding to RBC with the decreasing concentration of this antibody.

FIG. 26 shows amino acid sequences of some CD47 antibodies of this invention and their respective nucleotide sequences.

FIG. 27 shows the amino acid sequence for CD47 Immunoglobulin-like domain (Ig-V) 19-141.

DETAILED DESCRIPTION OF THE INVENTION

The present invention provides novel isolated monoclonal CD47 antibodies that can prevent human CD47 from interacting with SIRPα, or promote macrophage-mediated phagocytosis of a CD47-expressing cell. These CD47 antibodies do not cause a significant or noticeable level of hemagglutination or depletion of red blood cells, and in many cases they do not cause hemagglutination or depletion of red blood cells at all.

As examples, a CD47 antibodies of this invention would include (a) a variable heavy (VH) chain sequence that is at least 90% (e.g., at least 95%) identical to an amino acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, and SEQ ID NO: 77; and (b) a variable light (VL) chain sequence that is at least 90% (e.g., at least 95%) identical to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, and SEQ ID NO: 78. In some further instance, a CD47 antibodies of this invention would include a combined VH/VL chain sequence that is at least 90% (e.g., at least 95%) identical to an amino acid sequence selected from the group consisting of SEQ ID NO: 1 and SEQ ID NO: 2, SEQ ID NO: 3 and SEQ ID NO: 4, SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, SEQ ID NO: 35 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, SEQ ID NO: 59 and SEQ ID NO: 60, SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 76, and SEQ ID NO: 77 and SEQ ID NO: 78.

In certain emobidments, the CD47 antibody provided herein comprises (i) two heavy chains each of said heavy chains comprising a VH CDR1, a VH CDR2, and a VH CDR3 as set forth in a variablle heavy (VH) chain region comprising the amino acid sequence of SEQ ID NO: 31, and (ii) two light chains each of said light chains comprising a VL CDR1, a VL CDR2, and a VL CDR3 as set forth in a variable light (VL) chain region comprising the amino acid sequence of SEQ ID NO: 32, and wherein the VH CDR1, the VH CDR2, the VH CDR3, the VL CDR1, the VL CDR2, and the VL CDR3 are according to Kabat numbering scheme. In certain embodiments, the amino acid sequence of VH CDR1 according to Kabat numbering scheme is RAWMN (SEQ ID NO: 108), the amino acid sequence of VH CDR2 according to Kabat numbering scheme is RIKRKTDGETTDYAAPVKG (SEQ ID NO: 109); the amino acid sequence of VH CDR3 according to Kabat numbering scheme is SNRAFDI (SEQ ID NO: 110); the amino acid sequence of VL CDR1 according to Kabat numbering scheme is KSSQSVLYAGNNRNYLA (SEQ ID NO: 111); the amino acid sequence of VL CDR2 according to Kabat numbering scheme is QASTRAS (SEQ ID NO: 112); and the amino acid sequence of VL CDR3 according to Kabat numbering scheme is QQYYTPPLA (SEQ ID NO: 113).

As used herein, the term "antibody" is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity. "Antibodies'" (or "Abs") and "immunoglobulins" (or "Igs") are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used herein, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

As used herein, the term "native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond (also termed a "VH/VL pair"), while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains. See, e.g., Clothia et al., *J. Mol. Biol.*, 186:651 (1985); Novotny and Haber, *Proc. Natl. Acad. Sci. USA.*, 82:4592 (1985).

As used herein, the term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. See, e.g., Kabat et al., *Sequences of Proteins of Immunological Interest*, Fifth Edition, National Institute of Health, Bethesda, Md. (1991). The constant domains are not involved directly in binding an antibody to an antigen, but exhibit various effector functions, such as participation of the antibody in antibody-dependent cellular toxicity. Variable region sequences of interest include the provided humanized variable region sequences for CD47 antibodies. For instance, 1A1 includes SEQ ID NO: 1 (heavy) and SEQ ID NO: 2 (light), 1F8 includes SEQ ID NO: 3 (heavy) and SEQ ID NO: 4 (light), and 2A11 includes SEQ ID NO: 5 (heavy) and SEQ ID NO: 6 (light).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. See, e.g., Pluckthun, in *The Pharmacology of Monoclonal Antibodies*, Vol. 113, Rosenburg and Moore eds., Springer-Verlag, New York, pp. 269-315 (1994).

The Fab fragment also contains the constant domain of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG1, IgG2, IgG3, lgG4, IgA1, lgA2. The heavy-chain constant domains that correspond to the different classes of immunoglobulins are called α, δ, ε, γ, and μ, respectively. The subunit structures and three-dimensional configurations of different classes of immunoglobulins are well known.

As used herein, the term "antibody fragment", and all grammatical variants thereof, are defined as a portion of an intact antibody comprising the antigen binding site or variable region of the intact antibody, wherein the portion is free of the constant heavy chain domains (i.e. $CH_2$, $CH_3$, and $CH_4$, depending on antibody isotype) of the Fc region of the intact antibody. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules, (2) single chain polypeptides containing only one light chain variable domain, or a fragment thereof that contains the three CDRs of the light chain variable domain, without an associated heavy chain moiety, and (3) single chain polypeptides containing only one heavy chain variable region, or a fragment thereof containing the three CDRs of the heavy chain variable region, without an associated light chain moiety; and multi-specific or multivalent structures formed from antibody fragments. In an antibody fragment comprising one or more heavy chains, the heavy chain(s) can contain any constant domain sequence (e.g. CHI in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" used herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is polyethylenglycol (PEG). In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

As used herein, the term "monoclonal antibody" (mAb) refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The monoclonal antibodies herein include hybrid and recombinant antibodies produced by splicing a variable (including hypervariable) domain of an CD47 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')2, and Fv), so long as they exhibit the desired biological activity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

As used herein, an "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "epitope tagged" refers to a CD47 antibody fused to an "epitope tag". The epitope tag polypeptide has enough residues to provide an epitope against which an antibody can be made, yet is short enough such that it does not interfere with activity of the CD47 antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (see, e.g., Evan et al., *Mol. Cell. Biol.*, 5(12):3610-3616 (1985)); and the Herpes Simplex virus glycoprotein D (gD) tag and its antibody (see, e.g., Paborsky et al., *Protein Engineering*, 3(6):547-553 (1990)).

As used herein, the term "label" refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

As used herein, the term "solid phase" refers to a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles. See, e.g., U.S. Pat. No. 4,275,149.

The present invention also provides pharmaceutical compositions containing these CD47 antibodies and methods for treating diseases in a subject with these CD47 antibodies or pharmaceutical compositions.

As used herein, the term "treatment" or "treating" refers to both therapeutic treatment and prophylactic or preventative measures of a disease (such as cancer or a fibrotic disease). Those in need of treatment include those already with the disease as well as those in which the disease is to be prevented.

Examples of cancer include, but are not limited to, ovarian cancer, colon cancer, breast cancer, lung cancer, head and neck cancer, bladder cancer, colorectal cancer, pancreatic cancer, non-Hodgkin's lymphoma, acute lymphocytic leukemia, chronic lymphocytic leukemia, acute myeloid leukemia, chronic myelogenous leukemia, multiple myeloma, melanoma, leiomyoma, leiomyosarcoma, glioma, glioblastoma, myelomas, monocytic leukemias, B-cell derived leukemias, T-cell derived leukemias, B-cell derived lymphomas, T-cell derived lymphomas, and solid tumors. The fibrotic disease can be, e.g., myocardial infarction, angina, osteoarthritis, pulmonary fibrosis, asthma, cystic fibrosis, bronchitis, or asthma.

As used herein, the term "subject" for purposes of treatment refers to any animal classified as a mammal, including humans, domestic and farm animals, and zoo, sports, or pet animals, such as dogs, horses, cats, cows, etc. Preferably, the mammal is human.

The CD47 antibodies of this invention can also be used in vitro and in vivo to monitor the course of CD47 disease therapy. Thus, for example, by measuring the increase or decrease in the number of cells expressing CD47, particularly cancer cells expressing CD47, it can be determined whether a particular therapeutic regimen aimed at ameliorating disease is effective.

The CD47 antibodies of this invention may be used in vitro in immunoassays in which they can be utilized in liquid phase or bound to a solid phase carrier. In addition, the CD47 antibodies in these immunoassays can be detectably labeled in various ways. Examples of types of immunoassays which can utilize monoclonal antibodies of the invention are flow cytometry, e.g. FACS, MACS, immunohistochemistry, competitive and non-competitive immunoassays in either a direct or indirect format. Detection of the antigens using the CD47 antibodies of this invention can be done utilizing immunoassays which are run in either the forward, reverse, or simultaneous modes, including immunohistochemical assays on physiological samples. Those of skill in the art will know, or can readily discern, other immunoassay formats without undue experimentation.

The CD47 antibodies of the invention can be bound to many different carriers and used to detect the presence of CD47 expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art, which find use as tracers in therapeutic methods, for use in diagnostic methods, and the like. For diagnostic purposes a label may be covalently or non-covalently attached to an antibody of the invention or a fragment thereof, including fragments consisting or comprising of CDR sequences. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

In some embodiments, a CD47 antibody of this invention is attached to a nanoparticle, e.g. for use in imaging. Useful nanoparticles are those known in the art, for example including without limitation, Raman-silica-gold-nanoparticle (R-Si—Au-NP). The R-Si—Au-NPs consist of a Raman organic molecule, with a narrow-band spectral signature, adsorbed onto a gold core. Because the Raman organic molecule can be changed, each nanoparticles can carry its own signature, thereby allowing multiple nanoparticles to be independently detected simultaneously by multiplexing. The entire nanoparticle is encapsulated in a silica shell to hold the Raman organic molecule on the gold nanocore. Optional polyethylene glycol (PEG)-ylation of R-Si—Au-NPs increases their bioavailability and provides functional "handles"' for attaching targeting moieties. See, e.g., Thakor et al (2011), *Sci. Transl. Med.*, 3(79):79ra33; Jokerst et al. (2011) *Small.*, 7(5):625-33; Gao et al. (2011) Biomaterials, 32(8):2141-8.

For purposes of the invention, CD47 may be detected by the CD47 antibodies of this invention when present in biological fluids and on tissues, in vivo or in vitro. Any sample containing a detectable amount of CD47 can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As a matter of convenience, a CD47 antibody of this invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic formulations comprising one or more antibodies of the invention are prepared for storage by mixing the antibody having the desired degree of purity with optional physiologically acceptable carriers, excipients or stabilizers (see, e.g., Remington's Pharmaceutical Sciences, 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the CD47 associated disease.

The therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g., intraperitoneal (I.P.), intravenous (I.V.), intradermal (I.D.), intramuscular (I.M.), and the like.

A CD47 antibody of this invention needs not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients containing CD47 antibodies may also be entrapped in microcapsule prepared, e.g., by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

A CD47 antibody or pharmaceutical composition of this invention can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the anti-CD47 antibody is suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (e.g., the container may be an intravenous solution bag or a vial having a stopper pierceable by a hypodermic injection needle). The active agent in the composition is the anti-CD47 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Establishment of Phage Library

CD47 is a 50 kDa membrane receptor that has extracellular N-terminal IgV domain, five transmembrane domains, and a short C-terminal intracellular tail. Human CD47-lgV domain protein conjugated with human Fc or Biotinylated human CD47-lgV domain protein (ACROBiosystems) was used as antigen for phage library panning.

The phage library was constructed using phagemid vectors which consisted of the antibody gene fragments that were amplified from spleens or bone marrows of >50 healthy human subjects. The antibody format is single chain variable fragment (VH+linker+VL). The library size was 1.1×1010 and the sequence diversity was analyzed as follows. For the 62 clones picked up from the library and further sequenced, 16 sequences have truncation, frameshift or amber codon; 46 sequences have full length scFv of which all the HCDR3 sequences are unique. In the 46 full length scFv, 13 sequences have lambda light chain and 33 sequences have kappa light chain.

Phage Panning and Clone Selection

To obtain phage clones that specifically bind to the human CD47-lgV domain, two methods for phage panning were used.

1. Phage Library Immunotube Panning Against Human CD47-lgV

In this method, the phage libraries developed as described above were first incubated in casein-coated immunotube for 2 hours. The human CD47-lgV-Fc fusion protein was used for first round of panning. Unbound phages were removed by washing with PBST for 5-20 times. The bound phages were eluted with freshly prepared 100 mM Triethylamine solution and neutralized by addition a Tris-HCl buffer, to become the first output phage pools. This first output phage pool was rescued through infection of E. Coli TG-1 cells for amplification, followed by the second round of panning using biotinylated human CD47-lgV as antigen. The bound phages were eluted in the same process and became the second output phage pool which was then rescued and then again followed by the third round of panning using human CD47-lgV-Fc fusion protein as antigen. The bound phages then became the third output phage pool and underwent the fourth round of panning using biotinylated human CD47-lgV.

2. Phage Library Solution Panning Against Human CD47-lgV

In this second method, the phage libraries were first incubated in casein-blocked 100 μi streptavdin-magnetic beads to deplete streptavdin beads binders. The streptavidin-magnetic beads and AG0084-hulgGl/k were used for negative depletion. The depleted library was rescued, which was followed by the second round of panning using biotinylated human CD47-lgV as antigens and further underwent negative depletion with casein blocked streptavdin-magnetic beads. The unbound phages were removed by washing with PBST for 5-20 times. The bound phages were eluted with a freshly prepared 100 mM Triethylamine solution, neutralized by addition of a Tris-HCl buffer, and then rescued, which was followed by the third round of panning using human CD47-lgV-Fc fusion protein and depleted with AG0084-hulgGl/k. The bound phages then become the third output phage pool and underwent the fourth round of panning using biotinylated human CD47-lgV and negative depletion with casein blocked streptavdin-magnetic beads.

After this process, multiple phage clones that specifically bound to the human CD47-IgV domain were obtained and enriched. They were then diluted and plated to grow at 37° C. for 8 hours and captured by anti-kappa antibody-coated filter overnight. Biotinylated human CD47-lgV (50 nM) and NeutrAvidin-AP conjugate (1:1000 dilution) were applied to the filter to detect the positively bound phage clones. Positive phage plaques were picked and eluted into 100 μL of phage elution buffer. About 10-15 μL eluted phages were used to infect 1 mL XL1 blue cells to make high titer phage (HT) for Phage single point ELISA (SPE). The positive single clones picked from the filer lift were subjected to the binding of human CD47-lgV-Fc fusion protein and biotinylated human CD47-lgV domain protein. These positive single clones were also sequenced for their VH and VL genes. All the positive hits with unique VH and VL genes were cloned into expression vectors pFUSE2ss-CLIg-hk (light chain, InvivoGen, Cat No. pfuse2ss-hclk) and pFUSEss-CHIg-hG1 (heavy chain, InvivoGen, Cat No. pfusess-hchg1). The antibodies were expressed in HEK293 cells and purified by Protein A Plus Agarose.

Affinity Maturation of CD-47 Antibodies

Binding affinity of the CD-47 antibodies of this invention can be improved by in vitro affinity maturation, e.g., by site-specific randomized mutation, which resulted in mutated sequences that are also within the scope of this invention.

For example, BiaCore analysis of 1F8, a CD47 antibody of this invention, showed a binding affinity (KD) of 2.8 nM with a high dissociation rate of 1.04E-03 1/s, which could be improved by in vitro affinity maturation. An extensive analysis of the CDR sequence of heavy chain and light chain of 1F8 identified several residues in HCDR1 and LCDR1 regions that could be randomized mutated. Therefore, the random mutagenesis libraries can be constructed and introduced into the specific residues to generate a variety of new sequences. The CDR mutagenesis libraries are panned using biotinylated soluble CD47 ECD in solution phase under the equilibrium condition. After multiple rounds of panning with reduced antigen concentration, enriched output binders are selected for the binding ELISA test and subsequent converted into full IgGs which are subjected to the BiaCore analysis to specifically select for the off-rate improved sequence. Through this screening process, antibody molecules of this invention can be constructed for overall best properties for clinical applications.

Example 1. ELISA Screening of Phage Clones Binding to Recombinant CD47-ECD Protein Recombinant human CD47-Fc fusion protein (Acrobiosystems) was coated at 2 ug/mL in phosphate buffer saline (PBS) onto microtiter plates for 2 hours at the room temperature (RT). After coating of antigen, the wells were blocked with PBS/0.05% Tween (PBST) with 1% BSA for 1 hour at the room temperature (RT). After washing of the wells with PBST, purified phages from single clones were added to the wells and incubated for 1 hour at RT. For detection of the binding phage clones, the HRP conjugated secondary antibodies against M13 (Jackson Immuno Research) were added, followed by the addition of fluorogenic substrates (Roche). Between all incubation steps, the wells of the plate were washed with PBST three times. Fluorescence was measured in a TECAN Spectrafluor plate reader. The positive phage clones were selected for sequencing of the heavy chain and light chain genes.

All of the tested CD47 antibodies of this invention showed good binding activities for recombinant human CD47-Fc fusion protein.

Example 2. ELISA Analysis of Antibodies Blocking the Interaction of CD47 to SIRPα

Recombinant human CD47/mouse Fc fusion protein or biotinylated CD47 protein (Acrobiosystems) was coated at 1 ug/mL in PBS onto microtiter plates for 2 hours at RT. After coating of antigen the wells were blocked with PBS/0.05% Tween (PBST) with 1% BSA for 1 hour at RT. After washing of the wells with PBST, the antibodies diluted in PBS were added to the wells (5 ug/mL) and incubated for 1 hour at RT. For detection of the binding antibodies, the HRP conjugated secondary antibodies against human Fc (Jackson Immuno Research) were added, followed by the addition of fluorogenic substrates (Roche). Between all incubation steps, the wells of the plate were washed with PBST three times. Fluorescence was measured in a TECAN Spectrafluor plate reader.

All of the tested CD47 antibodies of this invention showed good binding activities for recombinant human CD47-Fc fusion protein and biotinylated CD47 protein.

Example 3. ELISA Analysis of Antibodies Blocking the Interaction of CD47 to SIRPα

Recombinant CD47-Fc fusion protein (Acrobiosystems) was coated at 1 ug/mL in PBS onto microtiter plates for 16 hours at 4° C. After blocking for 1 hour with 1% BSA in PBST at RT, 1 ug/ml of SIRPα-His protein was added either in the absence or presence of CD47 antibodies (10 ug/mL) at RT for 1 hour. Plates were subsequently washed three times and incubated with an HRP-conjugated anti-His secondary antibody for 1 hour at RT. After washing, the TMB solution was added to each well for 30 minutes and the reaction was stopped with 2.0 M H2504, and OD was measured at 490 nm.

All of the tested CD47 antibodies of this invention effectively blocked the CD47 protein-SIRPα binding.

Example 4. Dose-Dependent Response of CD47 Antibodies Binding to Monomeric CD47-ECD After direct binding and competition screening, a CD47 antibody of this invention 1F8 was selected for this test, in comparison with two existing reference antibodies. Biotinylated CD47 protein (Acrobiosystems) was coated at 1 ug/mL in PBS onto microtiter plates for 2 hours at RT. After coating of antigen, the wells were blocked with PBS/0.05 Tween (PBST) with 1 BSA for 1 hour at RT. After washing of the wells with PBST, different concentrations of CD47 antibodies were added to the well and incubated for 1 hour at RT. For detection of the binding antibodies, the HRP conjugated secondary antibodies against human Fc (Jackson Immuno Research) were added followed by the addition of fluorogenic substrates (Roche). Between all incubation steps, the wells of the plate were washed with PBST three times. Fluorescence was measured in a TECAN Spectrafluor plate reader.

Reference antibodies 5F9 and 2A1 was produced according to the sequence of Hu5F9 and CC-90002 as disclosed by researchers at Stanford University, Inhibrx LLC, and Celgene Corp. (see, e.g., U.S. Pat. No. 9,017,675 B2, U.S. Pat. Nos. 9,382,320, 9,221,908, US Pat. Application Pub. No. 2014/0140989 and WO 2016/109415) and used for the same study.

Figure 1:
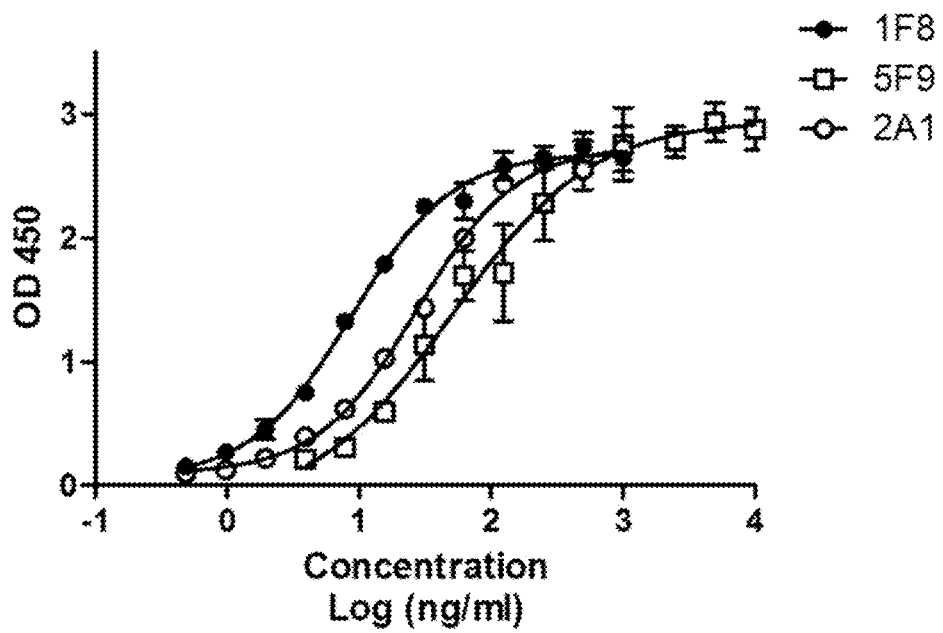
FIG. 1 shows dose-dependent response of CD47 antibodies binding to monomeric CD47-ECD.

As shown in FIG. 1, all three antibodies (1F8, 5F9, and 2A1) showed similar binding activities to monomeric CD47-ECD.

Example 5. Dose-Dependent Response of CD47 Antibodies Binding to Dimeric CD47-ECD The three CD47 antibodies used in Example 4 (i.e., 1F8, 5F9, and 2A1) were also used in this study.

CD47/mouse Fc fusion protein (Acrobiosystems) was coated at 1 ug/ml in PBS onto microtiter plates for 2 hours at RT. After coating of antigen the wells were blocked with PBS/0.05% Tween (PBST) with 1 BSA for 1 hour at RT.

After washing of the wells with PBST, different concentrations of anti-CD47 antibodies were added to the well and incubated for 1 at RT. For detection of the binding antibodies, the HRP conjugated secondary antibodies against human Fc (Jackson Immuno Research) were added followed by the addition of fluorogenic substrates (Roche). Between all incubation steps, the wells of the plate were washed with PBST three times. Fluorescence was measured in a TECAN Spectrafluor plate reader.

Figure 2A:
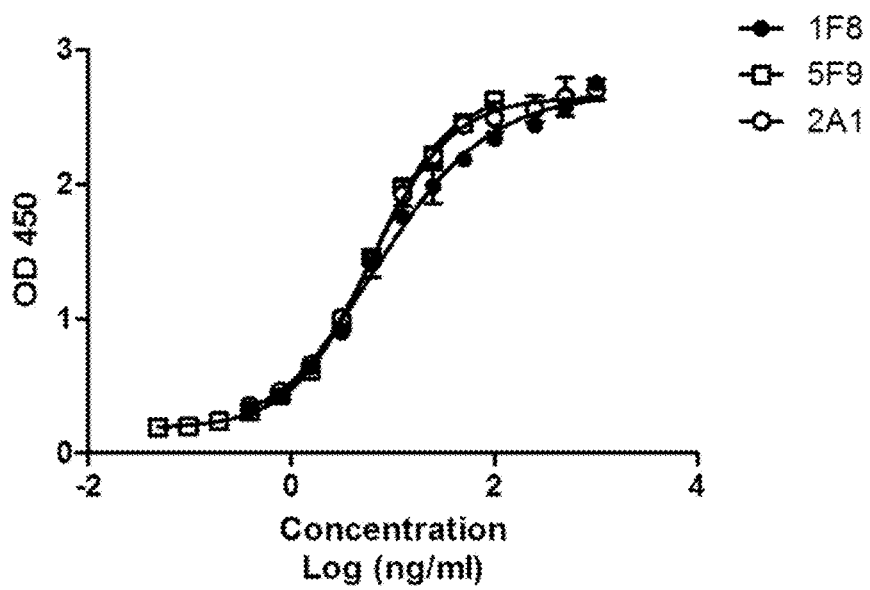
FIG. 2a and FIG. 2b show dose-dependent response of CD47 antibodies binding to dimeric CD47-ECD.

Likewise, as shown in FIG. 2a, among the three tested antibodies 1F8, 5F9, and 2A1, all of them showed similar binding activities to dimeric CD47-ECD.

Figure 2B:
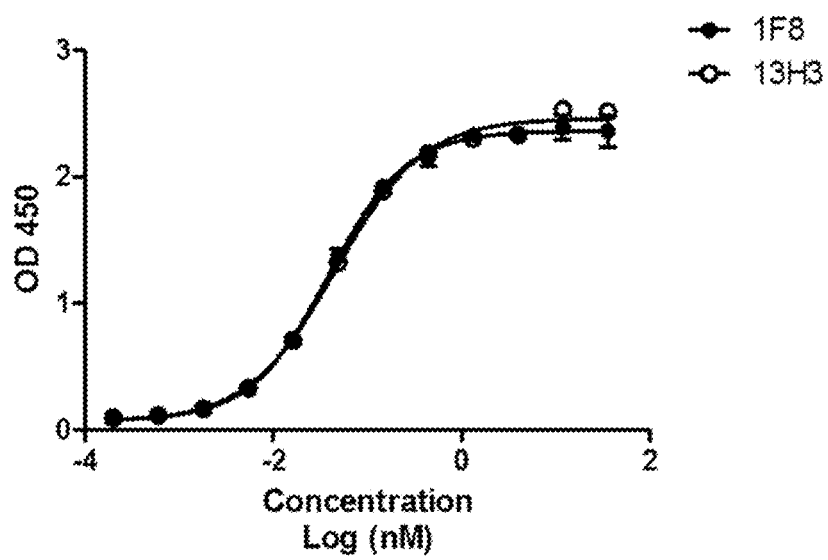

Another binding study was conducted to compare the binding affinity of two antibodies of this invention, i.e., 1F8 and 13H3, to recombinant CD49-ECD. As shown in FIG. 2b, these two antibodies also exhibited similar binding activities in a dose-dependent manner, with $EC_{50}$ being 0.038 nM for 1F8 and 0.045 nM for 13H3.

Example 6. Dose-Dependent Response of CD47 Antibodies Blocking the Binding of CD47 to SIRPα

Three CD47 antibodies (i.e., 1F8, 5F9, and 2A1) were also used in this study.

Recombinant CD47-Fc fusion protein (Acrobiosystems) was coated at 1 ug/ml in PBS onto microtiter plates for 16 hours at 4° C. After blocking for 1 h with 1% BSA in PBST at RT, 1 ug/mL of SIRPα-His protein was added either in the absence or presence of different concentrations of anti-CD47 antibodies at RT for 1 h. Plates were subsequently washed three times and incubated with an HRP-conjugated anti-His secondary antibody for 1 h at RT. After washing, the TMB solution was added to each well for 30 min and the reaction was stopped with 2M H2504, and OD was measured at 490 nm.

Again, as shown in FIG. 3a, all three antibodies showed similar activities in blocking the binding of CD47 to SIRPα.

Another study was conducted to compare the ability of two CD47 antibodies of this invention 1F8 and 13H3 to block the binding of CD47 to SIRPα. As shown in FIG. 3b and FIG. 3c, these two antibodies also exhibited similar blocking activities in a dose-dependent manner, with $IC_{50}$ being 0.78 nM for 1F8 and 0.20 nM for 13H3.

Example 7. Dose-Dependent Response of CD47 Antibodies Binding to CD47+ Raji Cells Three CD47 antibodies (i.e., 1F8, 5F9, and 2A1) were also used in this study.

Raji cells which endogenously express human CD47 on the surface were stained with different concentrations of 1F8, 5F9 and 2A1 antibodies at 4° C. for 30 minutes. Then, the cells were washed with PBS three times, followed by incubation with APC-labeled anti-human Fc specific antibody (Invitrogen) at 4° C. for 30 minutes. Binding was measured using a FACSCanto (Becton-Dickinson).

As shown in FIG. 4a, all three antibodies showed similar activities in binding to CD47 Raji cells, following the same dose-dependent pattern.

Another study was conducted to compare the ability of two CD47 antibodies of this invention 1F8 and 13H3 to bind to CD47-bearing Raji cells. As shown in FIG. 4b, 13H3 exhibited stronger affinity than 1F8 in binding CD47-bearing Raji cells, with $EC_{50}$ being 2.95 nM for 1F8 and 1.06 nM for 13H3.

FIG. 4c and FIG. 4d show the binding kinetics of 1F8 and 13H3, respectively, as measured by Biocore analysis; and FIG. 4e shows the data.

Example 8. Study of Phagocytosis of Tumor Cells by Human Macrophage (MΦ)

Three CD47 antibodies (i.e., 1F8, 5F9, and 2A1) were also used in this study.

PBMCs were isolated from human blood, and the monocytes were differentiated into macrophages for 6 days. The monocyte derived macrophages (MDMs) were scraped and re-plated in 24-well dishes and allowed to adhere for 24 hours. The human tumor cell line Raji which endogenously expressed CD47 were chosen as target cells and labeled with 1 uM CFSE for 10 minutes, then added to MDMs at a ratio of 5:1 tumor cells per phagocyte and CD47 antibodies was added at various doses. After incubation for 3 hours, non-phagocytosed target cells were washed away with PBS and the remaining phagocytes were scraped off, stained with macrophage marker CD14 antibody, and analyzed by flow cytometry. Phagocytosis was measured by gating on $CD14^+$ cells and then assessing the percent of CFSE cells.

As shown in FIG. 5a, all these three tested antibodies (i.e., 1F8, 5F9, and 2A1) showed similar activities in promoting phagocytosis of tumor cells by human MΦ. FIGS. 6a, 6b, and 6c show the macrophage-mediated phagocytosis of three different human blood cancer cell lines, triggered by the three CD47 antibodies.

Another study was conducted to compare the ability of two CD47 antibodies of this invention 1F8 and 13H3 to promote phagocytosis of tumor cells by human MΦ. As shown in FIG. 5b, 13H3 and 1F8 exhibited similar abilities with 13H3 slightly stronger phagocytosis at some concentrations.

Example 9. RBC-Sparing Property in RBC Agglutination Assay

Human RBCs were diluted to 10 in PBS and incubated at 37° C. for 2 hours with a titration of CD47 antibodies in a round bottom 96-well plate. Evidence of hemagglutination is demonstrated by the presence of non-settled RBCs, appearing as a haze compared to a punctuate red dot of non-hemagglutinated RBCs (see FIGS. 7a and 8a). The graphs in FIGS. 7b and 8b show the quantitation of the hemagglutination assay, denoted "agglutination index" determined by quantitating the area of the RBC pellet in the presence of the antibody, normalized to that of IgG control.

Figure 8A:
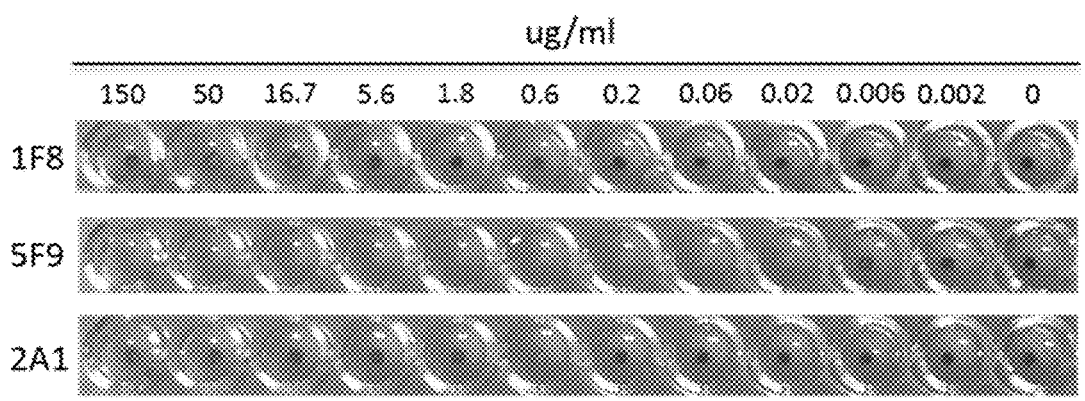
Figure 8B:
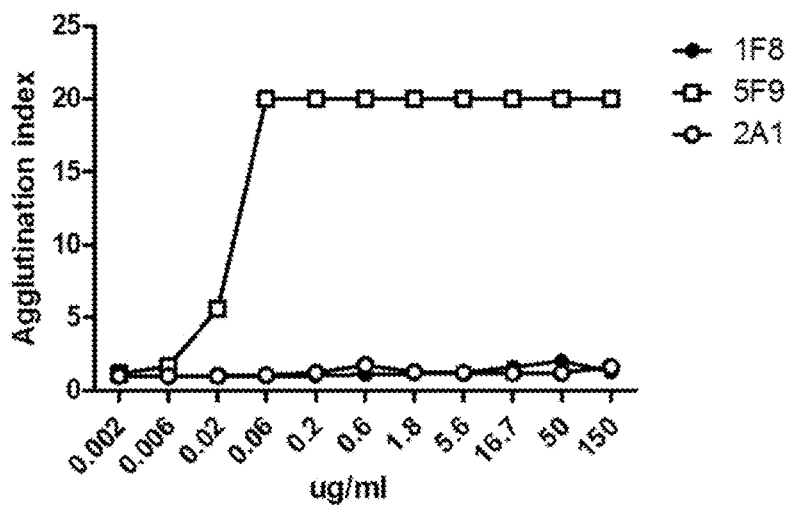

As shown in FIGS. 7a, 7b, 8a, and 8b, while CD47 antibody 5F9 already showed significant RBC agglutination at a concentration of or higher than 0.1 ug/uL, CD47 antibodies 1F8 and 2A1 resulted in essentially no RBC agglutination at the tested concentrations up to 30 ug/uL (FIGS. 7a and 7b) or even up to 150 ug/mL (FIGS. 8a and 8b).

Figure 8C:
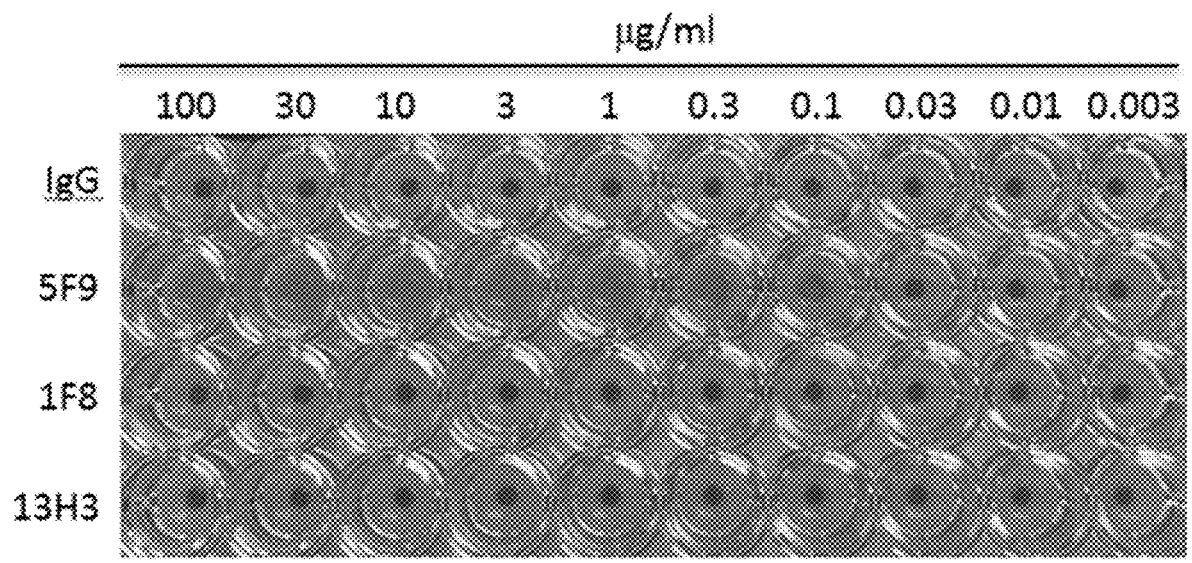
Figure 8D:
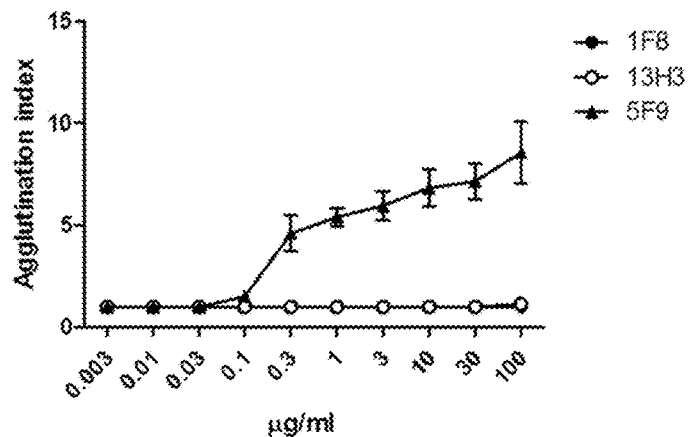

Likewise, FIGS. 8c and 8d show that CD47 antibodies of this invention (i.e., 1F8 and 13H3) resulted in essentially no RBC agglutination at the tested concentrations up to 150 ug/mL, whereas CD47 antibody 5F9 already showed significant RBC agglutination at a concentration of or higher than 0.1 ug/uL.

Example 10. RBC Binding Assay

Binding of CD47 antibodies against human RBCs was examined by flow cytometry. Human RBCs were incubated with CD47 antibodies (10 ug/mL) at 4° C. for 1 hour, followed by the addition of APC-conjugated secondary antibody at 4° C. for 30 minutes.

Figure 9A:
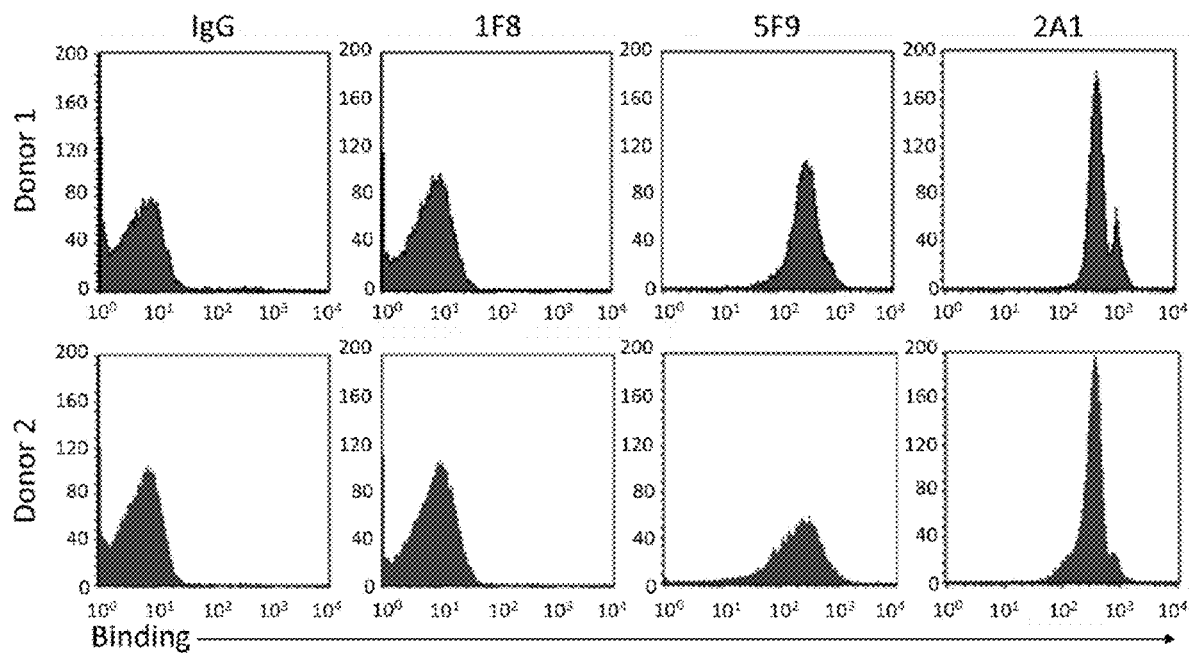
Figure 9B:
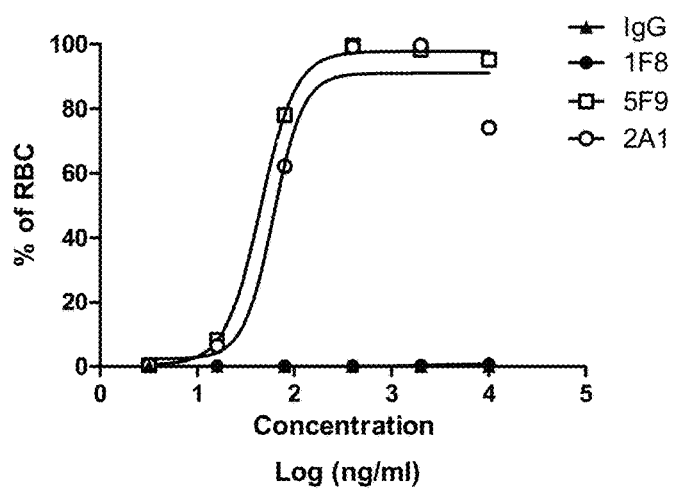

As shown in FIGS. 9a and 9b, surprisingly, CD47 antibody of this invention 1F8 did not bind to RBC while reference CD47 antibodies 5F9 and 2A1 did at the tested concentrations.

Figure 9C:
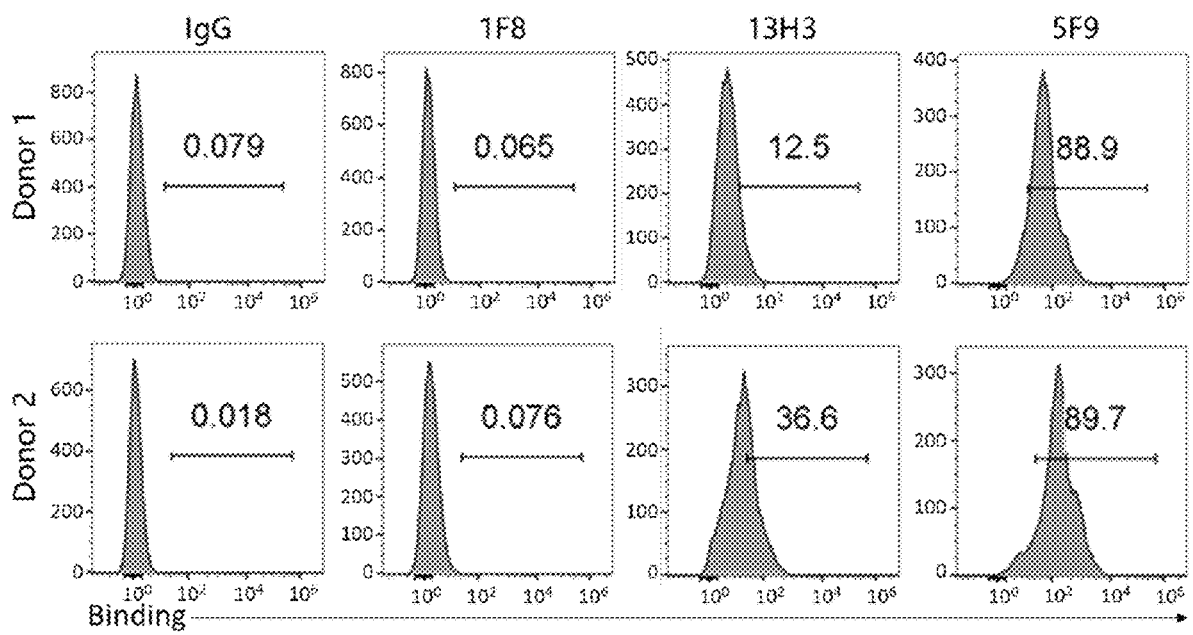
Figure 9D:
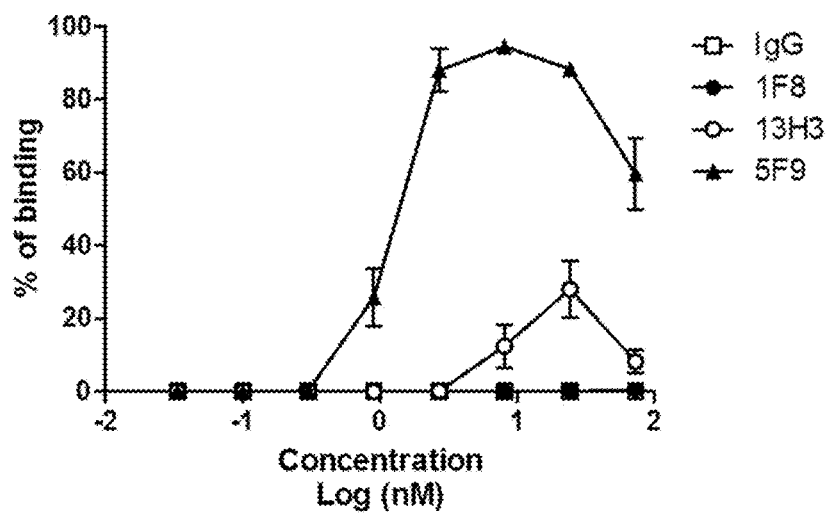

Likewise, FIGS. 9c and 9d show that while 1F8 resulted in no RBC binding at the tested concentrations, 13H3 only resulted in very low RBC binding at the tested concentrations.

Example 11. RBC Agglutination Assay

Figure 10A:
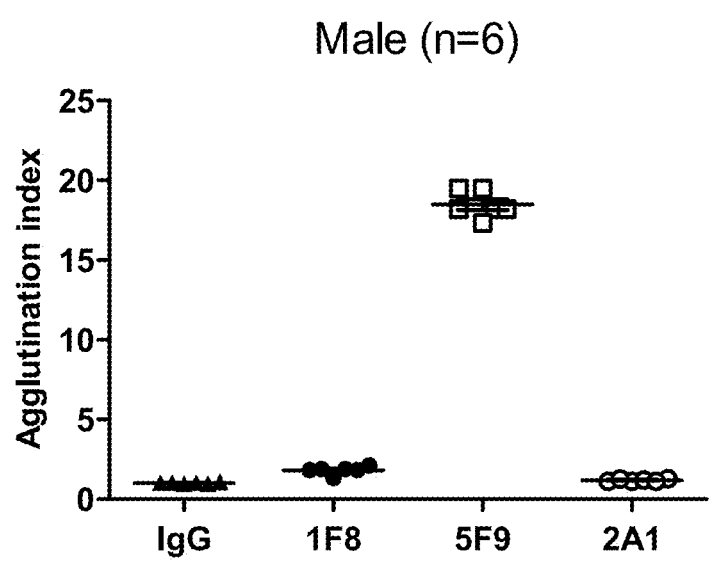
Figure 10B:
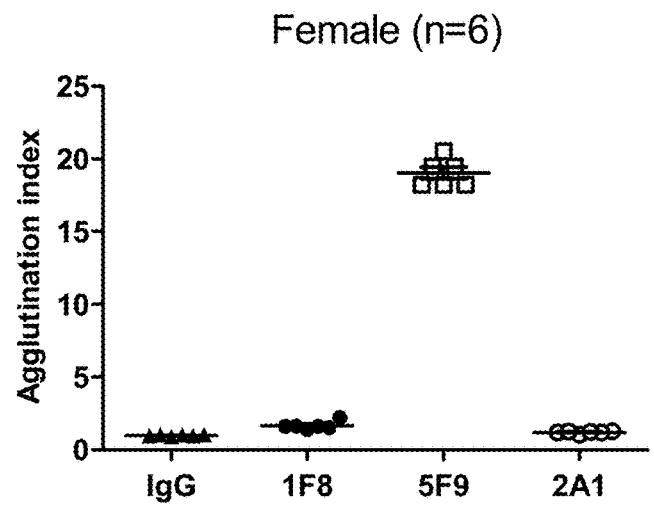

RBCs were collected from six male and six female healthy individuals for the analysis of RBC agglutination by the addition of CD47 antibodies. FIGS. 10a and 10b show the titration results of the hemagglutination assay, which is denoted "agglutination index" as determined by measuring the area of the RBC pellets in the presence of the antibody, normalized to that of IgG control or reference antibody.

Example 12. Platelet Binding Assay

Binding of CD47 antibodies of this invention against human platelets was examined by flow cytometry. Human peripheral whole blood was incubated with test CD47 antibodies of this invention (at 10 ug/mL) or SIRPα-Ig fusion and CD61 was stained as a surface marker for platelets. The binding of CD47 antibodies or SIRPα-Ig fusion was measured by gating on the CD61 positive population (platelet) and further examining the percentages of CD47 or SIRPα-Ig fusion binding.

As shown in FIG. 11, tested CD47 antibodies of this invention did not appreciably bind to human platelets whereas SIRPα proteins did.

Example 13. Cyno RBC Agglutination Assay

Figure 12A:
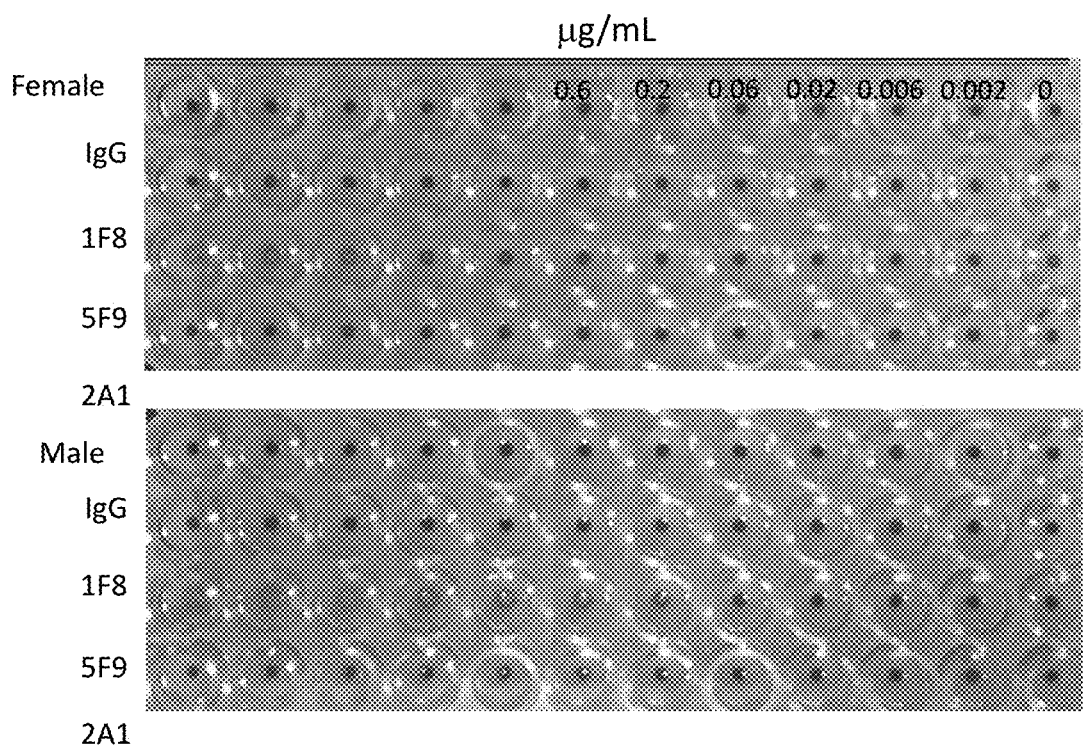
Figure 12B:
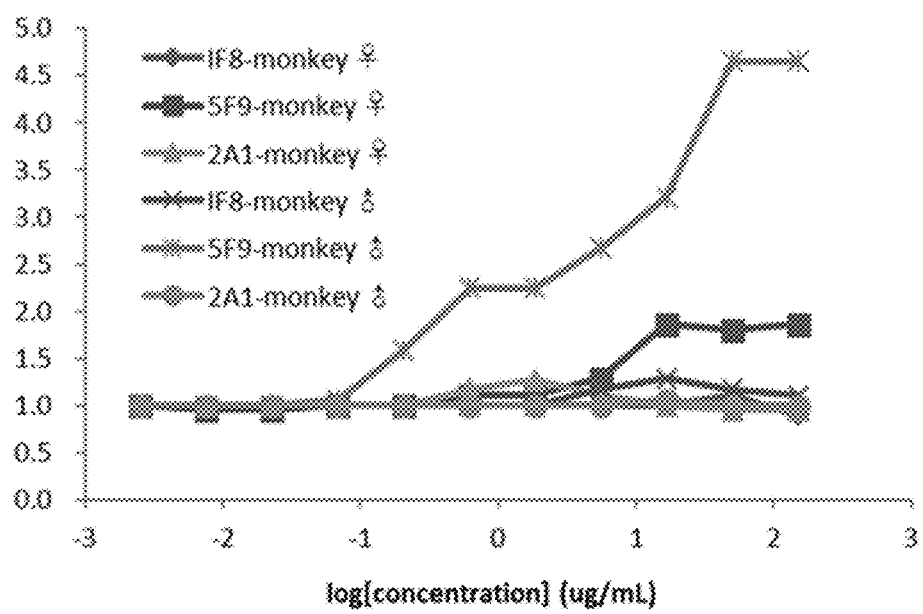

RBCs from male and female cyno monkey were diluted to 10% in PBS and incubated at 37° C. for 2 hours with the indicated concentrations of CD47 antibodies in a round bottom 96-well plate. Evidence of hemagglutination was demonstrated by the presence of non-settled RBCs, appearing as a haze compared to a punctuate red dot of non-hemagglutinated RBCs, as shown in FIG. 12a. FIG. 12b shows the titration results of the hemagglutination assay, which is denoted "agglutination index" as determined by measuring the area of the RBC pellets in the presence of the antibody, normalized to that of IgG control.

The data show that the tested CD47 antibodies of this invention did not appreciably induce cyno RBC agglutination in vitro.

Example 14. Phagocytosis of Primary Human AML Cells by CD47 Antibodies

Primary PBMCs from AML patient (AML-PB003F) were labeled with 1 uM CFSE for 10 minutes, then added to MDMs at a ratio of 5:1 tumor cells per phagocyte and the indicated CD47 antibodies was added at various concentrations. After 3-hr incubation, non-phagocytosed target cells were washed away with PBS and the remaining phagocytes were scraped off, stained with a CD14 antibody, and analyzed by flow cytometry. Phagocytosis was measured by gating on CD14+ cells and then assessing the percentage of CFSE+ cells. Phagocytosis was measured as previously mentioned.

As shown in FIGS. 13a-13h, the tested CD47 antibodies of this invention all showed significant AML binding capabilities (greater than 75%) and phagocytosis capabilities (at least 36%), all of which are much higher than the reference CD47 antibody used in the same essay.

Example 15. In Vivo Efficacy of 1F8 Using Luciferase-Raji Xenograft Model (CDX)

NSG mice were engrafted with Raji Luc-EGFP at a concentration of 1 million cells/mouse via tail vein injection. They were imaged in vivo to determine the level of engraftment five days post engraftment. Treatment of CD47 antibodies (i.e., 1F8, 5F9, and 2A1) started from the same day at a dose of 10 mg/kg. All mice were injected every other day via intraperitoneal injection. Mice were imaged in vivo via IVIS Lumina III imaging system at the following time points: Day 0 of antibody treatment, Day 2 of treatment, Day 6 of treatment, and Day 9 of treatment. The tumor growth in the mice was measured by the analysis of bioluminescent radiance through in vivo live imaging system.

As can be seen in FIG. 14a, the analysis of bioluminescent radiance shows that the tumors in the mice barely grew within the first three days after the treatments with the tested CD47 antibody of this invention (i.e., 1F8) and the tumors reduced from day 6 after the treatments. By comparison, the tumors in the mice treated with reference CD47 antibody continued to grow during the same treatment period.

Similarly, FIG. 14b shows that the CD47 antibody 13H3 was also effective in vivo in Raji xenograph model at different test concentrations.

In the end of Raji-xenograft study, all the mice were euthanized by the use of $CO_2$ for rodent euthanasia. The splenocytes from four groups of mice were isolated and analyzed for the percentage of M1 macrophages (% of CD80 positive in F4/80 positive macrophages) and M2 macrohpages (% of CD206 positive in F4/80 positive macrophages) by flow cytometry analysis.

Figure 15A:
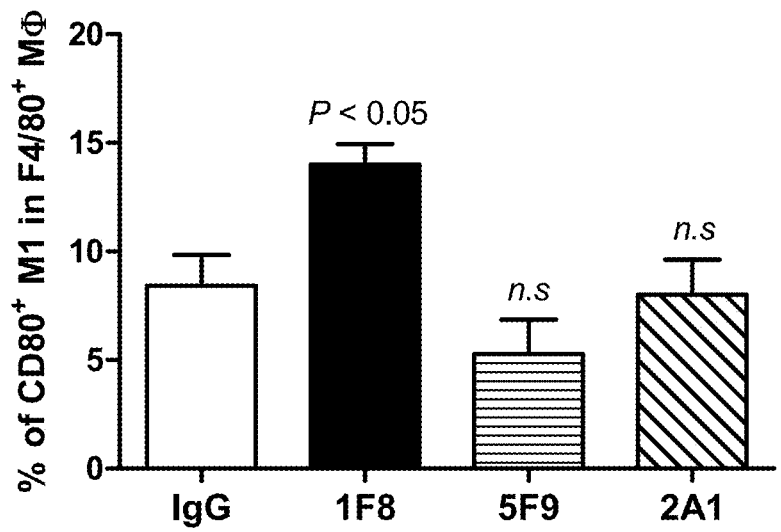
Figure 15B:
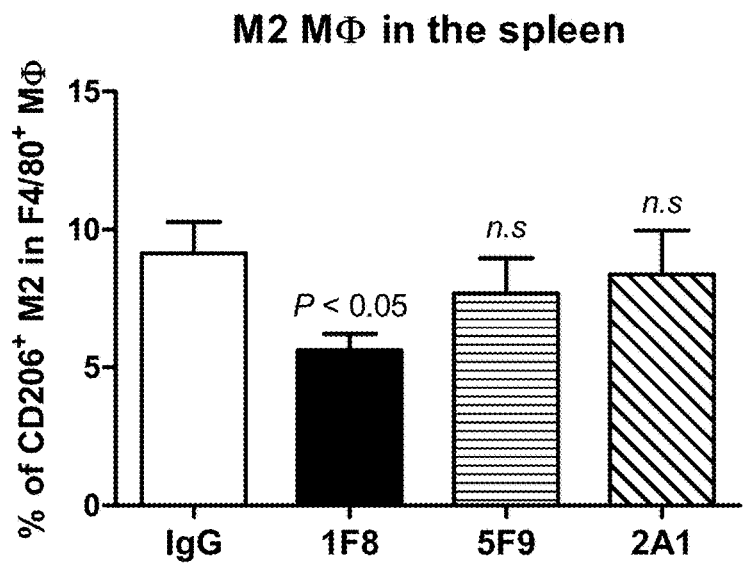

As shown in FIGS. 15a-15b, all of the tested CD47 antibodies (including 1F8) were able to induce polarization of macrophage in tumor-bearing mice.

Figure 16A:
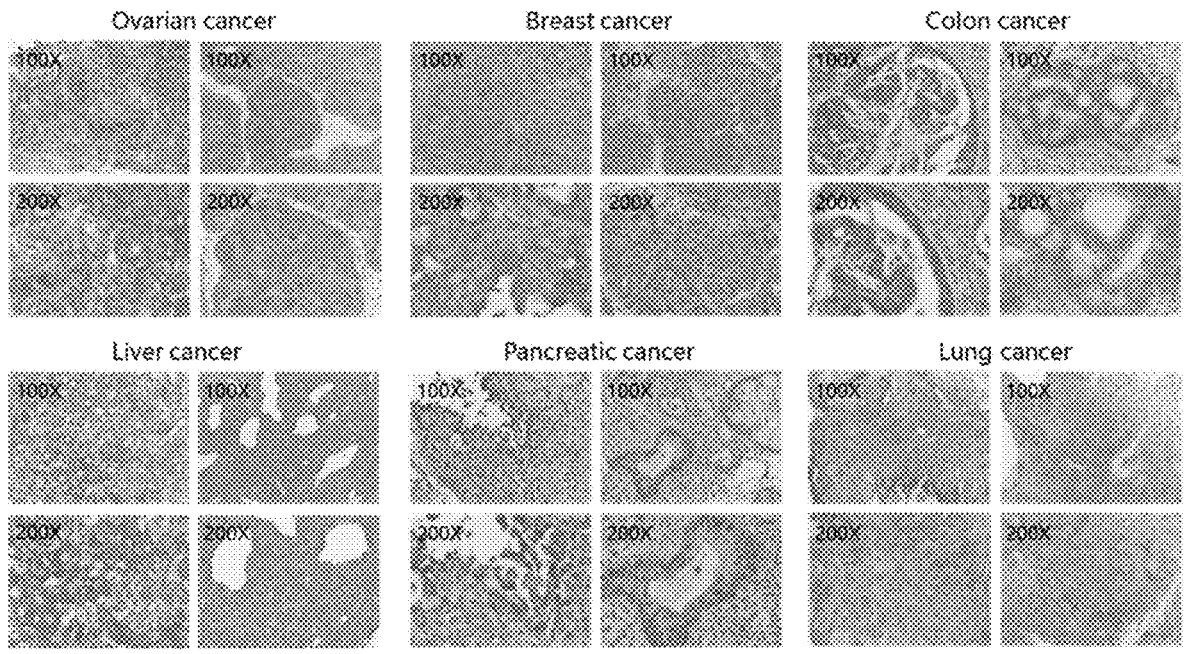
Figures 16B, 16C:
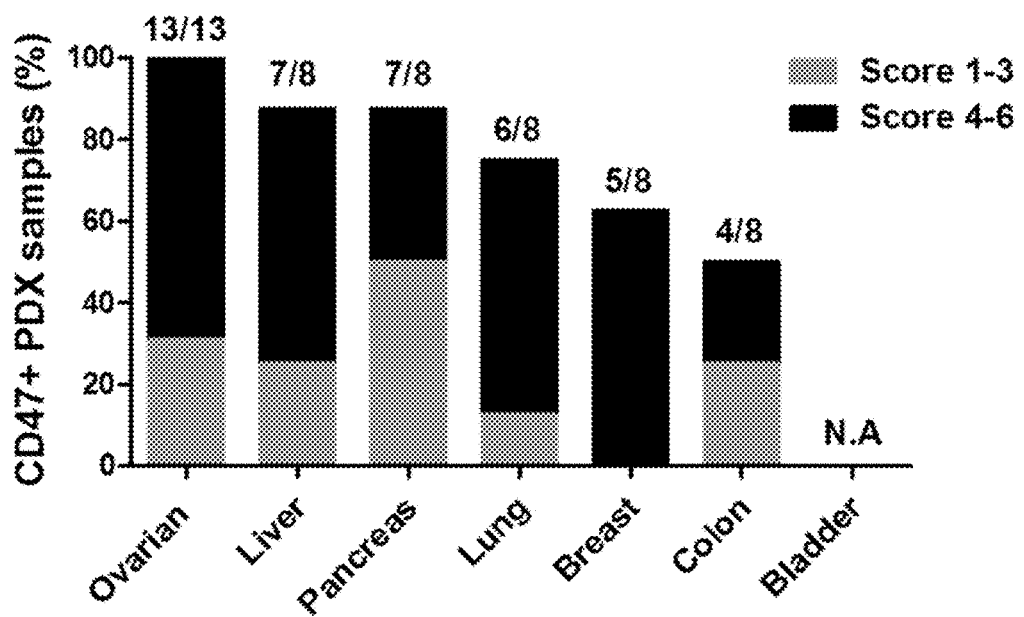
Figure 17A:
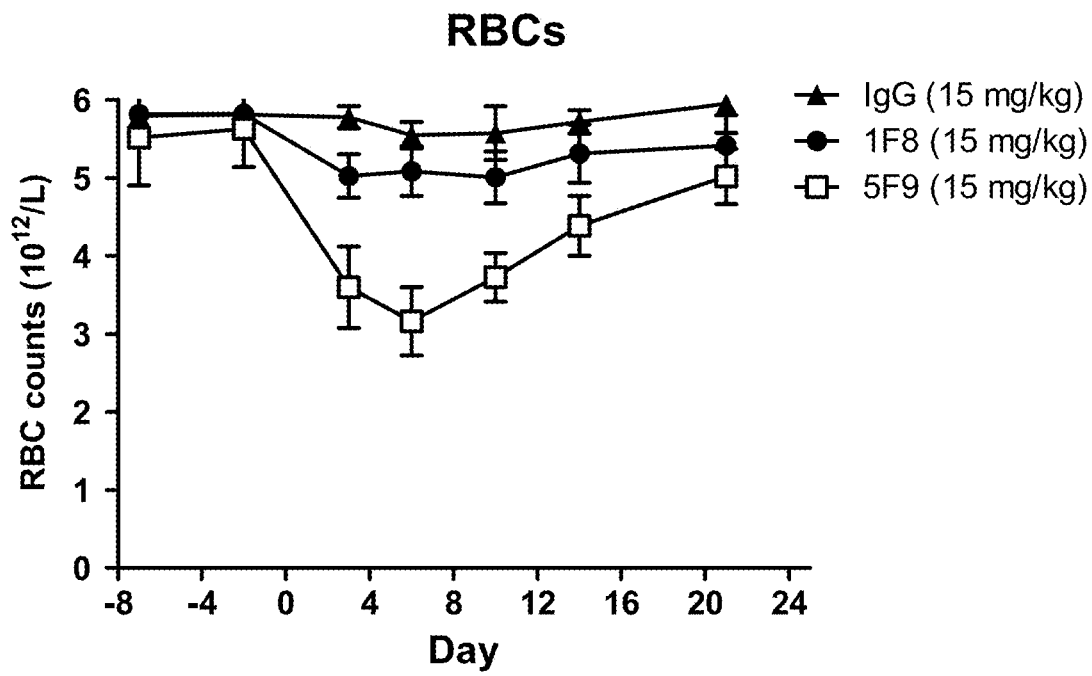
Figure 17B:
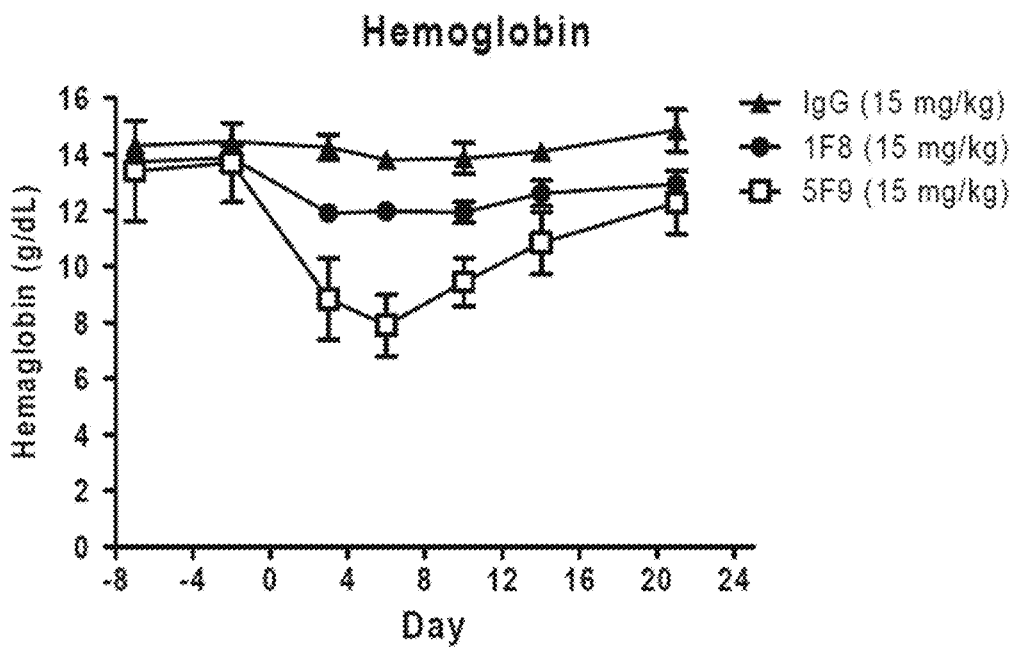
Figure 17C:
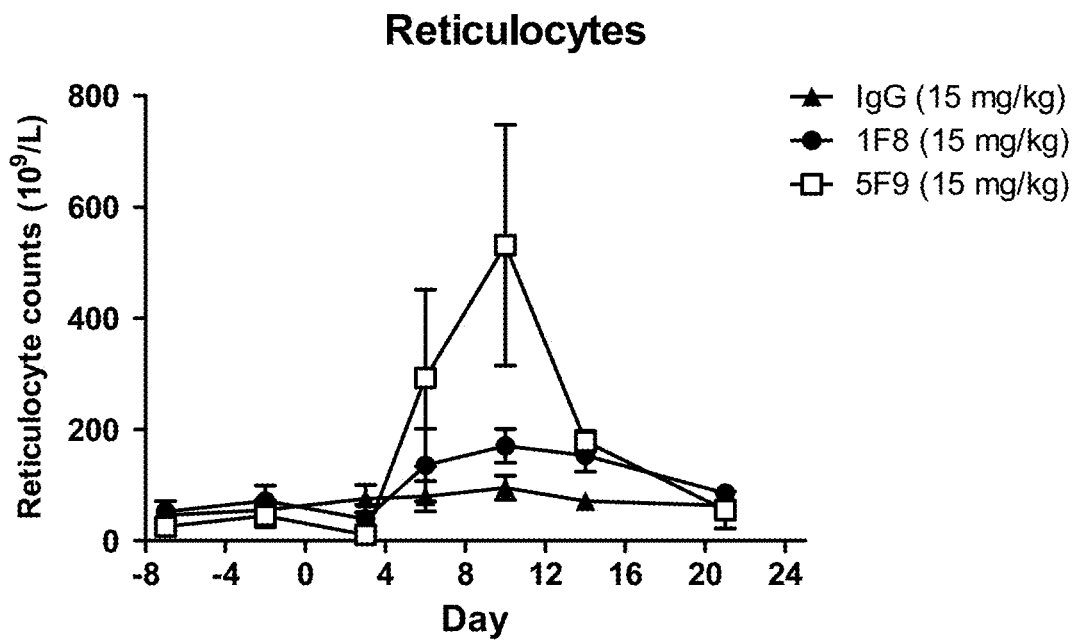
Figure 17D:
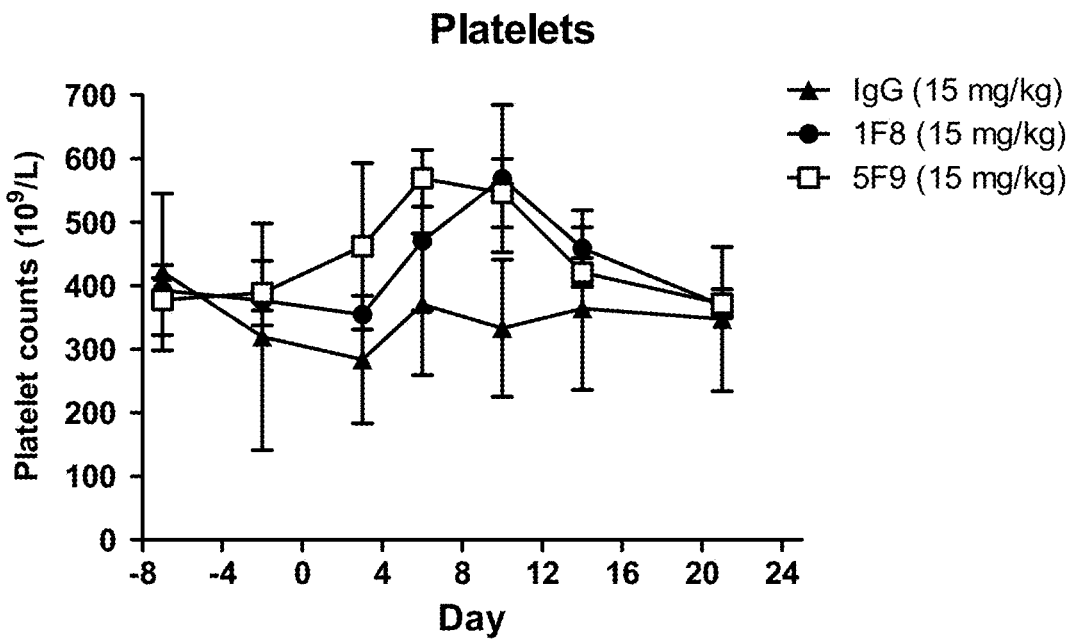
Figure 17E:
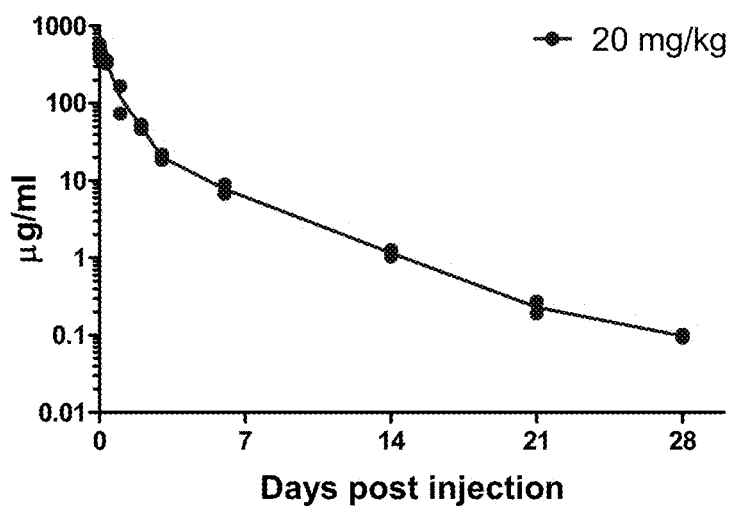

Example 16. CD47 Expression Profile Using PDX Samples of Various Human Cancer Types 54 PDX samples (across 7 human cancer types) were analyzed for the expression of CD47 by immuno-histochemistry staining. The levels of CD47 staining in various PDX samples were scored by geometry and staining intensity. FIGS. 16a, 16b and 16c show the different expression levels of CD47 after the treatments with CD47 antibodies.

Example 17. Safety Pharma Study (In Vivo Cyno PK Studies)

Naive cyno monkeys were intravenously infused with vehicle (n=2), 1F8 (n=3, 15 mg/kg) and 5F9 (n=3, 15 mg/kg). Hematology (CBC) was analyzed within 24 hours after blood collection, twice before the injections and at 3, 6, 10, 14 and 21 days following the antibody administration. CBC parameters were examined including Erythrocyte count (RBC), Hemoglobin (HGB), Absolute Reticulocytes and Platelet Counts. The results are depicted in FIGS.

17a-17d and showed that 1F8 treatments did not affect the hematology parameters in cyno monkey.

Similarly, Naive cyno monkeys (n=2) were intravenously injected with CD47 antibody 13H3 at a dose of 20 mg/kg. Their blood was collected by venipuncture into tubes with no anticoagulant at different time points. Serum level of the CD47 antibody 13H3 was measured by ELISA using CD47 protein as the coating reagent, followed by detection with an HRP-conjugated anti-human Kappa secondary antibody. Pharmacokinetic parameters in cyno monkeys were analyzed by Winolin and shown in FIG. 17e and the following table.

| $T_{1/2}$ (h) | $C_{max}$ (μg/ml) | $AUC_{0-t}$ (day*ug/ml) | $AUC_{inf}$ (day*ug/ml) | CL (ml/hr/kg) |
|---|---|---|---|---|
| 145.2 ± 10.8 | 536.4 ± 63.9 | 10692.1 ± 1300.9 | 10712.5 ± 1298.4 | 1.880 ± 0.228 |

Safety Pharm Study (Hematology) of Antibody 13H3 in Cynomolgus Monkey

Naive cyno monkeys were intravenously infused with single dose or repeat dose (weekly dosing) of the anitbody 13H3 (20 mg/kg). Hematology (CBC) parameters were examined including Erythrocyte count (RBC), Hemoglobin (HGB), Platelet Counts and Lymphocyte Counts at the indicated time points following the antibody administration.

FIGS. 19a, 19b, 19c, 19d, 19e, 19f, 19g, and 19h show the effects of the CD47 antibody 13H3 on RBC congregation, hemoglobin, platelets, and lymphocytes.

Example 18. Structure of Antibody 1F8

Figure 18A:
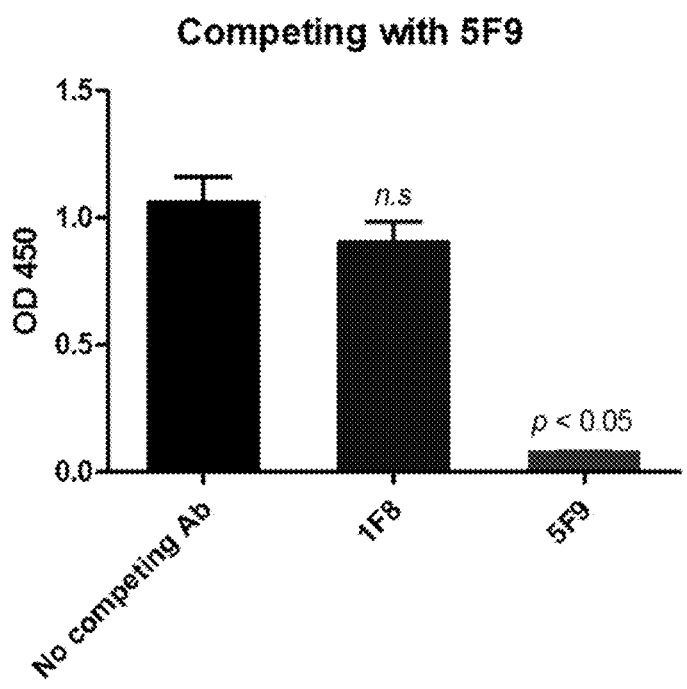
Figure 18B:
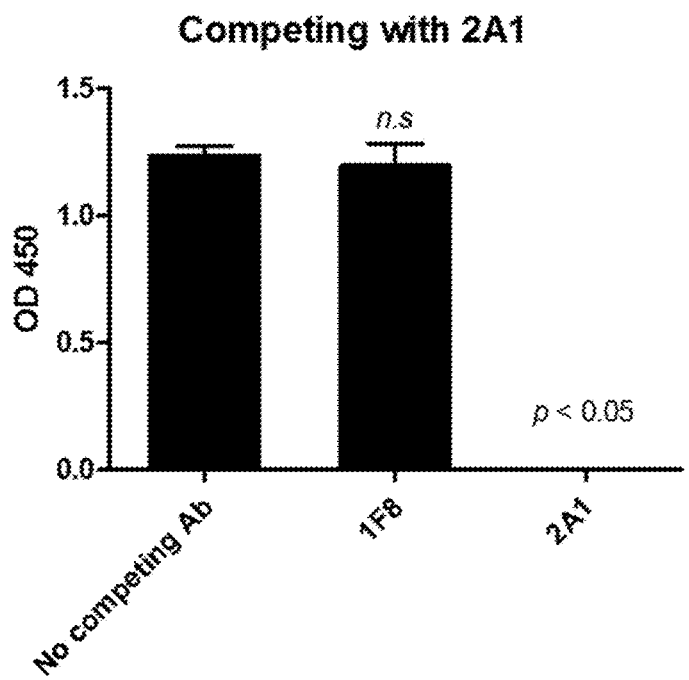

The epitope binning of CD47 antibodies was assessed by competition ELISA. CD47 ECD protein and first anti-CD47 antibody were pre-incubated and added to a biotinylated second anti-CD47 antibody detected by a Strptavidin-HRP antibody. If the first anti-CD47 antibody competed against the binding of CD47 ECD to the second antibody, both antibodies were placed in same or overlapping epitope bins. If not, they were placed in non-overlapping epitope bins. The results depicted in FIGS. 18a and 18b show that CD47 antibody of this invention 1F8 has a different epitope than those of reference antibodies 5F9 and 2A1.

Figure 18C:
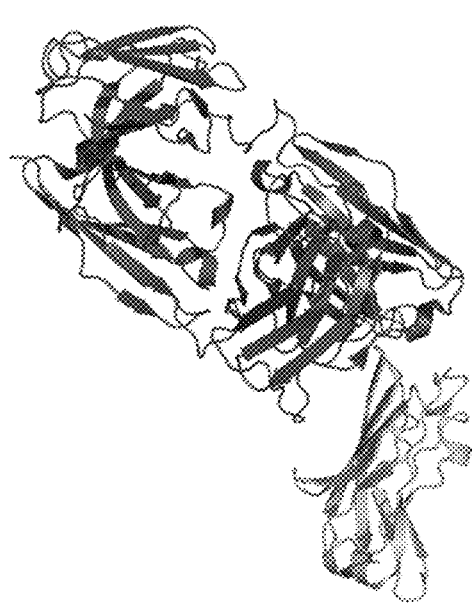

FIG. 18c shows the crystal structure of reference Ab 5F9 (upper part) in complex with human CD47-ECD (green) as reported in the literature (See, e.g., J. Clin. Investigation, 126, 7: 2610-2620).

Figure 18D:
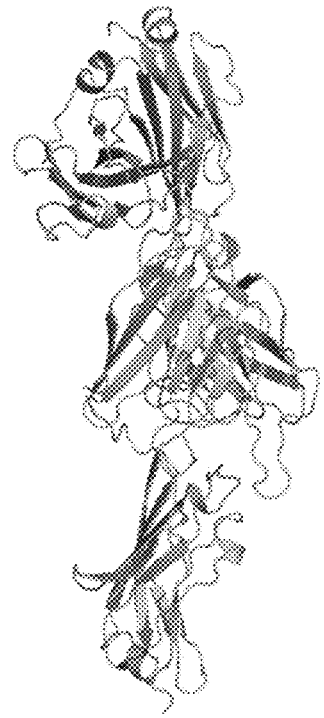

FIG. 18d shows the crystal structure of 1F8-Fab (upper part) in complex with human CD47-ECD (green). The complex structure of CD47-1F8 Fab adopts straighter head to head orientation, unlike the complex structures of CD47-SIRPα and CD47-5F9 diabody presenting tilted head to head orientation. The 1F8 epitope on CD47 is discontinuous and extensive which includes residues L3, V25, T26, N27, M28, E29, A30, Q31, T34, E35, Y37, A53, L54, L74, K75, G76, T99, E100, L101, T102 and R103, of which L3, N27, E29, Q31, T34, E35, Y37, A53, T99, E100, L101, T102 and R103 are involved in the interactions with SIRPα, explaining the antagonistic properties of 1F8. The complex structure also reveals VH domain of 1F8 forms 8 hydrogen bonds and 4 salt bridges to CD47 and VL domain of 1F8 forms 8 hydrogen bonds to CD47 as well.

Unlike published CD47-lgV/antibody or SIRPα complex structures, the 1F8 antibody binds mostly different epitopes of the target although all are binding in the similar head-to-head orientation. The 1F8 epitope on CD47 is conformationally discontinuous and includes a TNMEAQ loop (residues 26-31), T34, E35, L74, and an LTR hinge (residues 101-103) of CD47. Many hydrogen bond interactions are formed between side chains of antibody residues and CD47 main chain oxygen atoms. A salt bridge is also formed between R103 of 1F8 and E35 of CD47. Several Van der Waals contacts are also observed which are critical to keep appropriate orientation. The VH domain of antibody 1F8 is primarily involved in binding to the T34, E35 and the LTR hinge (residues 101-103) of CD47, while the VK domain interact with the TNMEAQ loop (residues 26-31) and L74. These epitopes on CD47 are different from that in 5F9 antibody and SIRPα. Structural analysis suggest that two long loops (residues 26-38 and 52-59) of the 1F8 antibody help it bind to CD47 in a nearly vertical orientation which may lead to the antibody to be separated in such a way that CD47 on adjacent cells could not be bridged by the antibody, thereby preventing most of blood cell hemaglutination.

Figure 18E:
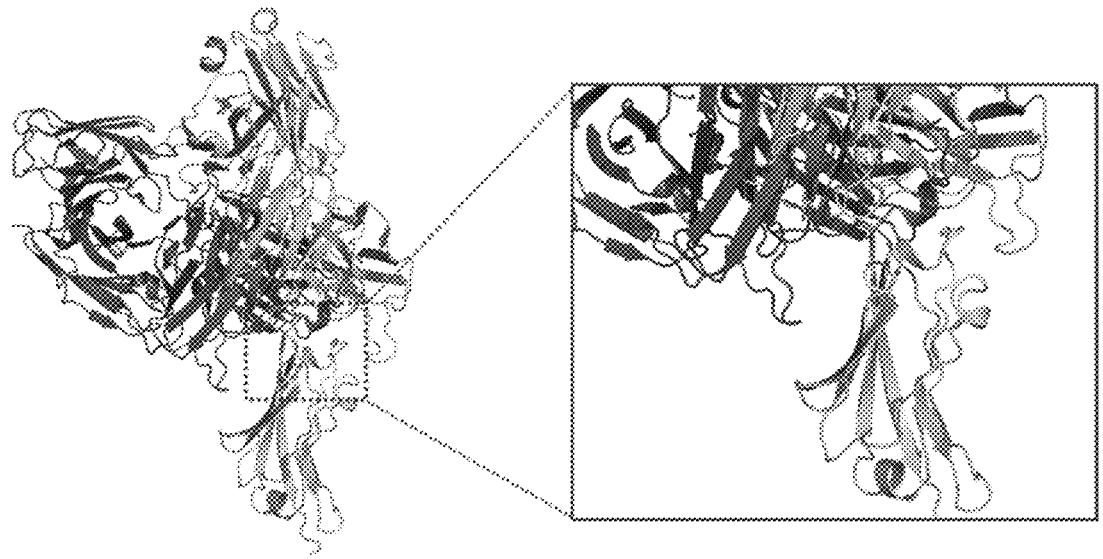
Figure 19A:
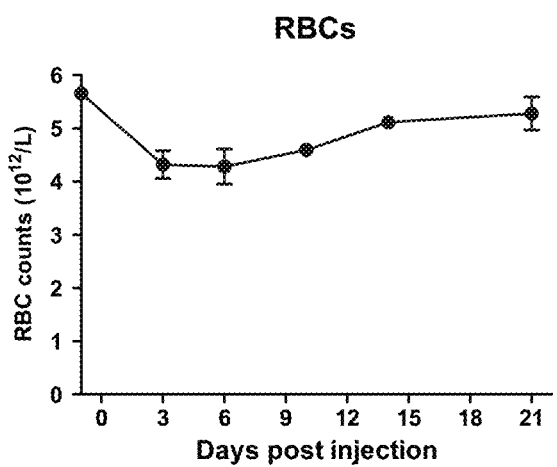
Figure 19B:
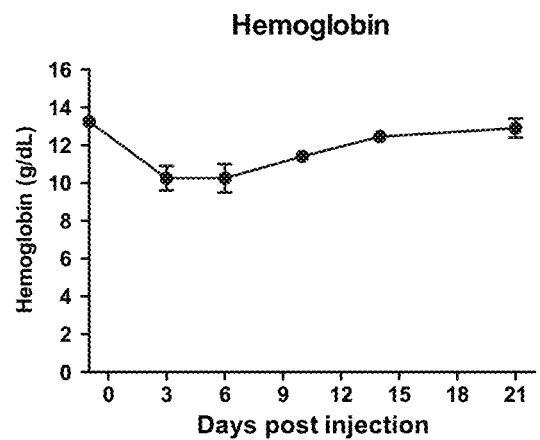
Figure 19C:
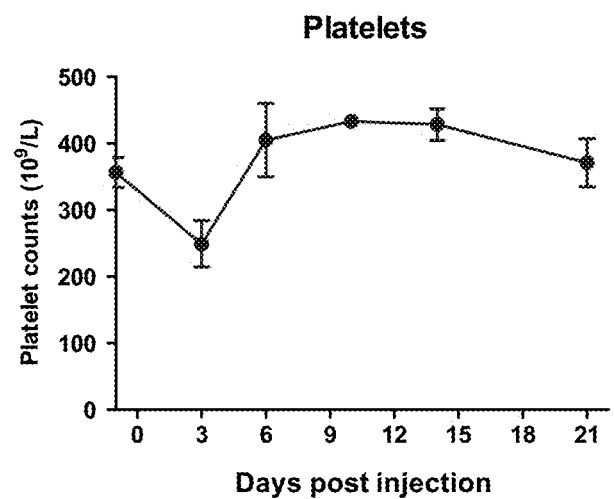
Figure 19D:
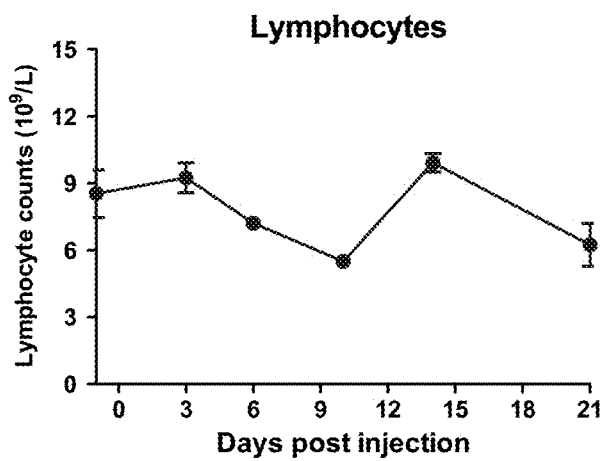
Figure 19E:
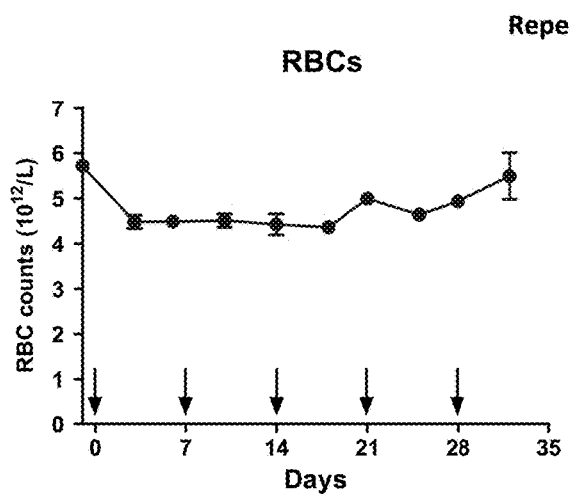
Figure 19F:
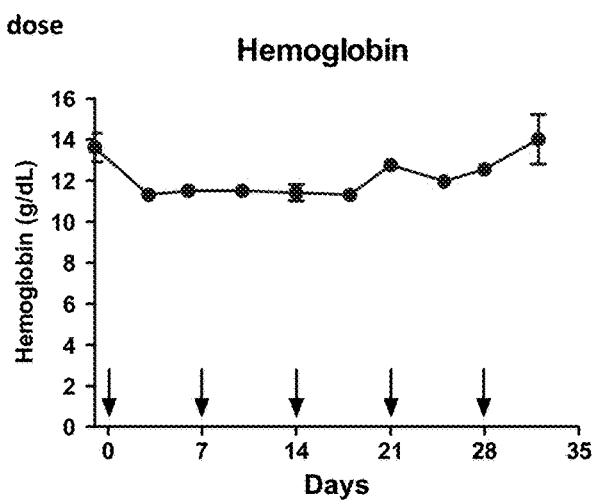
Figure 19G:
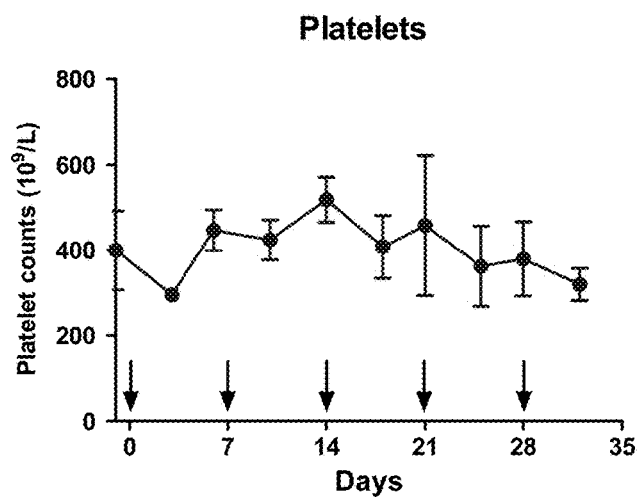
Figure 19H:
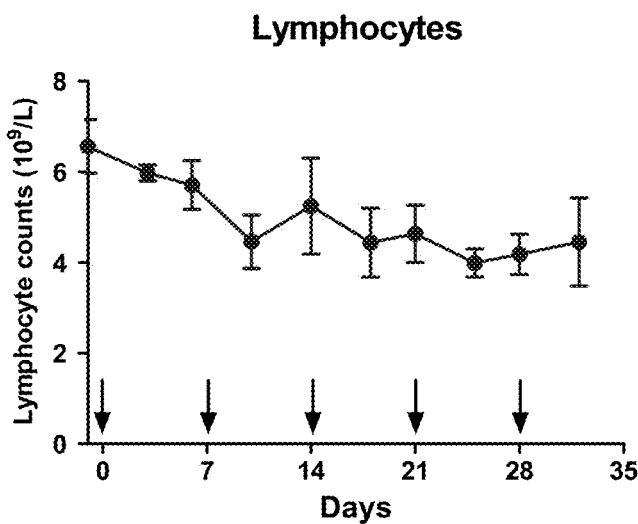

FIG. 18e shows the comparison of interaction of 5F9 and 1F8 with CD47.

Superposition of reference antibody 5F9/CD47 complex structure on complex structure of 1F8/CD47 reveals that binding orientation of CD47 is very different between these two complexes. Although both antibodies have head-to-head binding orientation, CD47 is rotated horizontally by about 180 degree. The structure of 1F8/CD47 complex has CD47 N-terminal pyroglutamate near light chain loop residues 61-64, while 5F9 has CD47 N-term among 3 heavy chain loops of W52, N32 and W101. In antibody 1F8, the heavy chain residues Trp33 and Arg103 form van der Waals contact and a salt bridge with Leu101 and Glu35 of CD47, respectively. At the same position, antibody 5F9's residue Tyr101 point towards N-term of CD47 through a van der Waals contact and Arg102 forms a hydrogen bond with Glu104 of CD47. Antibody 1F8's loop residues Asn31, Trp33, and hinge residues Arg53 and Asp56 form interdomain hydrogen bonds net, then Asn31 and Arg53 form hydrogen bonds with main chain of Leu101 and Thr34 in CD47. At the same interface, 5F9 does not appear to make interaction, except residue Tyr 52 forms a van der Waals contact with Leu3 on CD47. The hinge (residue 52-56) is 3 residues shorted than that of 1F8 (residues 52-59). In light chain, both Fab 1F8 and 5F9 have several important hydrogen bond interactions with CD47 from the loop (V29-Y38 in 1F8 and V152-Y158 in 5F9). Residues Y97 and Y98 in 1F8 "push" the loop (residues 26-38) away, and the latter formed 2 hydrogen bonds between 1F8 and CD47, namely between Arg34 of 1F8 and main chain of Leu74 on CD47, and between Arg36 of 1F8 and main chain of Thr26 on CD47. However, 5F9's residues Gly218 and Ser219 (which correspond to Tyr97 and Tyr98 in 1F8) cause the loop (residues 149-158) in 5F9 to form 3 hydrogen bonds with CD47 (at Asn157-Lys39, Tyr159-Glu104 and Lys177-Thr99,). Also like that in heavy chain, the loop (residues 149-158) in 5F9 is about 3 residues shorter than that in 1F8 (residues 26-38). These relative longer loops in 1F8 mainly contribute to the binding orientation of the CD47.

Example 19. CD47 Antibody 34C5

To generate anti-human CD47 antibodies, different strains of 6-8-week mice including BALB/C, C57/BL6 or SJL mice were immunized with recombinant human CD47 extracellular domain protein for several rounds. After immunization, mice with sufficient titres of anti-CD47 IgG were boosted with the same antigen followed by fusion. The hybridoma supernatants were tested for direct binding with human CD47 ECD protein and competition of SIRPα binding to CD47 by ELISA screening. Through a series of screening assays, 34C5 was selected for the humanization and further in vitro characterization according to the assays described above.

FIG. 20 and FIG. 21 show strong binding affinity of 34C5 to recombinant CD47-ECD (with an $EC_{50}$ of 0.27 nM) and to CD47-bearing Raji cells (with an $EC_{50}$ of 0.83 nM), respectively.

FIG. 22 shows that 34C5 was able to effectively block CD47 binding to SIRPα, with a $EC_{50}$ of 0.30 nM.

FIG. 23 shows that the antibody 34C5 promoted phagocystosis of tumor cells by human MED.

FIG. 24 shows the antibody 34C5 did not cause in vitro RBC agglutination.

FIG. 25 shows the antibody 34C5 decrease its binding to RBC with the decreasing concentration of this antibody.

What is claimed is:

1. A full length monoclonal antibody that binds to human CD47, comprising:
   (i) two heavy chains each of said heavy chains comprising a VH CDR1, a VH CDR2, and a VH CDR3 as set forth in a variable heavy (VH) chain region comprising the amino acid sequence of SEQ ID NO: 31, and
   (ii) two light chains each of said light chains comprising a VL CDR1, a VL CDR2, and a VL CDR3 as set forth in a variable light (VL) chain region comprising the amino acid sequence of SEQ ID NO: 32, and
   wherein the VH CDR1, the VH CDR2, the VH CDR3, the VL CDR1, the VL CDR2, and the VL CDR3 are according to Kabat numbering scheme.

2. The antibody of claim 1, wherein the antibody comprises human IgG4 heavy chains and human kappa light chains.

3. The antibody of claim 1, wherein the antibody prevents human CD47 from interacting with SIRPα.

4. The antibody of claim 1, wherein the antibody promotes macrophage-mediated phagocytosis of a CD47-expressing cell.

* * * * *